US010933116B2

(12) United States Patent
Krishna et al.

(10) Patent No.: US 10,933,116 B2
(45) Date of Patent: Mar. 2, 2021

(54) SYNTHETIC PEPTIDE COMPOUNDS AND METHODS OF USE

(71) Applicant: ReAlta Holdings, LLC, Norfolk, VA (US)

(72) Inventors: Neel K. Krishna, Norfolk, VA (US); Kenji Cunnion, Norfolk, VA (US)

(73) Assignee: REALTA HOLDINGS, LLC, Norfolk, VA (US)

( * ) Notice: Subject to any disclaimer, the term of this patent is extended or adjusted under 35 U.S.C. 154(b) by 277 days.

(21) Appl. No.: 15/738,786

(22) PCT Filed: Jun. 24, 2016

(86) PCT No.: PCT/US2016/039421
§ 371 (c)(1),
(2) Date: Dec. 21, 2017

(87) PCT Pub. No.: WO2016/210370
PCT Pub. Date: Dec. 29, 2016

(65) Prior Publication Data
US 2020/0254053 A1 Aug. 13, 2020

Related U.S. Application Data

(60) Provisional application No. 62/185,202, filed on Jun. 26, 2015.

(51) Int. Cl.
A61K 38/10 (2006.01)
A61P 37/00 (2006.01)
A61P 7/00 (2006.01)
A61P 11/00 (2006.01)
A61P 31/12 (2006.01)
A61K 38/16 (2006.01)

(52) U.S. Cl.
CPC ............ *A61K 38/10* (2013.01); *A61K 38/162* (2013.01); *A61P 7/00* (2018.01); *A61P 11/00* (2018.01); *A61P 31/12* (2018.01); *A61P 37/00* (2018.01)

(58) Field of Classification Search
CPC ...... A61K 38/00; A61K 38/162; A61K 47/60; A61P 25/00; A61P 37/06; A61P 7/00; C07K 14/005
See application file for complete search history.

(56) References Cited

U.S. PATENT DOCUMENTS

| 6,126,939 A | 10/2000 | Eisenbach-Schwartz et al. |
| 6,696,562 B1 | 2/2004 | Schultz-Cherry et al. |
| 7,381,524 B2 | 6/2008 | Schultz-Cherry et al. |
| 8,241,843 B2 | 8/2012 | Krishna et al. |
| 8,906,845 B2 | 12/2014 | Krishna et al. |
| 10,005,818 B2 | 6/2018 | Krishna et al. |
| 2005/0079485 A1 | 4/2005 | Schultz-Cherry et al. |
| 2007/0012617 A1 | 1/2007 | Suzuki et al. |
| 2009/0092581 A1 | 4/2009 | Skawinski et al. |
| 2010/0055106 A1 | 3/2010 | Krishna et al. |
| 2011/0104156 A1 | 5/2011 | Christadoss et al. |
| 2013/0183662 A1 | 7/2013 | Zychlinsky et al. |
| 2013/0244924 A1 | 9/2013 | Krishna et al. |
| 2014/0309175 A1 | 10/2014 | Zhao et al. |
| 2015/0031599 A1 | 1/2015 | Abuchowski et al. |
| 2015/0064176 A1 | 3/2015 | Schwaeble et al. |
| 2016/0376322 A1 | 12/2016 | Krishna et al. |

FOREIGN PATENT DOCUMENTS

| JP | 2013-533273 A | 8/2013 | |
| WO | WO-9426902 | 11/1994 | |
| WO | WO-9944625 | 9/1999 | |
| WO | WO-0043027 | 7/2000 | |
| WO | WO-2005023195 | 3/2005 | |
| WO | WO-2005023296 | 3/2005 | |
| WO | WO-2007145806 | 12/2007 | |
| WO | WO-2007145806 A2 * | 12/2007 | ............. A61P 19/02 |
| WO | WO-2012012600 | 1/2012 | |

(Continued)

OTHER PUBLICATIONS

Kristina A. Stoermer, Complement and viral pathogenesis, Virology 411 (2011) 362-373.*
Karen L. Goldenthal, Chapter 51 Control of Viral Infections and Diseases, NCBI Bookshelf. A service of the National Library of Medicine, National Institutes of Health, pp. 1-10, 1996.*
John Bernet, Viral mimicry of the complement system; J. Biosci. 28 249-264, 2003.*
Mauriello, Clifford T., et al., "A Novel Peptide Inhibitor of Classical and Lectin Complement Activation Including ABO Incompatibility", Molecular Immunology, vol. 53, No. 1-2, pp. 132-139 (Jan. 1, 2013). XP055087953, ISSN 0161-5890, DOI: 10.1016/J.MOLIMM.2012.07.012.
Sharp, Julia A., et al, "Peptide Inhibitor of Complement C1 (PIC1) Rapidly Inhibits Complement Activation After Intravascular Injection in Rats", PLOS One, vol. 10, No. 7, p. e013246, (Jul. 21, 2015). XP055R524426, doi: 10.1371/journal.pone.0132446.

(Continued)

*Primary Examiner* — James H Alstrum-Acevedo
*Assistant Examiner* — Erinne R Dabkowski
(74) *Attorney, Agent, or Firm* — Troutman Pepper Hamilton Sanders LLP

(57) ABSTRACT

The present invention provides synthetic peptide compounds and uses thereof for therapy and diagnostics of complement-mediated diseases, such as inflammatory diseases, autoimmune diseases, and microbial and bacterial infections; and non-complement-mediated diseases, such cystic fibrosis and various acute diseases. The invention is directed to modifications of a synthetic peptide of 15 amino acids from the Polar Assortant (PA) peptide, which is a scrambled peptide derived from human Astrovirus protein. In some embodiments, the invention is directed to peptide compounds that are peptide mimetics, peptide analogs and/or synthetic derivatives of PA (e.g., sarcosine derivatives) having, for example, internal peptide substitutions, and modifications, including PEGylation at the N-terminus and C-terminus. The invention further provides methods of selecting at least one synthetic peptide for treating various conditions.

8 Claims, 52 Drawing Sheets
Specification includes a Sequence Listing.

(56) References Cited

FOREIGN PATENT DOCUMENTS

WO   WO-2012012600 A2 * 1/2012 ........... A61K 38/162

OTHER PUBLICATIONS

Partial Supplementary European Search Report for Application No. 168115455.7 as a Communication Pursuant to Rule 164(1) EPC, dated Jan. 14, 2019.

Japanese Office Action issued in Japanese Patent Application No. 2018-519267 dated May 18, 2020.

Bass and Upadhyayula "Characterization of Human Serotype 1 Astrovirus-Neutralizing Epitopes," Journal of Virology, pp. 8666-8671 (1997).

Bass et al., "Proteolytic processing of the astrovirus capsid," J. Virol. 74(4), pp. 1810-1814 (2000).

Bonaparte et al., "Human Astrovirus Coat Protein Inhibits Serum Complement Activation via C1, the First Component of the Classical Pathway," J. Virol., 82(2), pp. 817-827 (2008).

Caballero et al., "Structural requirements of astrovirus virus-like particles assembled in insect cells," J. Virol., 78(23), pp. 13285-13292 (2004).

Carvalho and Gomes, "Plant defensins—prospects for the biological functions and biotechnological properties," Peptides, 30(5), pp. 1007-1020 (2009).

Castellano et al., "Therapeutic targeting of classical and lectin pathways of complement protects from ischemia-reperfusion-induced renal damage," Amer. J. Pathol., 176, pp. 1648-1659 (2010).

Cooper, "The classical complement pathway: activation and regulation of the first complement component," Adv. Immunol., 37, pp. 151-216 (1985).

Cunnion et al., "Capsule production and growth phase influence binding of complement to *Staphylococcus aureus*," Infect. Immun., 69, pp. 6796-6803 (2001).

Dong et al., "Particle polymorphism caused by deletion of a peptide molecular switch in a quasiequivalent icosahedral virus," J. Virol., 72(7), pp. 6024-6033 (1998).

Favoreel et al., "Virus complement evasion strategies," Journal of General Virology, 84(Pt. 1), pp. 1-15 (2003).

Fogh, ed., "Human tumor cells in vitro," Plenum Press, New York, pp. 115-159 (1975) (47 total pgs.).

Fryer et al., "Synthetic peptides which inhibit the interaction between C1q and immunoglobulin and prolong xenograft survival," Transplantation, 70, pp. 828-836 (2000).

Geigenmüller et al., "Construction of a genome-length cDNA clone for human astrovirus serotype 1 and synthesis of infectious RNA transcripts," J. Virol., 71, pp. 1713-1717 (1997).

GenBank, "Human astrovirus putative serine protease gene, complete cds; putative RNA-dependent RNA polymerase gene, partial cds; and capsid precursor protein gene, complete cds," Accession No. AF141381, <http://www.ncbi.nlm.nih.gov/nuccore/AF141381> retrieved on Nov. 24, 2011 (3 pages).

GenBank, "Human astrovirus type 1 genes for capsid protein and nonstructural protein," Accession No. Z25771, <http://www.ncbi.nlm.nih.gov/nuccore/z25771> retrieved on May 15, 2013 (5 pages).

GenBank, "Non-structural protein, capsid protein (human astrovirus serotype 1, isolate A88/2, Newcastle, Genomic RNA, 2739 nt)," Accession No. S68561, <http://www.ncbi.nlm.nih.gov/nuccore/S68561> retrieved on May 2, 2014 (2 pages).

Groeneveld et al., "Human neutrophil peptide-1 inhibits both the classical and the lectin pathway of complement activation," Molec. Immunol., 44, pp. 3608-3614 (2007).

Gronemus et al., "Potent inhibition of the classical pathway of complement by a novel C1q-binding peptide derived from the human astrovirus coat protein," Molecular Immunology, 48, pp. 305-313 (2010).

Hair et al., "Human astrovirus coat protein binds C1q and MBL and inhibits the classical and lectin pathways of complement activation," Molecular Immunology, 47, pp. 792-798 (2010).

Harris and Chess, "Effect of pegylation on pharmaceuticals," Nature Reviews Drug Discovery, 2, pp. 214-221 (2003).

Huwiler et al., "Optimizing the MALDI-TOF-MS observation of peptides containing disulfide bonds," J. Biomol. Tech., 14, pp. 289-297 (2003).

Zhang et al., "Activation of the lectin pathway by natural IgM in a model of ischemia/reperfusion injury," J. Immunol., 177, pp. 4727-4734 (2006).

Kohno et al., "Development of Simple Latex Agglutination Test for Detection of Astrovirus Serotype 1," Rinsho Biseibutshu Jinsoku Shindan Kenkyukai Shi, 11(2), pp. 87-91 (2000).

Kojima et al., "Inhibition of complement-mediated immune hemolysis by peptides derived from the constant domain of immunoglobulin," Transplantation, 67, pp. 637-638 (1999).

Krishna and Cunnion, "Human Astrovirus Coat Protein: A Novel C1 Inhibitor," Adv. Exp. Med. Biol., 632, pp. 237-251 (2008).

Krishna, "Identification of structural domains involved in astrovirus capsid biology," Viral Immunol. 18(1), 17-26 (2005).

Larkin et al., "Clustal W and Clustal X version 2.0," Bioinformatics, 23, pp. 2947-2948 (2007).

Lauvrak et al., "Identification and characterisation of C1q-binding phage displayed peptides," Biol. Chem., 378, pp. 1509-1519 (1997).

Lee et al., "Early complement factors in the local tissue immunocomplex generated during intestinal ischemia/reperfusion injury," Author Manuscript, published in final form as: Mol. Immunol., 47, pp. 972-981 (2010).

Liu et al., "Solution structure of the plant defensin VrD1 from mung bean and its possible role in insecticidal activity against bruchids," Proteins: Structure, Function, and Bioinformatics, 63, pp. 777-786 (2006).

Lund et al., "X3M a Computer Program to Extract 3D Models," Abstract at the CASP5 conference A102, 2002 (2 pages).

Mallik et al., "Design and NMR characterization of active analogues of Compstatin containing non-natural amino acids," J. Med. Chem., 48, pp. 274-286 (2005).

Méndez-Toss et al., "Molecular Analysis of a Serotype 8 Human Astrovirus Genome," Journal of General Virology, 81, pp. 2891-2897 (2000).

Messmer et al., "Sequential determination of ligands binding to discrete components in heterogeneous mixtures by iterative panning and blocking (IPAB)," J. Mol. Biol., 296, pp. 821-832 (2000).

Morgan and Harris, "Complement therapeutics; history and current progress," Molec. Immunol., 40, pp. 159-170 (2003).

Noris and Remuzzi, "Overview of Complement Activation and Regulation," Semin. Nephrol., 33(6), pp. 479-492 (2013).

Park et al., "A Readily Applicable Strategy to Convert Peptides to Peptoid-based Therapeutics," PLoS One, 8, e58874, pp. 1-7 (2013).

Ricklin and Lambris, "Complement-targeted therapeutics," Author Manuscript, published in final form as: Nat. Biotech., 25, pp. 1265-1275 (2007).

Roos et al., "Specific inhibition of the classical complement pathway by C1q-binding peptides," J. Immunol., 167, pp. 7052-7059 (2001).

Sahu et al., "Inhibition of human complement by a C3-binding peptide isolated from a phage-displayed random peptide library," J. Immunol., 157, pp. 884-891 (1996).

Sambrook and Russell, "Molecular cloning: A Laboratory Manual," Cold Spring Harbor Laboratory Press, Cold Spring Harbor, New York, 3rd ed., 21 pages (2001).

Schneemann et al., "Use of recombinant baculoviruses in synthesis of morphologically distinct viruslike particles of flock house virus, a nodavirus," J. Virol., 67, pp. 2756-2763 (1993).

ScienceDaily, "Research could lead to way to halt deadly immune response," <http://www.sciencedaily.com/releases/2010/02/100209183127.htm>, 2 pages (2010).

Zhang et al., "NMR studies of defensin antimicrobial peptides. 1. Resonance assignment and secondary structure determination of rabbit NP-2 and human HNP-1," Biochemistry, 31, pp. 11348-11356 (1992).

(56) References Cited

OTHER PUBLICATIONS

Younger et al., "Systemic and lung physiological changes in rats after intravascular activation of complement," J. Appl. Physiol., 90, pp. 2289-2295 (2001).
Taylor et al., "Structure-activity relationships in beta-defensin peptides," Biopolymers, 90, pp. 1-7 (2007).
Thermo Electron Corporation, "N-Terminal Acetylation and C-Terminal Amidation of Peptides," Technical Information, 2 pages (2004).
Tjernberg et al., "Acute antibody-mediated complement activation mediates lysis of pancreatic islets cells and may cause tissue loss in clinical islet transplantation," Author Manuscript, published in final form as: Transplantation, 85, pp. 1193-1199 (2008).
UniProtKB/TrEMBL, "Capsid Protein—Human Astrovirus-1 (HAstV-1)," 3 pages, <http://www.uniprot.org/uniprot/A9CE26> (Jul. 22, 2008).
Van den Berg et al., "Inhibition of activation of the classical pathway of complement by human neutrophil defensins," Blood, 92, pp. 3898-3903 (1998).
Vaughn et al., "The establishment of two cell lines from the insect Spodoptera frugiperda (Lepidoptera; Noctuidae)," In Vitro, 13, pp. 213-217 (1977).
Willcocks et al., "Growth and characterisation of human faecal astrovirus in a continuous cell line," Arch. Virol., 113, pp. 73-81 (1990).
International Search Report of International Application No. PCT/US2016/039421 dated Jan. 9, 2017 (5 pages).
Written Opinion of the International Searching Authority of International Application No. PCT/US2016/039421 dated Jan. 9, 2017 (7 pages).
Sharp, Ja et al. Peptide Inhibitor of Complement C1, a Novel Suppressor of Classical Pathway Activation: Mechanistic Studies and Clinical Potential. Aug. 22, 2014, vol. 5; pp. 1-9; abstract; p. 1, second column, first paragraph; p. 2. second column, third paragraph; p. 5, first column, second paragraph; second column, first paragraph; DOI: 10.3389/fimmu.2014.00406.
International Search Report and Written Opinion for International Application No. PCT/US2007/012617, dated Jun. 4, 2008, 11 pages.
Supplementary European Search Report issued in European Application No. 16815455 dated Apr. 17, 2019.
International Search Report and Written Opinion issued in International Application No. PCT/US2019/012659 dated Mar. 19, 2019.
Palmer et al., "Hypochlorous Acide Regulates Neutrophil Extracellular Trap Release in Humans", Clinical and Experimental Immunology, Nov. 1, 2011, vol. 167, Issue 2, pp. 261-268.
Hair et al. "Inhibition of Immune Complex Complement Activation and Neutrophil Extracellular Trap Formation by Peptide Inhibitor of Complement C1", Frontiers in Immunology, Mar. 26, 2018 (Mar. 26, 2018), vol. 9, Article 558, pp. 1-12.
Papayannopoulos et al., "Neutrophil Elastase and Myeloperoxidase Regulate the Formation of Neutrophil Extracellular Traps", The Journal of Cell Biology, 25 Oct. 10, 2010 (Oct. 25, 2010), vol. 191, No. 3, pp. 677-691.
International Search Report and Written Opinion for International Application No. PCT/US2011/044791, dated Mar. 21, 2012, 14 pages.
Zhang et al., "The Role of natural IgM in myocardial ischemia-reperfusion injury", Journal of Molecular and Cellular Cardiolody, 2006, vol. 41, No. 1, 62-67.
Barbee I. Whitaker PSH, PhD, The 2011 National Blood Collection and Utilization Survey Report; 2011.
Murphy et al., "Transfusing Blood safely and appropriately", BMJ, 2013, vol. 347, pp. 29-33.
Refaai et al., "The transfusion dilemma—weighing the known and newly proposed risks of blood transfusions against the uncertain benefits", Best practice & research Clinical anaesthesiology, 2013, vol. 27, No. 1, pp. 17-35.
Aygun et al., "Clinical significance of RBC alloantibodies and autoantibodies in sickle cell patients who received transfusions", Transfusion, 2002, vol. 42, No. 1, pp. 37-43.
Osterman et al., "Blood product transfusions and reactions", Emergency medicine clinics of North America, 2014, vol. 32, No. 3, pp. 727-738.
Stowell et al., "Initiation and regulation of complement during hemolytic transfusion reactions", Clinical & Developmental Immunology, vol. 2012, Article 307093, 2012, pp. 1-12.
Weinstock et al. "Successful use of eculizumab for treatment of an acute hemolytic reaction after ABO-incompatible red blood cell transfusion", Transfusion, 2015, vol. 55, No. 3, pp. 605-610.
European Search Report issued in European Application No. 17153032 dated Apr. 24, 2017.
Shah et al., "Complement inhibition significantly decreases red blood cell lysis in a rat model of acute intravascular hemolysis", Transfusion, 2014, vol. 54, No. 11, pp. 2892-2900.
Aptekman et al.,"Characterization of the natural hemagglutinins in normal rat serum associated with a negative phase following tumor implantation." Cancer Research, 1956, vol. 16, No. 3, pp. 216-221.
Yazdanbakhsh et al., "Complement receptor 1 inhibitors for prevention of immunemediated red cell destruction: potential use in transfusion therapy." Blood, Jun. 2003, vol. 101, No. 12, pp. 5046-5052.
Boyle, "Adult cystic fibrosis", JAMA, 2007, vol. 298, No. 15, pp. 1787-1793.
Rowe et al., "Cystic fibrosis", The New England Journal of Medicine, 2005, vol. 352, No. 19, pp. 1992-2001.
Gibson et al., "Pathophysiology and management of pulmonary infections in cystic fibrosis." Am J Respir Crit Care Med, 2003, vol. 168, No. 8, pp. 918-951.
Gharib et al., "Mapping the lung proteome in cystic fibrosis", Journal of Proteome Research, 2009, vol. 8, No. 6, pp. 3020-3028.
Zawrotniak et al., "Neutrophil extracellular traps (NETs)—formation and implications." Acta Biochimica Polonica. 2013, vol. 60, No. 3, pp. 277-284.
Tralau et al., "Human leukocyte elastase and cathepsin Gare specific inhibitors of CS a-dependent neutrophil enzyme release and chemotaxis", Experimental Dermatology, 2004, vol. 13, No. 5, pp. 316-325.
Dwyer et al., "Cystic Fibrosis Sputum DNA Has NETosis Characteristics and Neutrophil Extracellular Trap Release Is Regulated by Macrophage Migration-Inhibitory Factor", Journal of Innate Immunity, 2014, vol. 6, pp. 765-779.
Hodson, "Aerosolized domase alfa (rhDNase) for therapy of cystic fibrosis", American Journal of Respir Crit Care Med, 1995, vol. 151, (3 Pt 2), pp. S70-S74.
Gifford et al., "The role of neutrophils in cystic fibrosis", Current Opinion Hematology, 2014, vol. 21, No. 1, pp. 16-22.
Le Gars et al., "Neutrophil elastase degrades cystic fibrosis transmembrane conductance regulator via cal pains and disables channel function in vitro and in vivo", Am J Respir Crit Care Med, 2013, vol. 187, Issue 2, pp. 170-179.
Sagel et al., "Sputum biomarkers of inflammation and lung function decline in children with cystic fibrosis", American Journal Respiratory Critrical Care Medicine, 2012, vol. 186, No. 9, pp. 857-865.
Schmudde et al., "C5a receptor signalling in dendritic cells controls the development of maladaptive Th2 and Th17 immunity in experimental allergic asthma", Mucosal Immunology, 2013, vol. 6, No. 4, pp. 807-825.
Bosmann et al., "Role of C3, CS and anaphylatoxin receptors in acute lung injury and in sepsis", Adv Exp Med Biol., 2012, vol. 946, pp. 147-159.
Fick et al., "Complement activation in cystic fibrosis respiratory fluids: in vivo and in vitro generation of C5a and chemotactic activity", Pediatric Research, 1986, vol. 20, No. 12, pp. 1258-1268.
Shah et al. "Clinical hypothermia temperatures increase complement activation and cell destruction via the classical pathway", Journal of Translational Medicine, 2014, vol. 12, 181.
Koseoglu et al., "Effects of hemolysis interferences on routine biochemistry parameters", Biochemia medica, 2011, vol. 21, No. 1, pp. 79-85.

(56) References Cited

OTHER PUBLICATIONS

Schwartz et al., "Hyperbilirubinemia: current guidelines and emerging therapies." Pediatric emergency care. 2011; vol. 27, No. 9, pp. 884-889.
"Management of hyperbilirubinemia in the newborn infant 35 or more weeks of gestation", American Academy of Pediatrics, 2004, vol. 114, No. 1, pp. 297-316.
Cortey et al., "Efficacy and safety of intravenous immunoglobulins in the management of neonatal hyperbilirubinemia due to ABO incompatibility: a meta-analysis." Archives de pediatrie : organe ofjiciel de la Societe francaise de pediatrie. 2014; vol. 21, No. 9, pp. 976-983.
Strobel E., "Hemolytic Transfusion Reactions", Transfusion medicine and hemotherapy : ofjizielles Organ der Deutschen Gesellschaft fur Transfusionsmedizin und Immunhamatologie, 2008; vol. 35, No. 5, pp. 346-353.
Davies et al., "Identification of MUC5B, MUC5AC and small amounts of MUC2 mucins in cystic fibrosis airway secretions", Biochem J., 1999, vol. 344 Pt 2: 321-330.
Hair et al., "Hyperglycemic conditions inhibit C3-mediated immunologic control of *Staphylococcus aureus*", Journal of Translational Medicine, 2012, vol. 10, No. 35, 16 pages.
Mollnes et al., "Essential role of the C5a receptor in *E coli*-induced oxidative burst and phagocytosis revealed by a novel lepirudin-based human whole blood model of inflammation", Blood, 2002, vol. 100, No. 5, pp. 1869-1877.
Laursen et al., "Structure, function and control of complement C5 and its proteolytic fragments", Current Molecular Medicine, 2012, vol. 12, No. 8, pp. 1083-1097.
Supplementary European Search Report issued by the European Patent Office for European Patent Application No. 07809212, 3 pages; dated Sep. 10, 2010.
Aleyd et al., "IgA Complexes in Plasma and Synovial Fluid of Patients with Rheumatoid Arthritis Induce Neutrophil Extracellular Traps via Fc alphaRI". The Journal of Immunology, 2016, vol. 197, No. 12, pp. 4552-4559.
Akong-Moore et al., "Influences of chloride and hypochlorite on neutrophil extracellular trap formation", PLoS ONE, 2012, vol. 7, Issue 8, e42984, 7 pages.
Ballanti et al., "Complement and Autoimmunity". Immunologic Research, 2013, vol. 56, No. 2-3, pp. 477-491.
Bassi et al., "PTX3, Anti-PTX3, and Anti-C1q Autoantibodies in Lupus Glomerulonephritis", Clinical Reviews in Allergy & Immunology, 2015, vol. 49, No. 2, pp. 217-226.
Barilla-Labarca et al., "Targeting the complement system in systemic lupus erythematosus and other diseases", Clinical Immunology. 2013, 148, No. 3, pp. 313-321.
Behnen et al., "Immobilized immune complexes induce neutrophil extracellular trap release by human neutrophil granulocytes via Fcgamma RIIIB and Mac-1", The Journal of Immunology, 2014, vol. 193, No. 4, pp. 1954-1965.
Bergseth et al., "An international serum standard for application in assays to detect human complement activation products", Molecular Immunology, 2013, vol. 56, No. 3, pp. 232-239.
Bestebroer et al., "Functional basis for complement evasion by staphylococcal superantigen-like 7", Cellular Microbiology, 2010, vol. 12, No. 10, pp. 1506-1516.
Carlin et al., "Statistics for clinicians: 4: Basic concepts of statistical reasoning: hypothesis tests and the t-test". Journal of Paediatrics and Child Health, 2001, vol. 37, No. 1, pp. 72-77.

Chen et al., "Endocytosis of soluble immune complexes leads to their clearance by FcgammaRIIIB but induces neutrophil extracellular traps via FcgammaRIIA in vivo", Blood, 2012, vol. 120, No. 22, pp. 4421-4431.
Coulthard et al., "Is the Complement Activation Product C3a a Proinflammatory Molecule? Re-evaluating the Evidence and the Myth" The Journal of Immunology, 2015, vol. 194, No. 8, pp. 3542-3548.
Daha, N.A. et al., "Complement activation by (auto-) antibodies". Molecular Immunology. 2011, 48(14):1656-1665.
Hair et al., "Clumping factor A interaction with complement factor I increases C3b cleavage on the bacterial surface of *Staphylococcus aureus* and decreases complement-mediated phagocytosis", Infection and Immunity, 2010, vol. 78, No. 4, pp. 1717-1727.
Hair et al., "Inhibition of Myeloperoxidase Activity in Cystic Fibrosis Sputum by Peptide Inhibitor of Complement C1 (PIC1)", PLoS ONE, 2017, vol. 12, No. 1, 13 pages.
Hair et al., "Peptide inhibitor of complement CI inhibits the peroxidase activity of hemoglobin and myoglobin", Hindawi International Journal of Peptides, 2017; Article ID 9454583, 10 pages.
Knight et al., "Lupus neutrophils: 'NET' gain in understanding lupus pathogenesis", Current Opinion in Rheumatology, 2012, vol. 24, No. 5, pp. 441-450.
Kraaij et al., "A novel method for high-throughput detection and quantification of neutrophil extracellular traps reveals ROS-independent NET release with immune complexes", Autoimmunity Reviews, 2016, vol. 15, No. 6, pp. 577-584.
Kumar, P.S. et al., "Glucose-based dialysis fluids inhibit innate defense against *Staphylococcus aureus*". Molecular Immunology. 2015, 67:575-583.
Kumar, P.S. et al., "Peptide inhibitor of complement CI modulates acute intravascular hemolysis of mismatched red blood cells in rats". Transfusion. 2016, 56(8):2133-2145.
Lood et al., "Neutrophil extracellular traps enriched in oxidized mitochondrial DNA are interferogenic and contribute to lupus-like disease", Nature Medicine, 2016, vol. 22, No. 2, pp. 146-153.
Lupia et al., "The membrane attack complex of complement contributes to plasmin-induced synthesis of platelet-activating factor by endothelial cells and neutrophils", Immunology, 2003, vol. 109, No. 4, pp. 557-563.
Mayadas et al., "Mechaisms of immune complex-mediated neutrophil recruitment and tissue injury", Circulation, 2009, vol. 120, No. 20, pp. 2012-2024.
Orbai et al., "Anti-C1q antibodies in systemic lupus erythematosus", Lupus, 2015, vol. 24, No. 1, pp. 42-49.
Steil et al., "Platelet-activating factor: the effector of protein-rich plasma extravasation and nitric oxide synthase induction in rat immune complex peritonitis", British Journal of Pharmacology, 1995, vol. 114, No. 4, pp. 895-901.
Thanei, S., et al., "Anti-C1q autoantibodies from systemic lupus erythematosus patients activate the complement system via both the classical and lectin pathways". Clinical Immunology. 2015, 160(2):180-187.
Tralau, T. et al., "Human leukocyte elastase and cathepsin G are specific inhibitors of C5a-dependent neutrophil enzyme release and chemotaxis". Experimental Dermatology. 2004, 13(5):316-325.
Frank et al. ed, "Complement System", In: Austen KF, Atkinson JP, Cantor HI ed. Samter's Immunologic Disease. New York: Lippincott Williams and Wilkins; 2001; pp. 281-299.
Lambris et al., "The chemistry and biology of C3, C4, and C5." In: Volanakis JE, Frank MM, (eds). The human complement system in health and disease. New York: Marcel Dekker; 1998, 83-118.

* cited by examiner

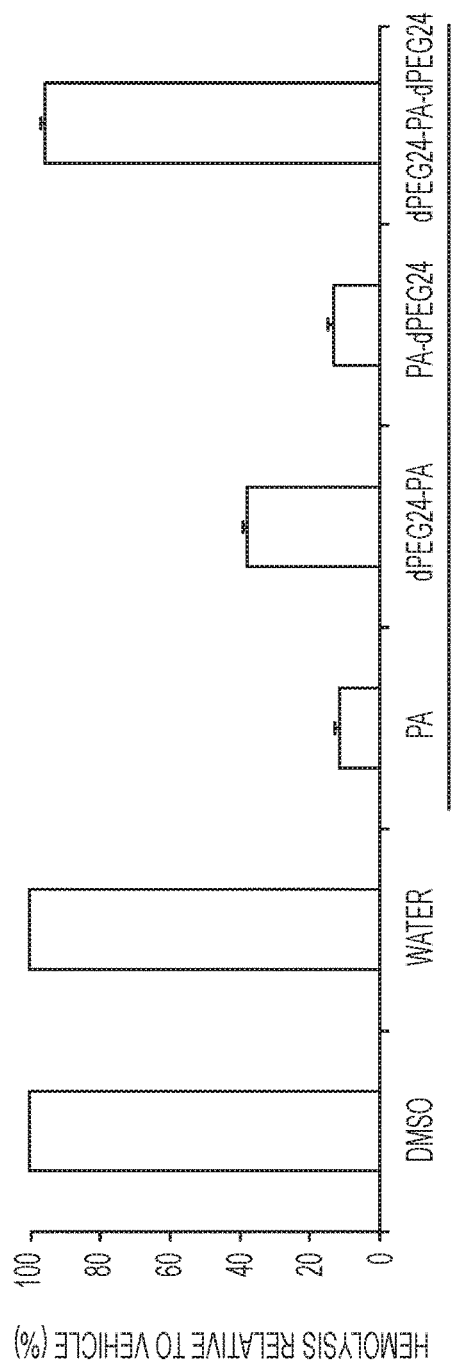
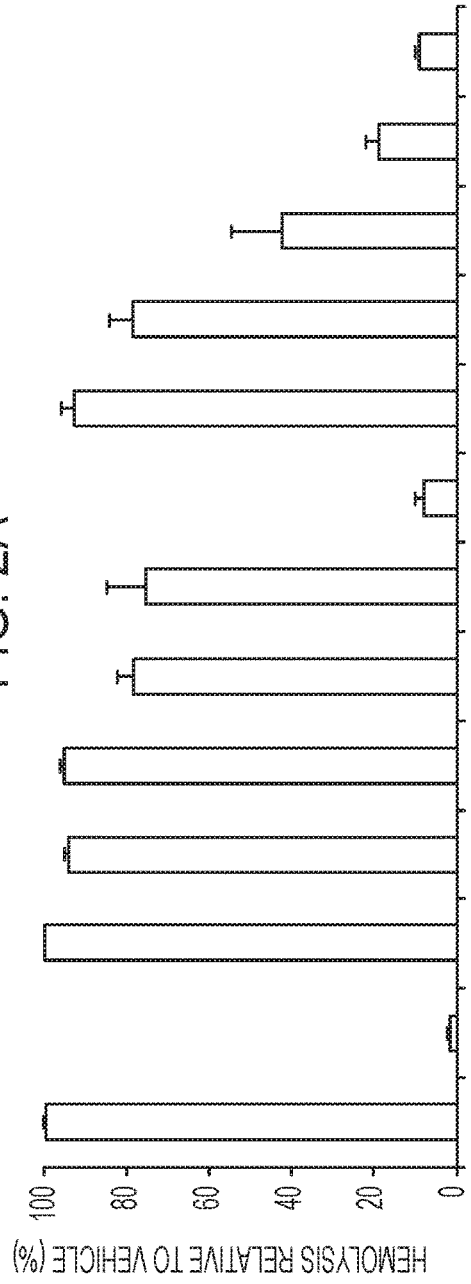
FIG. 2A
FIG. 2B

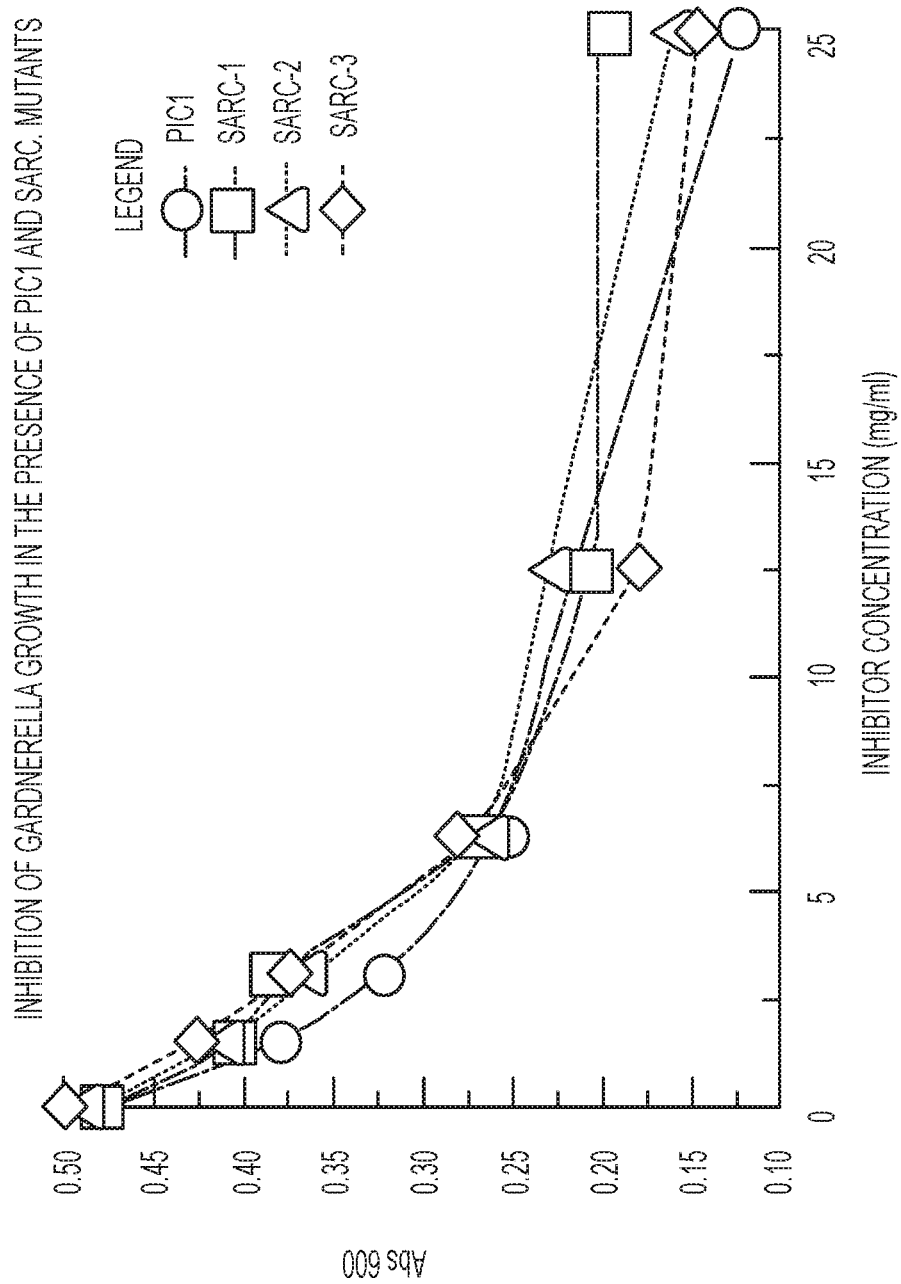

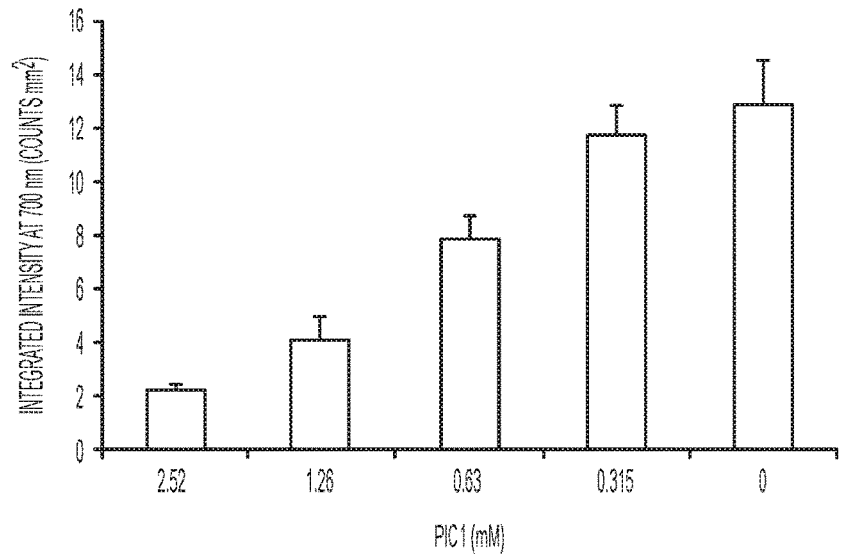
FIG. 14C
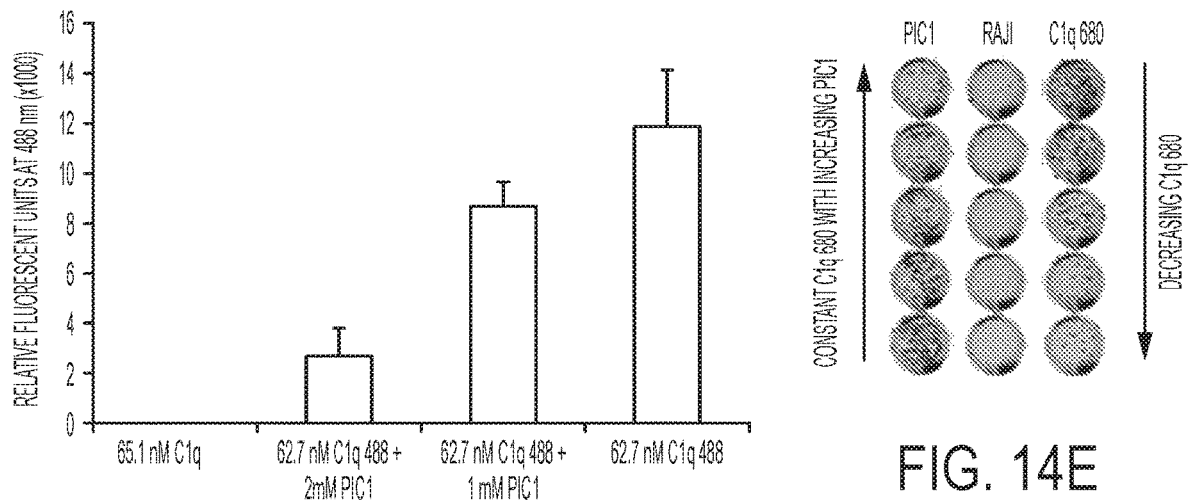
FIG. 14D
FIG. 14E

SEQUENCE LISTING

<160> NUMBER OF SEQ ID NOS: 47

<210> SEQ ID NO 1
<211> LENGTH: 30
<212> TYPE: PRT
<213> ORGANISM: Human astrovirus

<400> SEQUENCE: 1

Pro Ala Ile Cys Gln Arg Ala Thr Ala Thr Leu Gly Thr Val Gly Ser
1               5                   10                  15

Asn Thr Ser Gly Thr Thr Glu Ile Glu Ala Cys Ile Leu Leu
            20                  25                  30

<210> SEQ ID NO 2
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Pro Ala Ile Cys Gln Arg Ala Glu Ile Glu Ala Cys Ile Leu Leu
1               5                   10                  15

<210> SEQ ID NO 3
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ile Ala Leu Ile Leu Glu Pro Ile Cys Cys Gln Glu Arg Ala Ala
1               5                   10                  15

<210> SEQ ID NO 4
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Sarcosine

<400> SEQUENCE: 4

Xaa Ala Leu Ile Leu Glu Pro Ile Cys Cys Gln Glu Arg Ala Ala
1               5                   10                  15

<210> SEQ ID NO 5
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Sarcosine

<400> SEQUENCE: 5

Ile Xaa Leu Ile Leu Glu Pro Ile Cys Cys Gln Glu Arg Ala Ala
1               5                   10                  15

```
<210> SEQ ID NO 6
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Sarcosine

<400> SEQUENCE: 6

Ile Ala Xaa Ile Leu Glu Pro Ile Cys Cys Gln Glu Arg Ala Ala
1               5                   10                  15

<210> SEQ ID NO 7
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Sarcosine

<400> SEQUENCE: 7

Ile Ala Leu Xaa Leu Glu Pro Ile Cys Cys Gln Glu Arg Ala Ala
1               5                   10                  15

<210> SEQ ID NO 8
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Sarcosine

<400> SEQUENCE: 8

Ile Ala Leu Ile Xaa Glu Pro Ile Cys Cys Gln Glu Arg Ala Ala
1               5                   10                  15

<210> SEQ ID NO 9
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Sarcosine

<400> SEQUENCE: 9

Ile Ala Leu Ile Leu Xaa Pro Ile Cys Cys Gln Glu Arg Ala Ala
1               5                   10                  15

<210> SEQ ID NO 10
<211> LENGTH: 15
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Sarcosine

<400> SEQUENCE: 10

Ile Ala Leu Ile Leu Glu Xaa Ile Cys Cys Gln Glu Arg Ala Ala
1               5                   10                  15

<210> SEQ ID NO 11
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Sarcosine

<400> SEQUENCE: 11

Ile Ala Leu Ile Leu Glu Pro Xaa Cys Cys Gln Glu Arg Ala Ala
1               5                   10                  15

<210> SEQ ID NO 12
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Sarcosine

<400> SEQUENCE: 12

Ile Ala Leu Ile Leu Glu Pro Ile Xaa Cys Gln Glu Arg Ala Ala
1               5                   10                  15

<210> SEQ ID NO 13
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Sarcosine

<400> SEQUENCE: 13

Ile Ala Leu Ile Leu Glu Pro Ile Cys Xaa Gln Glu Arg Ala Ala
1               5                   10                  15

<210> SEQ ID NO 14
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Sarcosine
```

```
<400> SEQUENCE: 14

Ala Leu Ile Leu Glu Pro Ile Cys Cys Xaa Glu Arg Ala Ala
1               5                   10

<210> SEQ ID NO 15
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Sarcosine

<400> SEQUENCE: 15

Ile Ala Leu Ile Leu Glu Pro Ile Cys Cys Gln Xaa Arg Ala Ala
1               5                   10                  15

<210> SEQ ID NO 16
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Sarcosine

<400> SEQUENCE: 16

Ile Ala Leu Ile Leu Glu Pro Ile Cys Cys Gln Glu Xaa Ala Ala
1               5                   10                  15

<210> SEQ ID NO 17
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Sarcosine

<400> SEQUENCE: 17

Ile Ala Leu Ile Leu Glu Pro Ile Cys Cys Gln Glu Arg Xaa Ala
1               5                   10                  15

<210> SEQ ID NO 18
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (15)..(15)
<223> OTHER INFORMATION: Sarcosine

<400> SEQUENCE: 18

Ile Ala Leu Ile Leu Glu Pro Ile Cys Cys Gln Glu Arg Ala Xaa
1               5                   10                  15

<210> SEQ ID NO 19
```

```
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(15)
<223> OTHER INFORMATION: N-term dPEG24
<220> FEATURE:
<221> NAME/KEY: MISC_FEATURE
<222> LOCATION: (1)..(15)
<223> OTHER INFORMATION: C-term dPEG24

<400> SEQUENCE: 19

Ile Ala Leu Ile Leu Glu Pro Ile Cys Cys Gln Glu Arg Ala Ala
1               5                   10                  15

<210> SEQ ID NO 20
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(15)
<223> OTHER INFORMATION: N-term dPEG24

<400> SEQUENCE: 20

Ile Ala Leu Ile Leu Glu Pro Ile Cys Cys Gln Glu Arg Ala Ala
1               5                   10                  15

<210> SEQ ID NO 21
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(15)
<223> OTHER INFORMATION: C-term dPEG24

<400> SEQUENCE: 21

Ile Ala Leu Ile Leu Glu Pro Ile Cys Cys Gln Glu Arg Ala Ala
1               5                   10                  15

<210> SEQ ID NO 22
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(15)
<223> OTHER INFORMATION: C-term dPEG20

<400> SEQUENCE: 22

Ile Ala Leu Ile Leu Glu Pro Ile Cys Cys Gln Glu Arg Ala Ala
1               5                   10                  15

<210> SEQ ID NO 23
<211> LENGTH: 15
<212> TYPE: PRT
<213> ORGANISM: Artificial Sequence
```

-continued

```
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(15)
<223> OTHER INFORMATION: C-term dPEG16

<400> SEQUENCE: 23

Ile Ala Leu Ile Leu Glu Pro Ile Cys Cys Gln Glu Arg Ala Ala
1               5                   10                  15

<210> SEQ ID NO 24
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(15)
<223> OTHER INFORMATION: C-term dPEG12

<400> SEQUENCE: 24

Ile Ala Leu Ile Leu Glu Pro Ile Cys Cys Gln Glu Arg Ala Ala
1               5                   10                  15

<210> SEQ ID NO 25
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(15)
<223> OTHER INFORMATION: C-term dPEG08

<400> SEQUENCE: 25

Ile Ala Leu Ile Leu Glu Pro Ile Cys Cys Gln Glu Arg Ala Ala
1               5                   10                  15

<210> SEQ ID NO 26
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(15)
<223> OTHER INFORMATION: C-term dPEG06

<400> SEQUENCE: 26

Ile Ala Leu Ile Leu Glu Pro Ile Cys Cys Gln Glu Arg Ala Ala
1               5                   10                  15

<210> SEQ ID NO 27
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(15)
<223> OTHER INFORMATION: C-term dPEG04
```

<400> SEQUENCE: 27

Ile Ala Leu Ile Leu Glu Pro Ile Cys Cys Gln Glu Arg Ala Ala
1               5                   10                  15

<210> SEQ ID NO 28
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(15)
<223> OTHER INFORMATION: C-term dPEG03

<400> SEQUENCE: 28

Ile Ala Leu Ile Leu Glu Pro Ile Cys Cys Gln Glu Arg Ala Ala
1               5                   10                  15

<210> SEQ ID NO 29
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(15)
<223> OTHER INFORMATION: C-term dPEG02

<400> SEQUENCE: 29

Ile Ala Leu Ile Leu Glu Pro Ile Cys Cys Gln Glu Arg Ala Ala
1               5                   10                  15

<210> SEQ ID NO 30
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Sarcosine

<400> SEQUENCE: 30

Ile Ala Leu Ile Leu Glu Pro Ile Xaa Ala Gln Glu Arg Ala Ala
1               5                   10                  15

<210> SEQ ID NO 31
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Sarcosine

<400> SEQUENCE: 31

Ile Ala Leu Ile Leu Glu Pro Ile Xaa Gln Glu Arg Ala Ala
1               5                   10

```
<210> SEQ ID NO 32
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Sarcosine
<220> FEATURE:
<221> NAME/KEY: MOD_RES
<222> LOCATION: (9)..(9)
<223> OTHER INFORMATION: Sarcosine

<400> SEQUENCE: 32

Ile Ala Leu Ile Leu Glu Xaa Ile Xaa Cys Gln Glu Arg Ala Ala
1               5                   10                  15

<210> SEQ ID NO 33
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(15)
<223> OTHER INFORMATION: C-term dPEG24
<220> FEATURE:
<221> NAME/KEY: MOD_RES
<222> LOCATION: (6)..(6)
<223> OTHER INFORMATION: Sarcosine

<400> SEQUENCE: 33

Ile Ala Leu Ile Leu Xaa Pro Ile Cys Cys Gln Glu Arg Ala Ala
1               5                   10                  15

<210> SEQ ID NO 34
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(15)
<223> OTHER INFORMATION: C-term dPEG24
<220> FEATURE:
<221> NAME/KEY: MOD_RES
<222> LOCATION: (11)..(11)
<223> OTHER INFORMATION: Sarcosine

<400> SEQUENCE: 34

Ile Ala Leu Ile Leu Glu Pro Ile Cys Cys Xaa Glu Arg Ala Ala
1               5                   10                  15

<210> SEQ ID NO 35
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(15)
<223> OTHER INFORMATION: C-term dPEG24
<220> FEATURE:
<221> NAME/KEY: MOD_RES
```

```
<222> LOCATION: (13)..(13)
<223> OTHER INFORMATION: Sarcosine

<400> SEQUENCE: 35

Ile Ala Leu Ile Leu Glu Pro Ile Cys Cys Gln Glu Xaa Ala Ala
1               5                   10                  15

<210> SEQ ID NO 36
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(15)
<223> OTHER INFORMATION: C-term dPEG24
<220> FEATURE:
<221> NAME/KEY: MOD_RES
<222> LOCATION: (14)..(14)
<223> OTHER INFORMATION: Sarcosine

<400> SEQUENCE: 36

Ile Ala Leu Ile Leu Glu Pro Ile Cys Cys Gln Glu Arg Xaa Ala
1               5                   10                  15

<210> SEQ ID NO 37
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(7)
<223> OTHER INFORMATION: Sarcosine

<400> SEQUENCE: 37

Ile Ala Leu Ile Leu Xaa Xaa Ile Cys Cys Gln Glu Arg Ala Ala
1               5                   10                  15

<210> SEQ ID NO 38
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Sarcosine
<220> FEATURE:
<221> NAME/KEY: MOD_RES
<222> LOCATION: (9)..(9)
<223> OTHER INFORMATION: Sarcosine

<400> SEQUENCE: 38

Ile Ala Leu Ile Leu Xaa Pro Ile Xaa Cys Gln Glu Arg Ala Ala
1               5                   10                  15

<210> SEQ ID NO 39
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (7)..(7)
<223> OTHER INFORMATION: Sarcosine
<220> FEATURE:
<221> NAME/KEY: MOD_RES
<222> LOCATION: (11)..(11)
<223> OTHER INFORMATION: Sarcosine

<400> SEQUENCE: 39

Ile Ala Leu Ile Leu Glu Xaa Ile Cys Cys Xaa Glu Arg Ala Ala
1               5                   10                  15

<210> SEQ ID NO 40
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Sarcosine
<220> FEATURE:
<221> NAME/KEY: MOD_RES
<222> LOCATION: (11)..(11)
<223> OTHER INFORMATION: Sarcosine

<400> SEQUENCE: 40

Ile Ala Leu Ile Leu Glu Pro Ile Xaa Cys Xaa Glu Arg Ala Ala
1               5                   10                  15

<210> SEQ ID NO 41
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Sarcosine
<220> FEATURE:
<221> NAME/KEY: MOD_RES
<222> LOCATION: (13)..(13)
<223> OTHER INFORMATION: Sarcosine

<400> SEQUENCE: 41

Ile Ala Leu Ile Leu Glu Xaa Ile Cys Cys Gln Glu Xaa Ala Ala
1               5                   10                  15

<210> SEQ ID NO 42
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Sarcosine
<220> FEATURE:
<221> NAME/KEY: MOD_RES
<222> LOCATION: (13)..(13)
<223> OTHER INFORMATION: Sarcosine

<400> SEQUENCE: 42

Ile Ala Leu Ile Leu Glu Pro Ile Xaa Cys Gln Glu Xaa Ala Ala
1               5                   10                  15
```

```
<210> SEQ ID NO 43
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Sarcosine
<220> FEATURE:
<221> NAME/KEY: MOD_RES
<222> LOCATION: (14)..(14)
<223> OTHER INFORMATION: Sarcosine

<400> SEQUENCE: 43

Ile Ala Leu Ile Leu Glu Xaa Ile Cys Cys Gln Glu Arg Xaa Ala
1               5                   10                  15

<210> SEQ ID NO 44
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Sarcosine
<220> FEATURE:
<221> NAME/KEY: MOD_RES
<222> LOCATION: (14)..(14)
<223> OTHER INFORMATION: Sarcosine

<400> SEQUENCE: 44

Ile Ala Leu Ile Leu Glu Pro Ile Xaa Cys Gln Glu Arg Xaa Ala
1               5                   10                  15

<210> SEQ ID NO 45
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(15)
<223> OTHER INFORMATION: C-term dPEG24

<400> SEQUENCE: 45

Ile Ala Leu Ile Leu Ala Pro Ile Cys Cys Gln Ala Arg Ala Ala
1               5                   10                  15

<210> SEQ ID NO 46
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Sarcosine

<400> SEQUENCE: 46

Ile Ala Leu Ile Leu Ala Pro Ile Xaa Cys Gln Ala Arg Ala Ala
1               5                   10                  15
```

```
<210> SEQ ID NO 47
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Sarcosine

<400> SEQUENCE: 47

Ile Ala Leu Ile Leu Ala Xaa Ile Cys Cys Gln Ala Arg Ala Ala
1               5                   10                  15
```

SYNTHETIC PEPTIDE COMPOUNDS AND METHODS OF USE

CROSS REFERENCE TO RELATED APPLICATIONS

This application is a U.S. national phase of International Application No. PCT/US2016/039421, filed Jun. 24, 2016, which claims the benefit of priority under 35 U.S.C. § 119(e) to U.S. Provisional Application No. 62/185,202, filed Jun. 26, 2015, the entire contents of which is hereby incorporated by reference herein.

STATEMENT REGARDING FEDERALLY SPONSORED RESEARCH

This invention was made with government support under the Virginia Innovation Partnership i6 funding mechanism (Sub-Award #GG11598142515), awarded by the U.S. Depaihnent of Commerce. The government has certain rights in the invention.

SEQUENCE LISTING

The instant application contains a Sequence Listing which has been submitted in ASCII format via EFS-Web and is hereby incorporated by reference in its entirety. Said ASCII copy, created on Mar. 8, 2020, is named Seqlist_251110_000047_ST25.txt, and is 17,088 bytes in size.

FIELD

The invention relates to synthetic peptide compounds and uses thereof for therapy and diagnostics, including for complement-mediated diseases, such as inflammatory diseases, autoimmune diseases, and microbial and bacterial infections; and non-complement-mediated diseases, such cystic fibrosis and various acute diseases.

BACKGROUND

The Complement System

The complement system, an essential component of the innate immune system, plays a critical role as a defense mechanism against invading pathogens, primes adaptive immune responses, and helps remove immune complexes and apoptotic cells. Three different pathways comprise the complement system: the classical pathway, the lectin pathway and alternative pathway. C1q and mannose-binding lectin (MBL) are the structurally related recognition molecules of the classical and lectin pathways, respectively. Whereas IgM or clustered IgG serve as the principal ligands for C1q, MBL recognizes polysaccharides such as mannan. Ligand binding by C1q and MBL results in the sequential activation of C4 and C2 to form the classical and lectin pathway C3-convertase. In contrast, alternative pathway activation does not require a recognition molecule, but can amplify C3 activation initiated by the classical or lectin pathways. Activation of any of these three pathways results in the formation of inflammatory mediators (C3a and C5a) and the membrane attack complex (MAC), which causes cellular lysis.

While the complement system plays a critical role in many protective immune functions, complement activation is a significant mediator of tissue damage in a wide range of autoimmune and inflammatory disease processes. (Ricklin and Lambris, "Complement-targeted therapeutics." Nat Biotechnol 2007; 25(11):1265-75).

A need exists for complement regulators. On the one hand, the complement system is a vital host defense against pathogenic organisms. On the other hand, its unchecked activation can cause devastating host cell damage. Currently, despite the known morbidity and mortality associated with complement dysregulation in many disease processes, including autoimmune diseases such as systemic lupus erythematosus, myasthenia gravis, and multiple sclerosis, only two anti-complement therapies have recently been approved for use in humans: 1) purified, human C1-Inhibitor licensed for use in patients suffering from hereditary angioedema (HAE) and 2) eculizumab (Soliris™), a humanized, long-acting monoclonal antibody against C5 used in the treatment of paroxysmal nocturnal hemoglobinuria (PNH). Both PNH and HAE are orphan diseases in which very few people are afflicted. Currently, no complement regulators are approved for the more common disease processes in which dysregulated complement activation plays a pivotal role. Dysregulated complement activation can play a role in both chronic disease indications and acute disease indications. Acute disease indications include, amongst others, acute intravascular hemolytic transfusion reaction (AIHTR), birth asphyxia, hypoxic ischemic encephalopathy, ischemia-reperfusion injury (IRI) in myocardial infarct, coronary artery bypass surgery and stroke, and solid organ transplantation rejection.

Astrovirus Coat Protein

The Astroviridae constitute a family of non-enveloped, icosahedral viruses with a single-stranded, messenger-sense RNA genome. These viruses are a significant cause of gastroenteritis in humans as well as other diseases in other animal species. It is estimated that they cause an estimated 2-17% of children's diarrheal illness worldwide.

The Astrovirus coat protein ("CP") reduces the activity of the complement system, suggesting that the 'active' portion of the protein may have clinical utility in decreasing tissue damage from complement-mediated diseases. The wild type coat protein ("WT CP") purified from human astrovirus type 1 (HAstV-1) can bind C1q and MBL, and regulates both classical and lectin pathway activation (Bonaparte et al., 2008. J. Virol. 82, 817-827; Hair et al., 2010. Molec. Immunol. 47, 792-798). This property is analogous to the properties described for human neutrophil peptide-1 (HNP-1)(Van Den Berg et al., 1998. Blood. 92, 3898-3903; Groeneveld et al., 2007. Molec. Immunol. 44, 3608-3614). The HAstV-1 coat protein is a 787 amino acid molecule that has been expressed from a recombinant baculovirus construct and then purified (Bonaparte et al., 2008. J. Virol. 82, 817-827).

Developing peptide compounds to inhibit classical, lectin and alternative pathways of the complement system is needed, as each of these three pathways have been demonstrated to contribute to numerous autoimmune and inflammatory disease processes. Specific blockade of classical and lectin pathways is particularly needed, as both of these pathways have been implicated in ischemia reperfusion-induced injury in many animal models. Humans with alternative pathway deficiencies suffer severe bacterial infections. Thus, a functional alternative pathway is essential for immune surveillance against invading pathogens.

Microbial and Bacterial Infections

Many microorganisms are resistant to currently available antibiotics. Current antibiotics are derived from other microbial organisms that bacteria have competed against for space and energy over many years, which has led to rapid and predictable emergence of resistance. Some of the most pathogenic bacteria to humans are *Pseudomonas aeruginosa, Staphylococcus aureus*, MRSA, and carbapenemase-resistant enterobacteriacea (CREs) such as *Klebsiella pneumonia. Pseudomonas aeruginosa* and *Staphylococcus aureus* are also major pathogens in cystic fibrosis lungs. *Gardnerella* is a Gram variable, anaerobic coccobacillus that is a common cause of bacterial vaginosis. *Gardnerella* also causes complement activation and inflammation, which causes the symptoms of bacterial vaginosis and increases the risk of HIV transmission by disrupting normal barrier defenses in the vagina. There is a need for treatments for bacterial vaginosis that kill the causative organism and block inflammation. There is also a need for novel antimicrobial compounds given the increasing resistance to conventional antibiotics.

Herpes simplex virus 1 (HSV-1) and herpes simplex virus 2 (HSV-2) are viruses responsible for causing herpes. Infection with HSV-1 can happen from general interactions such as eating from the same utensils, sharing lip balm, or kissing. The virus is highly contagious, and it is possible to get genital herpes from HSV-1 if the individual has had cold sores and performed sexual activities during that time. Similarly, HSV-2 is also highly contagious. HSV-2 is contracted through forms of sexual contact with a person who has HSV-2. It is estimated that around 20 percent of sexually active adults within the United States have been infected with HSV-2, according to the American Academy of Dermatology (AAD). While HSV-2 infections are spread by coming into contact with a herpes sore, the AAD reports that most people get HSV-1 from an infected person who is asymptomatic, or does not have sores. Current treatments like acyclovir for HSV-1 or HSV-2 may not be fully efficacious. Thus, there is a need for anti-viral treatments for HSV-1 and HSV-2 that are more effective against viruses.

*Lactobacillus* Growth

*Lactobacillus* is a genus of bacteria that contains over 180 species. Multiple *Lactobacillus* species are often administered together as a single probiotic agent. In combination, various *Lactobacillus* species have been known to help individuals with irritable bowel syndrome, prevent necrotizing enterocolitis, and other neonatal infections. Because of its many health benefits, there is a need for compounds that can stimulate growth of *Lactobacillus* species.

Cystic Fibrosis

Cystic fibrosis (CF) is a genetic disease caused by mutations in the cystic fibrosis transmembrane conductance regulator (CFTR) gene. Patients with CF produce unusually thick, sticky mucus that clogs the lungs and leads to life-threatening lung infections, and obstructs the pancreas and stops natural enzymes from helping the body break down food and absorb vital nutrients. CF is characterized by a cycle of small airway obstruction, infection with bacterial pathogens, e.g., *P. aeruginosa, Staphylococcus aureus* (including methicillin-resistant *S. aureus* (MRSA), *Burkholderia cepacia*, and inflammatory lung damage. Complement-mediated inflammation may be a major contributor to inflammatory lung damage in CF. Treatment of CF includes a regular treatment routine to maintain lung health and good nutrition. Other treatments for CF include airway clearance every day to help loosen and clear thick mucus that can build up in the lungs, inhaled medicines, including antibiotics, to help keep the airways clear, and pancreatic enzyme supplements to improve absorption of vital nutrients. There is a need for both anti-inflammatory and anti-microbial treatments for CF.

Hemolytic Transfusion Reactions

Blood transfusions can be life-saving, but can also carry the risk of a variety of reactions, some of which are potentially life-threatening, such as acute intravascular hemolytic transfusion reactions (AIHTRs). AIHTR is estimated to occur in one-fifth of total transfusions. Individuals receiving frequent blood transfusions will develop alloantibodies and autoantibodies to red blood cell (RBC) antigens over time, making cross-matching increasingly difficult and thus increasing the risk of AIHTR. Current transfusion safe-guards include "typing", "antibody screening", as well as "cross matching." While these measures have made transfusions safer, transfusion reactions still occur. AIHTR occurs when host antibodies bind to the transfused erythrocytes, initiating classical complement pathway activation, which leads to the generation of the inflammatory mediators C3a and C5a, as well as C3b opsonization and hemolysis of the transfused cells via the membrane attack complex (MAC). To date, only one case has been reported describing clinical intervention of an AIHTR by inhibiting generation of the complement anaphylatoxins C3a and C5a. No specific interventions for these reactions exist; current management of the reaction is supportive in nature. While existing safeguards make ABO incompatibility rare in the developed world, individuals with sickle cell disease and severe thalassemias requiring frequent transfusions are at increased risk for transfusion reactions due to the accumulation of antibodies against minor antigenic determinates on erythrocytes. Neonatal ABO incompatibility in newborns can lead to jaundice, and, in severe cases, kernicterus. No blood banking organization or transfusion medicine practice has a method to directly evaluate risk for complement-mediated red blood cell lysis between donor and recipient. There is currently no effective medical intervention for ATRs except for stopping the transfusion. Diagnostic tools, prophylactic treatments to prevent AIHTR, and rescue treatments during an AIHTR are needed.

Birth Asphyxia

Birth asphyxia is a medical condition resulting from deprivation of oxygen to a newborn that causes brain damage. Hypoxic ischemic encephalopathy (HIE) is a condition that occurs when the entire brain is deprived of an adequate oxygen supply, but the deprivation is not total. HIE is most often associated with birth asphyxia. Reperfusion injury is the tissue damage caused when blood supply returns to a tissue after a period of ischemia or lack of oxygen. The absence of oxygen and nutrients from blood during the ischemic period creates a condition in which the restoration of circulation results in inflammation and oxidative damage through the induction of oxidative stress rather than restoration of normal function. Complement activation is instrumental in the development of ischemia-reperfusion injuries such as neonatal HIE. Therapeutic hypothermia (HT), the current standard of care for HIE, offers only an 11% reduction in death or disability. Published data has shown that HT paradoxically increases pro-inflammatory complement activation, which potentially limits its benefit. There is a need for treatments for HIE and birth asphyxia that regulate complement and have neuroprotective effects.

Autoimmune Hemolytic Anemia

Autoimmune hemolytic anemia (AIHA) is a disease that occurs when antibodies directed against a person's own red blood cells cause them to burst, leading to insufficient plasma concentration. AIHA is most commonly caused by IgG and IgM. IgM is a potent activator of the classical complement pathway. Thus, AIHA is characterized by complement mediated lysis of red blood cells. Thus, there is a need for therapies directed at the complement system to treat AIHA.

It would be desirable to develop peptide compounds that can regulate complement activation and can be used therapeutically to prevent and treat complement-mediated diseases, such as inflammatory and autoimmune diseases. It would also be desirable to develop peptide compounds that treat acute diseases and conditions such as acute intravascular hemolytic transfusion reaction (AIHTR), birth asphyxia, autoimmune hemolytic anemia, viral infections, and bacterial infections, amongst others. It would also be desirable to develop peptide compounds that treat cystic fibrosis.

SUMMARY

In one aspect, the present invention provides synthetic peptide compounds that regulate the complement system and methods of using these compounds. Specifically, in some embodiments, the synthetic peptide compounds can bind, regulate and inactivate C1 and MBL, and therefore can efficiently inhibit classical and lectin pathway activation at its earliest point while leaving the alternative pathway intact. These peptide compounds are of therapeutic value for selectively regulating and inhibiting C1 and MBL activation without affecting the alternative pathway and can be used for treating diseases mediated by dysregulated activation of the classical and lectin pathways. In other embodiments, the peptide compounds regulate classical pathway activation but not lectin pathway activation. The peptide compounds are useful for various therapeutic indications—even for indications that are unrelated to complement regulation. In some embodiments, these peptide compounds are of therapeutic value for treating acute diseases and conditions such as acute intravascular hemolytic transfusion reaction (AIHTR), birth asphyxia, as well as bacterial, viral, and antimicrobial infections, amongst others. These peptide compounds are also of therapeutic value for treating cystic fibrosis.

In some embodiments, the invention is based on the identification and modification of peptides of 15 amino acids from Polar Assortant (PA) peptide (SEQ ID NO: 3), derivatives of the peptides, and methods of their use. The PA peptide is a scrambled peptide derived from human astrovirus protein, called CP1 (SEQ ID NO: 1). The PA peptide is also known as PIC1 (Peptide Inhibitors of Complement C1), AstroFend, AF, or SEQ ID NO: 3. As used herein, the term "PIC1 peptides" include SEQ ID NO:3 as well as other amino acid sequences that are the same as SEQ ID NO:3 but with PEGylation modifications. The PIC1 peptide was originally named as such because it was found to be associated with diseases mediated by the complement system. In some aspects, surprisingly, the invention is also related to use of the PA peptide and derivatives for treating diseases and conditions that are not associated with the complement system, such as, but not limited to, cystic fibrosis and chronic obstructive pulmonary disease (COPD). In some embodiments, the invention is based on the PIC1 peptide and modifications thereof, having the amino acid sequences and modifications as set forth in SEQ ID NOs: 3-47. These peptides can be used to regulate complement activation, including complement inhibition; treat and/or prevent hemolytic reactions; treat hypoxic ischemic encephalopathy; treat cystic fibrosis; for anti-microbial use; and to treat and/or prevent other diseases and conditions disclosed herein.

In some aspects, the invention is directed to peptide compounds that are peptide mimetics, peptide analogs and/or synthetic derivatives of PA having, for example, internal peptide deletions and substitutions, deletions and substitutions at the N terminus and C terminus, and that are able to regulate the classical and lectin pathway activation by binding to C1q and MBL.

A further embodiment of the invention is any one of the peptide compounds of this invention, wherein the peptide compound is modified through sarcosine substitution, alanine substitution, and/or PEGylation of the N terminus, C terminus, or N terminus and C terminus.

In some embodiments, the peptide sequence has at least about 80%, at least about 85%, at least about 90%, at least about 91%, at least about 92%, at least about 93%, at least about 94%, at least about 95%, at least about 96%, at least about 97%, at least about 98%, or at least about 99% sequence identity to SEQ ID NOs: 3-47.

In one aspect, the invention provides a method of treating and/or preventing a hemolytic reaction in a subject in need thereof comprising: administering to the subject in need thereof a composition comprising a therapeutically effective amount of a synthetic peptide comprising at least about 90% sequence identity to an amino acid sequence selected from the group consisting of SEQ ID NO: 3-47. In some embodiments, the synthetic peptide has the amino acid sequence and modifications selected from the group consisting of SEQ ID NO: 3-47. In other embodiments, the hemolytic reaction is selected from the group consisting of acute intravascular hemolytic transfusion reaction (AIHTR), transfusion related acute lung injury (TRALI), and platelet transfusion refractoriness. In further embodiments, the composition is administered before the subject is administered a blood transfusion, after the subject is administered the blood transfusion, and/or during the blood transfusion.

In another aspect, the invention provides a method of treating hypoxic ischemic encephalopathy in a subject in need thereof comprising: administering to the subject in need thereof a composition comprising a therapeutically effective amount of a synthetic peptide comprising at least about 90% sequence identity to an amino acid sequence selected from the group consisting of SEQ ID NO: 3-47. In some embodiments, the synthetic peptide has the amino acid sequence and modifications selected from the group consisting of SEQ ID NO: 3-47.

In another aspect, the invention provides a method of treating cystic fibrosis in a subject in need thereof comprising: administering to the subject in need thereof a composition comprising a therapeutically effective amount of a synthetic peptide comprising at least about 90% sequence identity to an amino acid sequence selected from the group consisting of SEQ ID NO: 3-47. In some embodiments, the synthetic peptide has the amino acid sequence and modifications selected from the group consisting of SEQ ID NO: 3-47.

In another aspect, the invention provides a method of treating a bacterial infection in a subject in need thereof comprising: administering to the subject in need thereof a composition comprising a therapeutically effective amount of a synthetic peptide comprising at least about 90% sequence identity to an amino acid sequence selected from the group consisting of SEQ ID NO: 3-47. In some embodiments, the synthetic peptide has the amino acid sequence and modifications selected from the group consisting of SEQ ID NO: 3-47. In some embodiments, the bacterial infection is caused by bacteria selected from the group consisting of *Staphylococcus aureus, Klebsiella pneumonia, Pseudomonas aeruginosa, Neisseria gonorrhoeae, Chlamydia tra-*

*chomatis*, and *Gardnerella* sp. In further embodiments, the bacterial infection is caused by Gram-positive or Gram-negative bacteria.

In another aspect, the invention provides a method of enhancing *Lactobacillus* growth in a subject comprising: administering to the subject a composition comprising a therapeutically effective amount of a synthetic peptide comprising at least about 90% sequence identity to an amino acid sequence selected from the group consisting of SEQ ID NO: 3-47. In some embodiments, the synthetic peptide has the amino acid sequence and modifications selected from the group consisting of SEQ ID NO: 3-47.

In another aspect, the invention provides a method of treating a viral infection in a subject in need thereof comprising: administering to the subject in need thereof a composition comprising a therapeutically effective amount of a synthetic peptide comprising at least about 90% sequence identity to an amino acid sequence and modifications selected from the group consisting of SEQ ID NO: 3-47. In some embodiments, the synthetic peptide has the amino acid sequence and modifications selected from the group consisting of SEQ ID NO: 3-47. In some embodiments, the viral infection is caused by herpes simplex virus 1 (HSV-1) or herpes simplex virus 2 (HSV-2).

In another aspect, the invention provides a method of treating autoimmune hemolytic anemia in a subject in need thereof comprising: administering to the subject in need thereof a composition comprising a therapeutically effective amount of a synthetic peptide comprising at least about 90% sequence identity to an amino acid sequence selected from the group consisting of SEQ ID NO: 3-47. In some embodiments, the synthetic peptide has the amino acid sequence and modifications selected from the group consisting of SEQ ID NO: 3-47. The autoimmune hemolytic anemia may be characterized by one or more of elevated serum bilirubin, excess urinary urobilinogen, reduced plasma haptoglobin, raised serum lactic dehydrogenase (LDH), hemosiderinuria, methemalbuminemia, spherocytosis, reticulocytosis, and/or erythroid hyperplasia of the bone marrow.

In another aspect, the invention provides a method of treating birth asphyxia in a subject in need thereof comprising: administering to the subject in need thereof a composition comprising a therapeutically effective amount of a synthetic peptide comprising at least about 90% sequence identity to an amino acid sequence selected from the group consisting of SEQ ID NO: 3-47. In some embodiments, the synthetic peptide has the amino acid sequence and modifications selected from the group consisting of SEQ ID NO: 3-47. In some embodiments, presence of birth asphyxia is characterized by an Apgar score of 3 or under that lasts five minutes or more.

In another aspect, the invention provides a method of treating acute kidney injury in a subject in need thereof comprising: administering to the subject in need thereof a composition comprising a therapeutically effective amount of a synthetic peptide comprising at least about 90% sequence identity to an amino acid sequence selected from the group consisting of SEQ ID NO: 3-47. In some embodiments, the synthetic peptide has the amino acid sequence and modifications selected from the group consisting of SEQ ID NO: 3-47.

In another aspect, the invention is a synthetic peptide comprising at least about 90% sequence identity to an amino acid sequence of SEQ ID NO: 3-47. In some embodiments, a pharmaceutical composition can comprise a therapeutically effective amount of the synthetic peptide and at least one pharmaceutically acceptable carrier, diluent, or excipient.

In another aspect, the invention is a synthetic peptide comprising the amino acid sequence and modifications of SEQ ID NO: 3-47. In some embodiments, the invention is a synthetic peptide comprising the amino acid sequence and modifications of SEQ ID NO: 4-18 and 30-47. In some embodiments, the invention is a synthetic peptide comprising the amino acid sequence and modifications of SEQ ID NO: 3 and 19-29. In some embodiments, the invention is a synthetic peptide comprising the amino acid sequence and PEGylation modifications of SEQ ID NO: 21. In some embodiments, a pharmaceutical composition can comprise a therapeutically effective amount of the synthetic peptide and at least one pharmaceutically acceptable carrier, diluent, or excipient.

In another aspect, the invention is directed to a PIC1 peptide, wherein the peptide is modified through PEGylation of the N terminus, the C terminus, or both the N terminus and C terminus. In another aspect, the invention is directed to a PIC1 peptide, wherein the peptide has been modified by sarcosine and/or alanine substitutions. In other embodiments, the peptide is modified through PEGylation and sarcosine and/or alanine substitutions. In some embodiments, the peptides are isolated and/or purified.

In one aspect, the invention provides a method of selecting at least one peptide for treating a subject having cystic fibrosis comprising: (a) testing peptides selected from the group consisting of SEQ ID NOs: 3-47 for activity on cystic fibrosis; and (b) selecting from the group consisting of SEQ ID NOs: 3-47 at least one synthetic peptide having activity on cystic fibrosis.

In another aspect, the invention provides a method of selecting at least one peptide for treating a subject having a hemolytic reaction comprising: (a) testing peptides selected from the group consisting of SEQ ID NOs: 3-47 for activity on the hemolytic reaction; and (b) selecting from the group consisting of SEQ ID NOs: 3-47 at least one synthetic peptide having activity on the hemolytic reaction. In some embodiments, the hemolytic reaction is selected from the group consisting of AIHTR, transfusion related acute lung injury (TRALI), and platelet transfusion refractoriness.

In another aspect, the invention provides a method of selecting at least one peptide for treating a subject having a bacterial infection comprising: (a) testing peptides selected from the group consisting of SEQ ID NOs: 3-47 for activity on the bacterial infection; and (b) selecting from the group consisting of SEQ ID NOs: 3-47 at least one synthetic peptide having activity on the bacterial infection. In some embodiments, the bacterial infection is caused by bacteria selected from the group consisting of *Staphylococcus aureus, Klebsiella pneumonia, Pseudomonas aeruginosa, Neisseria gonorrhoeae, Chlamydia trachomatis*, and *Gardnerella* sp. In some embodiments, the bacterial infection is caused by Gram-positive or Gram-negative bacteria.

In another aspect, the invention provides a method of selecting at least one peptide for enhancing growth of *Lactobacillus* comprising (a) testing peptides selected from the group consisting of SEQ ID NOs: 3-47 for activity enhancing growth of *Lactobacillus* species; and (b) selecting from the group consisting of SEQ ID NOs: 3-47 at least one synthetic peptide having activity enhancing growth of *Lactobacillus* species.

In another aspect, the invention provides a method of selecting at least one peptide for treating and/or preventing a viral infection comprising (a) testing peptides selected from the group consisting of SEQ ID NOs: 3-47 for activity that treats or prevents the viral infection; and (b) selecting from the group consisting of SEQ ID NOs: 3-47 at least one synthetic peptide having activity that treats or prevents the viral infection. In some embodiments, the viral infection is caused by HSV-1 or HSV-2.

In another aspect, the invention provides a method of selecting at least one peptide for treating and/or preventing autoimmune hemolytic anemia comprising (a) testing peptides selected from the group consisting of SEQ ID NOs: 3-47 for activity on autoimmune hemolytic anemia; and (b) selecting from the group consisting of SEQ ID NOs: 3-47 at least one synthetic peptide having activity on autoimmune hemolytic anemia.

In another aspect, the invention provides a method or selecting at least one peptide for treating birth asphyxia comprising (a) testing peptides selected from the group consisting of SEQ ID NOs: 3-47 for activity on birth asphyxia; and (b) selecting from the group consisting of SEQ ID NOs: 3-47 at least one synthetic peptide having activity on birth asphyxia.

In another aspect, the invention provides a method of selecting at least one peptide for treating hypoxic ischemic encephalopathy comprising: (a) testing peptides selected from the group consisting of SEQ ID NOs: 3-47 for activity on hypoxic ischemic encephalopathy; and (b) selecting from the group consisting of SEQ ID NOs: 3-47 at least one synthetic peptide having activity on hypoxic ischemic encephalopathy.

In other aspects, the invention provides a method of treating a disease by administering the compositions described herein, wherein the disease that is at least partially complement mediated includes but is not limited to: hemolytic transfusion reactions, cold-agglutinin disease, immune-complex diseases, thalassemia, sickle cell disease, ABO incompatibility, acute/hyperacute solid organ transplantation rejection, instant blood-mediated inflammatory reaction (IBMIR), solid organ transplantation warm/cold ischemia, systemic lupus erythematosus (SLE), rheumatoid arthritis, ischemia-reperfusion injury, myocardial infarct, stroke, hypoxic ischemic encephalopathy, traumatic brain injury, coronary artery bypass surgery, wound healing, cancer, Alzheimer's disease, Parkinson's disease, paroxysmal nocturnal hemoglobinuria (PNH), atypical hemolytic uremic syndrome (aHUS), asthma, Crohn's disease, Sepsis syndrome/ARDS/SIRS, glomerulonephritis, lupus nephritis, anti-glomerular basement membrane disease, anti-neutrophil cytoplasmic autoantibody-induced, membranoproliferative glomerulonephritis, dense deposit disease, membranous nephropathy, IgA nephropathy, or C3 glomerulopathy.

In another aspect, the invention provides a method of treating a disease by administering the compositions described herein, wherein the disease is not complement-mediated, which includes but is not limited to cystic fibrosis and chronic obstructive pulmonary disease (COPD).

Another embodiment of the invention is a method of treating a disease associated with complement-mediated tissue damage, further comprising administering to a subject at least one other active ingredient effective in treating the disease, wherein at least one other active ingredient includes a non-steroidal anti-inflammatory agent, a corticosteroid, a disease modifying anti-rheumatic drug, C1-inhibitor, and eculizumab.

Unless otherwise defined, all technical and scientific terms used herein have the same meaning as commonly understood by one of ordinary skill in the art. Although methods and materials similar or equivalent to those described herein can be used in the practice or testing of the present invention, suitable methods and materials are described below. All publications, patent applications, patents, and other references mentioned herein are incorporated by reference in their entirety. In addition, the materials, methods, and examples are illustrative only and not intended to be limiting.

Other features and advantages of the invention will be apparent from the detailed description, drawings, and claims.

BRIEF DESCRIPTION OF THE FIGURES

FIGS. 2A-B show THAT PA-dPEG24 (SEQ ID NO: 21) inhibits complement activation in a hemolytic assay using factor B depleted serum to the same degree as PA (SEQ ID NO: 3).

FIG. 4A shows plate dilution assays for *Staphylococcus aureus* treated with PA-dPEG24 (SEQ ID NO: 21) or saline control. The X-axis shows inhibitor concentration of PA-dPEG24 (SEQ ID NO: 21) in mg/ml. FIG. 4B shows plate dilution assays for *Staphylococcus aureus* treated with PA-dPEG24 or Vancomycin. The X-axis shows inhibitor concentration of PA-dPEG24 (SEQ ID NO: 21) in mg/ml, and vancomycin starting at 5 µg/ml. FIG. 4C shows plate dilution assays for *Klebsiella pneumonia* treated with PA-dPEG24 (SEQ ID NO: 21) or Gentamycin. The X-axis shows inhibitor concentration of PA-dPEG24 (SEQ ID NO: 21) in mg/ml. Gentamycin starting at 4 µg/ml. FIG. 4D shows plate dilution assays for *Pseudomonas aeruginosa* treated with PA-dPEG24 (SEQ ID NO: 21) or Gentamycin control. The X-axis shows inhibitor concentration of PA-dPEG24 (SEQ ID NO: 21) in mg/ml. Gentamycin starting at 4 µg/ml. FIG. 4E shows plate dilution assays for *Pseudomonas aeruginosa* treated with four different versions of PA-dPEG24 (SEQ ID NO: 21) or Gentamycin control. Figure Legend: PIC1=PA-dPEG24 (SEQ ID NO: 21); PA-L3Sar (H2N-IA(Sar) ILEPICCQERAA-OH) (SEQ ID NO: 6); PA-I4Sar (H2N-IAL(Sar)LEPICCQERAA-OH) (SEQ ID NO: 7); PA-L5Sar (H2N-IALI(Sar)EPICCQERAA-OH) (SEQ ID NO: 8).

FIG. 5 shows inhibition of *Gardnerella* growth in the presence of PA-dPEG24 (SEQ ID NO: 21), PA-L3Sar (SEQ ID NO: 6), PA-I4Sar (SEQ ID NO: 7), or PA-L5Sar (SEQ ID NO: 8). PIC1=PA-dPEG24 (SEQ ID NO: 21); Sarc-1=PA-L3Sar (SEQ ID NO: 6); Sarc-2=PA-I4Sar (SEQ ID NO: 7); Sarc-3=PA-L5Sar (SEQ ID NO: 8).

FIG. 10A: C5a concentrations in soluble (sol) fractions from sputum of CF patients (n=15) and controls (n=3). Box shows quartiles, whiskers are $90^{th}$ and $10^{th}$ percentile, and dashed line is the mean. CF sols C5a level is 5-fold higher than control sols (P=0.04). FIG. 10B: C5a Western blot for sputum sols for two healthy controls (A and B) and 2 CF subjects (X and Y). FIG. 10C: C3a concentrations in sol fractions from sputum of CF patients (n=14) and controls (n=4). Box shows quartiles, whiskers are $90^{th}$ and $10^{th}$ percentile, and dashed line is the mean. P=0.03. FIG. 10D: C4a concentrations in sol fractions from sputum of CF patients (n=15) and controls (n=5). Box shows quartiles, whiskers are $90^{th}$ and $10^{th}$ percentile, and dashed line is the mean. P=0.05.

FIG. 11A: *Staphylococcus aureus*-bound C3-fragments after incubation in sol fractions from sputum of CF patients (n=5) and controls (n=3). Box shows quartiles, whiskers are $90^{th}$ percentile, and dashed line is the mean. P=0.42. FIG. 11B: *Staphylococcus aureus*-bound C4-fragments after incubation in sol fractions from sputum of CF patients (n=5) and controls (n=3). Box shows quartiles, whiskers are $90^{th}$ and $10^{th}$ percentile, and dashed line is the mean. P=0.13.

FIG. 12A: C5a concentrations in sol fractions from sputum of CF patients (n=3) or controls (n=3) before and after incubation with live or dead *Pseudomonas aeruginosa* or *Staphylococcus aureus*. Data are means±SE. C5a was generated in CF sol in the presence of *Pseudomonas aeruginosa* (P=0.03) or *Staphylococcus aureus* (P=0.03). FIG. 12B: C5a concentrations in sol fractions from sputum of CF patients (subjects A, B, and C) before (Initial) and after incubation with live or dead *Pseudomonas aeruginosa*. FIG. 12C: C5a concentrations in sol fractions from sputum of CF patients (subjects A, B, and C) before (Initial) and after incubation with live or dead *Staphylococcus aureus*. FIG. 12D: C5a concentrations in CF sols that were incubated alone in buffer (CF sol only), incubated with dead *Pseudomonas aeruginosa* (CF sol+*Pseudomonas aeruginosa*), or incubated with PA-dPEG24 (SEQ ID NO: 21) and dead *Pseudomonas aeruginosa* (CF sol+PA-dPEG24+*P. aeruginosa*). PA-dPEG24, SEQ ID NO: 21 reduces C5a generation in CF sols incubated with *Pseudomonas aeruginosa*.

FIG. 13A: C5a concentrations in CF sols positively correlate with increasing age, r=0.53, P=0.04. FIG. 13B: C5a concentrations in CF sols correlate inversely with BMI percentile in children, r=−0.77, P=0.04. FIG. 13C: C3a concentrations in CF sols positively correlate with FEV1%, $r_s$=0.63, P=0.02.

FIGS. 14A-E shows peptide compounds binding and inhibiting C1q. FIG. 14A: shows PA (SEQ ID NO: 3) binding to C1q, but not to CRT or BSA. FIG. 14B shows PIC1 (SEQ ID NO: 21) inhibits DyLight 680 labeled C1q binding in recombinant CRT. FIG. 14C shows PIC1 (SEQ ID NO: 21) inhibits DyLight labeled 488 C1q binding to Raji cells, and FIG. 14D shows representative In-Cell Western plate assay imaged on LICOR Odyssey demonstrating that increasing amounts of PIC1 (SEQ ID NO: 21) inhibit DyLight 680 labeled C1q from binding Raji cells. FIG. 14E shows the experiment setup.

FIG. 17B: FITC (C1q) at ⅕₀s exposure. FIG. 17C: DAPI at ⅕₀₀s exposure. FIG. 17A: Overlay.

FIG. 18B: FITC (C1q) at ⅕₀s exposure. FIG. 18C: DAPI at ⅕₀₀s exposure. FIG. 18A: Overlay.

FIG. 19B: FITC (C1q) at ⅕₀s exposure. FIG. 19C: DAPI at ⅕₀₀s exposure. FIG. 19A: Overlay.

FIG. 21A shows PA-dPEG24 (SEQ ID NO: 21) dosing in AIHTR model, FIG. 21B shows PA-dPEG24 (SEQ ID NO: 21) efficacy in AIHTR model.

FIG. 22A shows free hemoglobin present in rat plasma collected at 0 sec (pre-bleed), 30 seconds, 5 minutes, 20 minutes, 60 minutes, and 120 minutes after 15% transfusion of human red blood cells (HuRBCs), measured by spectrophotometry. Vehicle control is saline. Positive control is cobra venom factor (CVF). n=number of animals in each group. Error bars denote standard error of the means. FIG. 22B shows percent of surviving HuRBCs (detected using FITC-conjugated anti-human CD235a (glycophorin A monoclonal antibody) at 30 seconds, 5 minutes and 20 minutes after transfusion measured by flow cytometry. Error bars denote standard error of the means. CVF: cobra venom factor. Saline: 0.9% normal saline.

FIG. 23A shows free hemoglobin present in rat plasma collected at 0 second (pre-bleed), 30 seconds, 5 minutes, 20 minutes, 60 minutes, and 120 minutes after 15% transfusion of HuRBCs, measured by spectrophotometry. Error bars denote standard error of the means. FIG. 23B shows area under the curve (total hemoglobin released) over 120 minutes. Error bars denote standard error of the means. FIG. 23C shows unconjugated bilirubin measured at 120 minutes compared to pre-transfusion (pre-bleed). Error bars denote standard error of the means.

FIG. 24A shows flow cytometry analysis of HuRBCs incubated for 5 min in rat serum then labeled with anti-glycophorin A (APC) and anti-C3 (FITC). Labeled opsonized RBCs spiked into unlabeled RBCs (representative plot). FIG. 24B shows flow cytometry analysis of HuRBC's incubated 5 min in rat serum treated with PA-dPEG24 (representative plot). FIG. 24C shows relative increase in number of HuRBCs with no C3 deposition (Q3) in PA-dPEG24 treated serum compared to untreated serum after 5 min. Error bars denote standard error of the means for two independent experiments. FIG. 24D shows percent of serum-incubated RBCs that bound C3-fragments (Q2/Q2+ Q3) is reduced in PA-dPEG24 treated serum compared to untreated serum after 5 min. Error bars denote standard error of the means for 2 independent experiments. Q2: Cells dual stained with C3 and glycophorin A (C3 deposition on glycophorin A labeled cells). Q3: Cells with glycophorin A label (intact cells).

In FIGS. 25A-C, the animal was given saline control. In FIGS. 25D-F, the animal was prophylactically treated with PA-dPEG24 (SEQ ID NO: 21). Q2: Cells dual stained with C3 and glycophorin A. Q3: Cells with glycophorin A label (intact HuRBCs).

FIG. 26A shows the number of events measured at 30 seconds after transfusion with HuRBCs showing all anti gpA+ RBCs (Q2+Q3), anti gpA+ anti C3-(Q3) and anti gpA+ anti C3+(Q2) for PA-dPEG24 (SEQ ID NO: 21) prophylaxis, saline control, CVF (cobra venom factor) control and PA-dPEG24 (rescue) treatment. Error bars denote standard error of the means. FIG. 26B shows percent of anti gpA+, anti C3+ RBCs compared with total anti gpA+ RBCs (Q2/Q2+Q3). Error bars denote standard error of the means. FIG. 26C shows total anti gpA+ RBCs (Q2+Q3) present in blood at 5 minutes and 20 minutes compared to the controls (Saline and CVF). Error bars denote standard error of the means. FIG. 26D shows anti gpA-anti C3+ RBCs (Q1) present in blood up to 20 minutes. Legend: PIC1 (SEQ ID NO: 21) prophylaxis is denoted with a star; PIC1 (SEQ ID NO: 21) Treatment (rescue treatment compared with saline control) is denoted with a diamond; saline control is denoted with a square; CVF control is denoted with a triangle. Error bars denote standard error of the means.

FIGS. 27A-C show the animal prophylactically treated with IVIG. FIGS. 27D-F show the animal prophylactically treated with PA-dPEG24. Q2 shows cells dual stained with C3 and glycophorin A. Q3 shows cells with glycophorin A label (intact HuRBCs).

FIG. 28A shows free hemoglobin present in rat plasma collected at 0 second (pre-bleed), 30 seconds, 5 minutes, 20 minutes, 60 minutes, 120 minutes, 180 minutes, 240 minutes, 300 minutes, and 360 minutes after 15% transfusion of HuRBCs, measured by spectrophotometry. Error bars denote standard error of the means. FIG. 28B shows number of events measured at 30 seconds after transfusion with HuRBCs showing all anti gpA+ RBCs (Q2+Q3), anti gpA+ anti C3-(Q3) and anti gpA+ anti C3+(Q2) for PA-dPEG24 prophylaxis and IVIG prophylaxis. Error bars denote standard error of the means. FIG. 28C shows anti gpA- anti C3+ RBCs (Q1) present in blood at 30 seconds for PA-dPEG24 prophylaxis and IVIG prophylaxis. Error bars denote standard error of the means.

FIG. 29A shows gross kidney weights measured for IVIG prophylaxis and PA-dPEG24 prophylaxis prior to formalin fixing. Error bars denote standard error of the means, n=6. FIG. 29B shows gross kidney image for IVIG prophylaxis and PA-dPEG24 prophylaxis prior to formalin fixing (representative animal). FIG. 29C Representative histology (hematoxylin and eosin stain) of kidneys from rats receiving saline (i, ii), IVIG prophylaxis (iii, iv), or PIC1 prophylaxis (v, vi). PIC1-treated rats demonstrate normal kidney architecture, whereas saline- and IVIG-treated rats show disruption of cellular architecture consistent with acute tubular necrosis. Bar represents 20 mm. Tissues were observed with a microscope (Bmax, Olympus) at a magnification of 4003 at room temperature. Images were acquired with a digital camera (DP71, Olympus).

FIG. 36A shows that PIC1 (SEQ ID NO: 21) inhibits growth of *Staphylococcus aureus*, *Pseudomonas aeruginosa*, and *Klebsiella pneumoniae* in microdilution MIC testing. FIG. 36B shows peptide variants AF1-AF5 (SEQ ID NO: 21, 5, 6, 7 and 8, respectively) in microdilution MIC testing for *Pseudomonas aeruginosa*. FIG. 36C shows confocal microscopy showing PIC1 (SEQ ID NO: 21) bound to the outer surface of bacteria.

FIG. 37A shows *Neisseria gonorrhoeae* growth in presence or absence of 20 mg/ml of PIC1 (SEQ ID NO: 21). FIG. 37B shows *Neisseria gonorrhoeae* growth in presence or absence of 30 mg/ml of PIC1 (SEQ ID NO: 21). FIG. 37C shows *Neisseria gonorrhoeae* grown in titration concentrations of PIC1 (SEQ ID NO: 21). FIG. 37D shows colony counts from *Neisseria gonorrhoeae* incubated with and without PIC1 (SEQ ID NO: 21).

DETAILED DESCRIPTION

Figure 1:
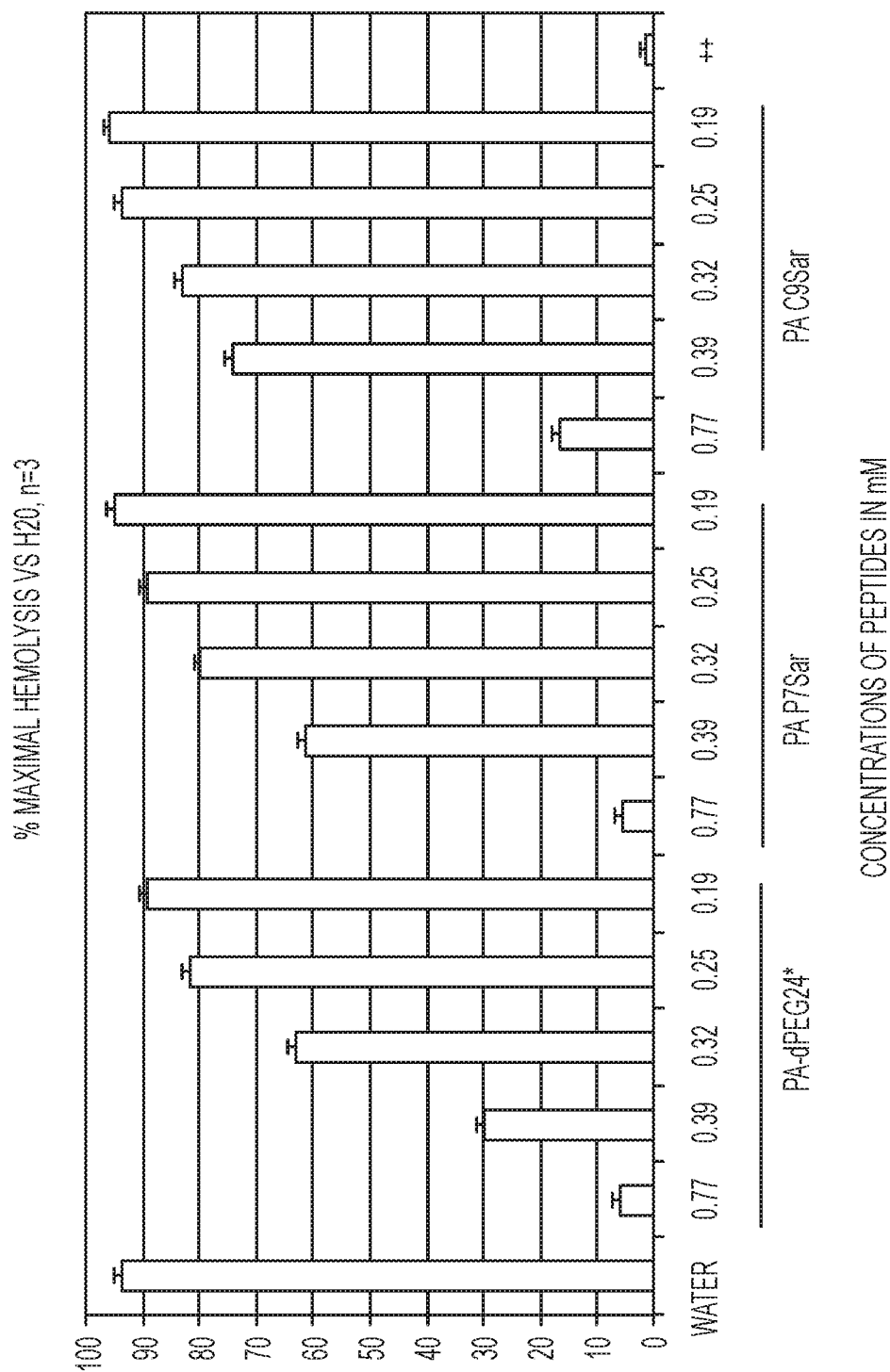
FIG. 1 shows the titration of PA-dPEG24 (SEQ ID NO: 21), PA-P7Sar (SEQ ID NO: 10), and PA-C9Sar (SEQ ID NO: 12), in a hemolytic assay using factor B depleted serum. Concentrations of peptides are shown in mM.

The present invention provides synthetic peptide compounds based on the modification of isolated, purified peptides of 15 amino acids from Polar Assortant (PA) peptide (SEQ ID NO: 3), derivatives of the peptides, and methods of their use. The PA peptide is a scrambled, shortened peptide derived from human astrovirus protein, called CP1 (SEQ ID NO: 1). In some embodiments, the invention is based on modification of an isolated, purified peptide of CP1, and the peptide derivatives have the amino acid sequences set forth in SEQ ID NOs:4-47. SEQ ID NOs: 4-47 are derivatives of PA (SEQ ID NO: 3) having, for example, sarcosine substitutions and/or modifications at the N terminus and C terminus, including PEGylation. These peptides can be used to regulate complement activation, including complement inhibition; treat and/or prevent hemolytic reactions; treat hypoxic ischemic encephalopathy; treat cystic fibrosis; for antimicrobial use; and treat and/or prevent other diseases and conditions disclosed herein.

In some aspects, these peptide compounds are of therapeutic value for the treatment of diseases and conditions mediated by dysregulated activation of the classical and lectin pathways. In some aspects, the invention provides methods for selecting peptides that have anti-microbial activity, can be used to treat cystic fibrosis, and/or can be used to treat various acute diseases. The PA peptide (SEQ ID NO: 3) has low solubility in aqueous solutions. The peptides of SEQ ID NO: 21 and other PEGylated and sarcosine substitutions (e.g., SEQ ID NOs: 5-8, 10-12, 21-25, 27-29, 30-40, 43, 45, and 47), have increased solubility in aqueous solutions, which may increase their efficacy as therapeutic compounds.

In some embodiments, the invention is based on the identification and modification of an isolated, purified peptide of 30 amino acids derived from human astrovirus coat protein, termed CP1, and having a sequence (SEQ ID NO:1) that is able to regulate the classical and lectin pathway activation by binding to C1q and MBL. In other embodiments, the peptide compounds regulate the classical pathway activation but not the lectin pathway activation.

Modifications of the amino acid structure of CP1 has led to the discovery of additional peptide compounds that are able to regulate complement activation, such as C1q activity.

The term "peptide compound(s)," as used herein, refers to amino acid sequences, which may be naturally occurring, or peptide mimetics, peptide analogs and/or synthetic derivatives of about 15 amino acids based on SEQ ID NO: 3. In addition, the peptide compound may be less than about 15 amino acid residues, such as between about 10 and about 15 amino acid residues and such as peptide compounds between about 5 to about 10 amino acid residues. Peptide residues of, for example, 5, 6, 7, 8, 9, 10, 11, 12, 13, 14, and 15 amino acids are equally likely to be peptide compounds within the context of the present invention. Peptide compounds can also be more than 15 amino acids, such as, for example, 16, 17, 18, 19, and 20, or more amino acids.

The disclosed peptide compounds are generally constrained (that is, have some element of structure as, for example, the presence of amino acids that initiate a β turn or β pleated sheet, or, for example, are cyclized by the presence of disulfide bonded Cys residues) or unconstrained (that is, linear) amino acid sequences of about 15 amino acid residues, or less than about 15 amino acid residues.

Substitutes for an amino acid within the peptide sequence may be selected from other members of the class to which the amino acid belongs. For example, the nonpolar (hydrophobic) amino acids include alanine, leucine, isoleucine, valine, proline, phenylalanine, tryptophan, and methionine. Amino acids containing aromatic ring structures include phenylalanine, tryptophan, and tyrosine. The polar neutral amino acids include glycine, serine, threonine, cysteine, tyrosine, asparagine, and glutamine. The positively charged (basic) amino acids include arginine and lysine. The negatively charged (acidic) amino acids include aspartic acid and glutamic acid. For example, one or more amino acid residues within the sequence can be substituted by another amino acid of a similar polarity, which acts as a functional equivalent, resulting in a silent alteration.

A conservative change generally leads to less change in the structure and function of the resulting protein. A non-conservative change is more likely to alter the structure, activity, or function of the resulting protein. For example, the peptide of the present disclosure comprises one or more of the following conservative amino acid substitutions: replacement of an aliphatic amino acid, such as alanine, valine, leucine, and isoleucine, with another aliphatic amino acid; replacement of a serine with a threonine; replacement of a threonine with a serine; replacement of an acidic residue, such as aspartic acid and glutamic acid, with another acidic residue; replacement of a residue bearing an amide group, such as asparagine and glutamine, with another residue bearing an amide group; exchange of a basic residue, such as lysine and arginine, with another basic residue; and replacement of an aromatic residue, such as phenylalanine and tyrosine, with another aromatic residue.

Particularly preferred amino acid substitutions include:

a) Ala for Glu or vice versa, such that a negative charge may be reduced;
b) Lys for Arg or vice versa, such that a positive charge may be maintained;
c) Ala for Arg or vice versa, such that a positive charge may be reduced;
d) Glu for Asp or vice versa, such that a negative charge may be maintained;
e) Ser for Thr or vice versa, such that a free —OH can be maintained;
f) Gln for Asn or vice versa, such that a free NH2 can be maintained;
g) Ile for Leu or for Val or vice versa, as roughly equivalent hydrophobic amino acids;
h) Phe for Tyr or vice versa, as roughly equivalent aromatic amino acids; and
i) Ala for Cys or vice versa, such that disulphide bonding is affected.

Substitutes for an amino acid within the peptide sequence may be selected from any amino acids, including, but not limited to alanine, arginine, asparagine, aspartic acid, cysteine, glutamic acid, glutamine, glycine, histidine, isoleucine, leucine, lysine, methionine, phenylalanine, proline, pyrrolysine, selenocysteine, serine, threonine, tryptophan, tyrosine, valine, N-formyl-L-methionine, sarcosine, or other N-methylated amino acids. In some embodiments, sarcosine substitutes for an amino acid within the peptide sequence.

In one embodiment, the invention discloses synthetic peptides derived from human astrovirus coat protein, the peptides comprising the amino acid sequences and modifications of SEQ ID NOs: 3-47. In some embodiments, the invention discloses synthetic peptides derived from human astrovirus coat protein, the peptides comprising the amino acid sequences and modifications of SEQ ID NOs: 3 and 19-29. In others embodiments, the invention discloses synthetic peptides derived from human astrovirus coat protein, the peptides comprising the amino acid sequences and modifications of SEQ ID NOs: 4-18 and 30-47.

In another embodiment, the invention discloses a synthetic peptide comprising the amino acid sequence of SEQ ID NO: 3, with one or more amino acid substitutions, modifications, insertions, or deletions, wherein the peptide regulates complement activation and/or has anti-microbial activity, amongst other therapeutic activities described herein.

In another embodiment, the invention discloses a synthetic peptide comprising the amino acid sequence of SEQ ID NO: 3, with one or more sarcosine substitutions, wherein the peptide regulates complement activation and/or has anti-microbial activity amongst other therapeutic activities described herein.

In another embodiment, the invention discloses a synthetic peptide comprising the amino acid sequence of SEQ ID NO: 3, with one or more alanine substitutions, wherein the peptide regulates complement activation and/or has anti-microbial activity amongst other therapeutic activities described herein.

In another embodiment, the invention discloses a synthetic peptide comprising the PEGylated amino acid sequence of SEQ ID NO: 3, wherein the peptide regulates complement activation and/or has anti-microbial activity amongst other therapeutic activities described herein.

The peptide compounds may have internal peptide deletions and substitutions as well as deletions and substitutions at the N-terminus and C-terminus based on SEQ ID NO: 3. In some embodiments, the peptide has about 1, 2, 3, 4, 5, 6, 7, 8, 9, 10 or more amino acid substitutions, modifications, insertions, or deletions.

In some embodiments, the peptide sequence has at least about 80%, at least about 85%, at least about 90%, at least about 91%, at least about 92%, at least about 93%, at least about 94%, at least about 95%, at least about 96%, at least about 97%, at least about 98%, or at least about 99% sequence identity to SEQ ID NO: 3.

In some embodiments, the present invention relates to therapeutically active peptides having the effects of treating or preventing organ dysfunction induced by ischemia, inflammation and/or toxic effects of poising or drug treatment. In other embodiments, the present invention also relates to therapeutically active peptides having anti-microbial effects. In other embodiments, the present invention relates to therapeutically active peptides having the effect of treating cystic fibrosis. In other embodiments, the present invention relates to therapeutically active peptides having the effect of treating or preventing acute intravascular hemolytic transfusion reactions (AIHTRs). In other embodiments, the present invention relates to therapeutically active peptides having the effect of treating birth asphyxia. The present invention also relates to therapeutically active peptides having the effect of treating acute complement-mediated diseases.

As used herein, a peptide sequence is "therapeutically active" if it can be used for the treatment, remission, or attenuation of a disease state, physiological condition, symptoms or etiological indication(s) or evaluation or diagnosis thereof. A peptide sequence is "prophylactically active" if it can be used to prevent a disease state, physiological condition, symptoms or etiological indications.

The term "subject," as used herein, means any subject for whom diagnosis, prognosis, or therapy is desired. For example, a subject can be a mammal, e.g., a human or non-human primate (such as an ape, monkey, orangutan, or chimpanzee), a dog, cat, guinea pig, rabbit, rat, mouse, horse, cattle, or cow.

As used herein, "treat," "treating," or "treatment" refers to administering a therapy in an amount, manner (e.g., schedule of administration), and/or mode (e.g., route of administration), effective to improve a disorder (e.g., a disorder described herein) or a symptom thereof, or to prevent or slow the progression of a disorder (e.g., a disorder described herein) or a symptom thereof. This can be evidenced by, e.g., an improvement in a parameter associated with a disorder or a symptom thereof, e.g., to a statistically significant degree or to a degree detectable to one skilled in the art. An effective amount, manner, or mode can vary depending on the subject and may be tailored to the subject. By preventing or slowing progression of a disorder or a symptom thereof, a treatment can prevent or slow deterioration resulting from a disorder or a symptom thereof in an affected or diagnosed subject.

Astrovirus Coat Protein Peptides and Derivatives

CP1 is a peptide derived from human astrovirus coat protein, the peptide comprising an amino acid sequence of SEQ ID NO: 1.

Using CP1 as the parent peptide, internal deletions of residue 8 to residue 22 were made for the 48-22 peptide (SEQ ID NO: 2) (internal deletions are shown as dashes in TABLE 1). This peptide was active in all functional assays tested and bound C1q. The 15 amino acid residues from 48-22 peptide were scrambled to generate the Polar Assortant peptide (SEQ ID NO. 3). The scrambled Polar Assortant peptide (SEQ ID NO: 3) is also referred to as PA, PIC1, AstroFend, or AF. As discussed herein, the term "PIC1" peptide includes peptides with the amino acid sequence set forth in SEQ ID NO: 3 as well as peptides with the same amino acid sequence but with modifications such as PEGylation. The PA peptide was active in all functional assays tested. A series of other peptide deletions, substitutions, and modifications of CP1 are described in U.S. Pat. No. 8,906,845, the contents of which are hereby incorporated by reference in its entirety.

A series of peptide substitutions, and modifications of PA are disclosed, as shown in TABLES 1, 2, 3, and 4 below. This application discloses synthetic peptides comprising any one of the amino acid sequences of SEQ ID NOs: 1-47, as shown in TABLES 1-4. As therapeutic agents for humans, the route of administration for the peptide compounds may be, for example, topical, enteral, inhaled, parenteral (i.e. intramuscular, subcutaneous, intravenous), or administered through a nebulizer, as well as any other routes of administration known in the art.

TABLE 1

| Peptide | Peptide sequence (N→C) |
|---|---|
| CP1 | PAICQRATATLGTVGSNTSGTTEIEACILL (SEQ ID NO: 1) |
| Δ8-22 | PAICQRA---------------EIEACILL (SEQ ID NO: 2) |
| Polar Assortant (also known as PA, PIC1, AstroFend, or AF) | IALILEPICCQERAA (SEQ ID NO: 3) |

Sarcosine Substitutions

Sarcosine ("Sar") is a natural amino acid, also known as N-methylglycine. Sarcosine is an intermediate in the metabolism of choline to glycine. Sarcosine substitution was used to substitute each residue of PA sequentially (TABLE 2). Sarcosine substitution can be used to identify a peptide that retains complement inhibiting activity and is soluble in water.

Disclosed herein are peptide compounds substituted with sarcosine at certain positions. Table 2 discloses synthetic peptides comprising the sequence of SEQ ID NO: 3, wherein one or more of the amino acids are substituted with sarcosine, and wherein the peptides regulate complement activation and/or have anti-microbial activity. In one or more embodiments, the amino acids substituted with sarcosine are at positions 7, or 9. In one or more embodiments, two or more of the amino acids are substituted with sarcosine.

TABLE 2

| Peptide Name | Peptide Amino Acid Sequence | SEQ ID NO |
|---|---|---|
| PA | IALILEPICCQERAA | SEQ ID NO: 3 |
| PA-I1Sar | (Sar)ALILEPICCQERAA | SEQ ID NO: 4 |
| PA-A2Sar | I(Sar)LILEPICCQERAA | SEQ ID NO: 5 |
| PA-L3Sar | IA(Sar)ILEPICCQERAA | SEQ ID NO: 6 |
| PA-I4Sar | IAL(Sar)LEPICCQERAA | SEQ ID NO: 7 |

TABLE 2-continued

| Peptide Name | Peptide Amino Acid Sequence | SEQ ID NO |
|---|---|---|
| PA-L5Sar | IALI(Sar)EPICCQERAA | SEQ ID NO: 8 |
| PA-E6Sar | IALIL(Sar)PICCQERAA | SEQ ID NO: 9 |
| PA-P7Sar | IALILE(Sar)ICCQERAA | SEQ ID NO: 10 |
| PA-I8Sar | IALILEP(Sar)CCQERAA | SEQ ID NO: 11 |
| PA-C9Sar | IALILEPI(Sar)CQERAA | SEQ ID NO: 12 |
| PA-C10Sar | IALILEPIC(Sar)QERAA | SEQ ID NO: 13 |
| PA-Q11Sar | ALILEPICC(Sar)ERAA | SEQ ID NO: 14 |
| PA-E12Sar | IALILEPICCQ(Sar)RAA | SEQ ID NO: 15 |
| PA-R13Sar | IALILEPICCQE(Sar)AA | SEQ ID NO: 16 |
| PA-A14Sar | IALILEPICCQER(Sar)A | SEQ ID NO: 17 |
| PA-A15Sar | IALILEPICCQERA(Sar) | SEQ ID NO: 18 |

PEGylation

Polyethylene glycol (PEG) is an oligomer or polymer of ethylene oxide. Disclosed herein are peptide compounds that are PEGylated (i.e. have one or more PEG moieties attached). PEGylation can be used to identify a modified peptide that retains complement inhibiting activity and is soluble in water. One or more PEG moieties can be attached to the N terminus of the peptide, the C terminus of the peptide, or to both the N and C terminus of the peptide. The PEGylated peptide compound includes any of the peptides described herein (Tables 1-4) wherein the peptide is modified through PEGylation of the N terminus, the C terminus, or both the N terminus and C terminus.

PEGylation was used to attach one or more PEG moieties to the N terminus, the C terminus, or both the N terminus and C terminus of PA (TABLE 3). In one or more embodiments, 24 PEG moieties are attached to the N terminus of PA. In one or more embodiments, 24 PEG moieties are attached to the C terminus of PA. In one or more embodiments, 24 PEG moieties are attached to the N terminus of PA and to the C terminus of PA. In one or more embodiments, 2, 3, 4, 5, 6, 7, 8, 9, 10, 11, 12, 13, 14, 15, 16, 17, 18, 19, 20, 21, 22, 23, 24, or more PEG moieties are attached to the N terminus of PA. In one or more embodiments, 2, 3, 4, 5, 6, 7, 8, 9, 10, 11, 12, 13, 14, 15, 16, 17, 18, 19, 20, 21, 22, 23, or 24 PEG moieties were attached to the C terminus of PA. In one or more embodiments, 2, 3, 4, 5, 6, 7, 8, 9, 10, 11, 12, 13, 14, 15, 16, 17, 18, 19, 20, 21, 22, 23, 24, or more PEG moieties are attached to both the N terminus and the C terminus of PA.

Disclosed herein are PEGylated peptide compounds. This application discloses synthetic peptides comprising the sequence of SEQ ID NO: 3 (PIC1), wherein one or more PEG moieties are attached, and wherein the peptides regulate complement activation and/or have anti-microbial activity.

TABLE 3

| Peptide Name | Peptide Amino Acid Sequence | SEQ ID NO |
|---|---|---|
| dPEG24-PA-dPEG24 | dPEG24-IALILEPICCQERAA-dPEG24 | SEQ ID NO: 19 |
| dPEG24-PA | dPEG24-IALILEPICCQERAA | SEQ ID NO: 20 |
| PA-dPEG24 | IALILEPICCQERAA-dPEG24 | SEQ ID NO: 21 |
| PA-dPEG20 | IALILEPICCQERAA-dPEG20 | SEQ ID NO: 22 |
| PA-dPEG16 | IALILEPICCQERAA-dPEG16 | SEQ ID NO: 23 |
| PA-dPEG12 | IALILEPICCQERAA-dPEG12 | SEQ ID NO: 24 |
| PA-dPEG08 | IALILEPICCQERAA-dPEG08 | SEQ ID NO: 25 |
| PA-dPEG06 | IALILEPICCQERAA-dPEG06 | SEQ ID NO: 26 |
| PA-dPEG04 | IALILEPICCQERAA-dPEG04 | SEQ ID NO: 27 |
| PA-dPEG03 | IALILEPICCQERAA-dPEG03 | SEQ ID NO: 28 |
| PA-dPEG02 | IALILEPICCQERAA-dPEG02 | SEQ ID NO: 29 |

PEGylation of Peptides in Combination with Amino Acid Substitutions

This application discloses PA/PIC1 that has been modified by a combination of sarcosine substitutions and/or alanine substitutions and/or PEGylation. A series of peptide substitutions and modifications of PA are disclosed, as shown in TABLE 4 below. The modified and substituted peptides can be used to identify a peptide that retains complement inhibiting activity and is soluble in water. This application discloses a synthetic peptide comprising the sequence of SEQ ID NO: 3, wherein one or more of the amino acids are substituted with sarcosine or alanine, wherein the peptides regulate complement activation and/or has anti-microbial activity. This application also discloses a synthetic peptide comprising the sequence of SEQ ID NO: 3, wherein one or more of the amino acids are substituted with sarcosine or alanine and one or more PEG moieties is attached to the N terminus of the peptides, the C terminus of the peptides, or to both the N and C terminus of the peptides, wherein the peptides regulate complement activation and/or have anti-microbial activity.

In one or more embodiments, two or more of the amino acids are substituted with sarcosine. In one or more embodiments, two or more of the amino acids are substituted with alanine. In one or more embodiments, one or more of the amino acids are substituted with sarcosine and one or more of the amino acids are substituted with alanine. The substituted peptides can further be modified by PEGylation as described above.

TABLE 4

| Peptide Name and Controls | Peptide Amino Acid Sequence | SEQ ID NO |
|---|---|---|
| Water | — | |
| DMSO | — | |

TABLE 4-continued

| Peptide Name and Controls | Peptide Amino Acid Sequence | SEQ ID NO |
|---|---|---|
| PA-dPEG24 | IALILEPICCQERAA-dPEG24 | SEQ ID NO: 21 |
| PA-C9SarC10A | IALILEPI(Sar)AQERAA | SEQ ID NO: 30 |
| PA-C9SarD10 | IALILEPI(Sar)QERAA | SEQ ID NO: 31 |
| PA-P7SarC9Sar | IALILE(Sar)I(Sar)CQERAA | SEQ ID NO: 32 |
| PA-E6Sar-dPEG24 | IALIL(Sar)PICCQERAA-dPEG24 | SEQ ID NO: 33 |
| PA-Q11Sar-dPEG24 | IALILEPICC(Sar)ERAA-dPEG24 | SEQ ID NO: 34 |
| PA-R13Sar-dPEG24 | IALILEPICCQE(Sar)AA-dPEG24 | SEQ ID NO: 35 |
| PA-A14Sar-dPEG24 | IALILEPICCQER(Sar)A-dPEG24 | SEQ ID NO: 36 |
| E6SarP7Sar | IALIL(Sar)(Sar)ICCQERAA | SEQ ID NO: 37 |
| E6SarC9Sar | IALIL(Sar)PI(Sar)CQERAA | SEQ ID NO: 38 |
| Q11SarP7Sar | IALILE(Sar)ICC(Sar)ERAA | SEQ ID NO: 39 |
| Q11SarC9Sar | IALILEPI(Sar)C(Sar)ERAA | SEQ ID NO: 40 |
| R13SarP7Sar | IALILE(Sar)ICCQE(Sar)AA | SEQ ID NO: 41 |
| R13SarC9Sar | IALILEPI(Sar)CQE(Sar)AA | SEQ ID NO: 42 |
| A14SarP7Sar | IALILE(Sar)ICCQER(Sar)A | SEQ ID NO: 43 |
| A14SarC9Sar | IALILEPI(Sar)CQER(Sar)A | SEQ ID NO: 44 |
| E6AE12A-dPEG24 | IALILAPICCQARAA-dPEG24 | SEQ ID NO: 45 |
| E6AE12AC9Sar | IALILAPI(Sar)CQARAA | SEQ ID NO: 46 |
| E6AE12AP7Sar | IALILA(Sar)ICCQARAA | SEQ ID NO: 47 |

Antimicrobial Activity of PIC1 Peptides

There is currently a critical need for new antibiotics as many microorganisms have become resistant to currently prescribed antibiotics. Additionally, most antibiotics are derived from other microbial organisms that bacteria have competed against for space and energy over the millennia, leading to rapid and predictable emergence of resistance.

The CP1 peptide was initially identified by its weak homology to the human neutrophil defensing peptide 1 (HNP-1). In addition to inhibiting complement activation, HNP-1 has the ability to inhibit bacterial growth. The PIC1 peptides described herein, including SEQ ID NOs: 3-47, are very different in amino acid sequence to HNP-1 and have no known homologs in nature. Surprisingly, in some aspects, the PIC1 peptides have anti-bacterial activity.

In some aspects, the disclosed peptide compounds have a direct antimicrobial effect and are, thus, ideal for inhibiting the growth of bacterial diseases. The disclosed peptide compounds can be used to prevent and treat diseases mediated by bacteria. In some embodiments, the disclosed peptide compounds can be used to prevent and treat Gram positive and Gram negative bacterial infections. In some embodiments, the disclosed peptide compounds can be used to prevent and treat, for example, *Pseudomonas aeruginosa*, MRSA, and carbapenemase-resistant enterobacteriacea (CREs) (e.g. resistant *Klebsiella pneumonia*). The disclosed peptide compounds can be used to prevent and treat bacterial vaginosis and vaginitis. In one or more embodiments, the disclosed peptide compounds kill the causative organism of bacterial vaginosis and also blocks the inflammation, which disrupts barrier defenses increasing risk of HIV transmission. As the PIC1 peptides have no homology with known proteins or peptides, this has the potential to decrease the likelihood of emergence of resistance.

The disclosed peptide compounds can also enhance growth of *Lactobacillus*. In some embodiments of the invention, *L. acidophilus* and *L. leichmannii* are enhanced by the disclosed peptide compounds. In certain aspects, the invention provides a method of enhancing *Lactobacillus* growth by administering a therapeutically effective amount of at least one synthetic peptide selected from the group consisting of SEQ ID NOS: 3-47.

Bacterial vaginosis and vaginitis are currently treated with systemic antibiotics. The disclosed peptide compounds can be used to prevent and treat bacterial vaginosis and vaginitis by local administration (e.g., topical administration) or by systemic administration (e.g., intravenous administration).

In certain aspects, the invention provides a method of treating a bacterial infection comprising administering to a subject a pharmaceutical composition comprising a therapeutically effective amount of a synthetic peptide comprising the amino acid sequence and modifications selected from SEQ ID NOs: 3-47. In one or more embodiments, the bacteria are *Staphylococcus aureus, Klebsiella pneumonia,*

*Pseudomonas aeruginosa, Neisseria gonorrhoeae, Chlamydia trachomatis,* or *Gardnerella* sp. In one or more embodiments, the subject has cystic fibrosis, and the peptide compounds treat cystic fibrosis. In one or more embodiments, the subject has gonorrhea or *Chlamydia*, and the peptide compounds treat gonorrhea or *Chlamydia*. In one or more embodiments, the subject has pneumonia, and the peptide compounds treat pneumonia.

In certain aspects, the invention provides a method of treating bacterial vaginitis comprising administering to a subject a pharmaceutical composition comprising a therapeutically effective amount of a synthetic peptide comprising the amino acid sequence and modifications selected from SEQ ID NOs: 3-47.

The Complement System and Diseases Associated with its Dysregulation

While complement is a vital host defense against microorganisms such as bacteria and some enveloped viruses, its unchecked activation can cause devastating host cell damage. Host tissue damage mediated by complement has been implicated in a wide variety of diseases, including autoimmune pathologies such as: rheumatoid arthritis, systemic lupus erythematosus, multiple sclerosis, myasthenia gravis, autoimmune hemolytic anemia, membranoproliferative glomerulonephritis, and serum sickness. It has also been identified as contributing to the development of the following diseases: Adult Respiratory Distress Syndrome (ARDS), ischemia-reperfusion injuries (including stroke and myocardial infarction), allo- and xeno-transplantation complications (including hyperacute rejection and graft versus host disease (GVHD), Alzheimer's disease, burn injuries, hemodialysis damage, cardiopulmonary bypass damage, and paroxysmal nocturnal hemoglobinuria (PNH).

Hereditary angioedema (HAE) is a rare genetic disorder caused by reduced levels of or non-functional C1-inhibitor; symptoms of HAE include acute edema. C1-inhibitor naturally regulates C1 activation, and treatment of acute edema requires substantial infusion of C1-inhibitor or plasma transfusion. Because astrovirus CP functionally blocks C1 activation, using the disclosed peptide compounds to treat HAE fulfills a therapeutic need because C1-inhibitor has to be purified from human sera from multiple subjects and, therefore, could be contaminated with human blood-borne pathogens. Therapeutic administration of the disclosed peptide compounds regulates C1 either in adjunct therapy with C1-inhibitor or as a stand-alone therapeutic treatment.

The disclosed peptide compounds can selectively regulate C1q and MBL activation without affecting alternative pathway activity and are, thus, ideal for preventing and treating diseases mediated by the dysregulated activation of the classical and lectin pathways. Specific blockade of classical and lectin pathways are particularly needed, as both of these pathways have been implicated in ischemia-reperfusion induced injury in many animal models. [Castellano et al., "*Therapeutic targeting of classical and lectin pathways of complement protects from ischemia-reperfusion-induced renal damage*." Am J Pathol. 2010; 176(4):1648-59; Lee et al., "*Early complement factors in the local tissue immunocomplex generated during intestinal ischemia/reperfusion injury*." Mol. Immunol. 2010 February; 47(5): 972-81; Tjernberg, et al., "*Acute antibody-mediated complement activation mediates lysis of pancreatic islets cells and may cause tissue loss in clinical islet transplantation*." Transplantation. 2008; April 27; 85(8):1193-9; Zhang et al. "*The role of natural IgM in myocardial ischemia-reperfusion injury*." J Mol Cell Cardiol. 2006 July; 41(1):62-7). The alternative pathway is essential for immune surveillance against invading pathogens, and humans with alternative pathway defects suffer severe bacterial infections. By binding and inactivating C1q and MBL, the peptide compounds can efficiently regulate classical and lectin pathway activation while leaving the alternative pathway intact.

The term "regulate," as used herein, refers to i) controlling, reducing, inhibiting or regulating the biological function of an enzyme, protein, peptide, factor, byproduct, or derivative thereof, either individually or in complexes; ii) reducing the quantity of a biological protein, peptide, or derivative thereof, either in vivo or in vitro; or iii) interrupting a biological chain of events, cascade, or pathway known to comprise a related series of biological or chemical reactions. The term "regulate" may thus be used, for example, to describe reducing the quantity of a single component of the complement cascade compared to a control sample, reducing the rate or total amount of formation of a component or complex of components, or reducing the overall activity of a complex process or series of biological reactions, leading to such outcomes as cell lysis, formation of convertase enzymes, formation of complement-derived membrane attack complexes, inflammation, or inflammatory disease. In an in vitro assay, the term "regulate" may refer to the measurable change or reduction of some biological or chemical event, but the person of ordinary skill in the art will appreciate that the measurable change or reduction need not be total to be "regulatory."

In one or more aspects, the disclosed peptide compounds can be used to treat an inflammatory disease. In one or more embodiments, the disclosed peptide compounds can be used to treat an autoimmune disease. In one or more embodiments, the disclosed peptide compounds can be used to treat hemolytic transfusion reactions, cold-agglutinin disease, immune-complex diseases (e.g. serum sickness), thalassemia, sickle cell disease, ABO incompatibility (e.g. neonatal jaundice), acute/hyperacute solid organ transplantation rejection, solid organ transplantation warm/cold ischemia, instant blood-mediated inflammatory reaction (IBMIR), systemic lupus erythematosus (SLE), rheumatoid arthritis, ischemia-reperfusion injury, myocardial infarct, stroke, hypoxic ischemic encephalopathy (e.g. birth asphyxia brain injury), traumatic brain injury, coronary artery bypass surgery, cystic fibrosis, wound healing, cancer, Alzheimer's disease, Parkinson's disease, paroxysmal nocturnal hemoglobinuria (PNH), atypical hemolytic uremic syndrome (aHUS), asthma, chronic obstructive pulmonary disease (COPD), Crohn's disease, Sepsis syndrome/ARDS/SIRS, glomerulonephritis (e.g. lupus nephritis, anti-glomerular basement membrane disease, anti-neutrophil cytoplasmic autoantibody-induced, membranoproliferative glomerulonephritis (e.g. dense deposit disease), membranous nephropathy), IgA nephropathy, or C3 glomerulopathy.

Complement-Mediated Acute Intravascular Hemolytic Transfusion Reaction (AIHTR)

Acute intravascular hemolytic transfusion reaction ("ATR," "AHTR," or "AIHTR") is a type of transfusion reaction that is associated with hemolysis. AIHTR can result in complement mediated lysis and rapid destruction of donor red blood cells. AIHTRs have a broad clinical presentation from mild and transitory signs and symptoms to serious cases of shock, disseminated intravascular coagulation, renal failure and death.

The American Red Cross estimates that 30 million blood components are transfused every year in the United States (US) [Barbee I. Whitaker PSH, PhD, The 2011 National Blood Collection and Utilization Survey Report; 2011]. Approximately 70,000 US patients living with sickle cell disease and 1.6 million individuals diagnosed with cancer require blood transfusions routinely as part of their disease management. Blood transfusions are life-saving, but carry the risk of a variety of reactions some of which are potentially life-threatening such as acute intravascular hemolytic transfusion reactions (AIHTRs) (Murphy M F, Waters J H, Wood E M, Yazer M H. "Transfusing blood safely and appropriately." BMJ. 2013; 347:f4303]. AIHTR is estimated to occur in one-fifth of total transfusions (Refaai M A, Blumberg N. "The transfusion dilemma—weighing the known and newly proposed risks of blood transfusions against the uncertain benefits." *Best practice & research Clinical anaesthesiology.* 2013; 27(1):17-35). Individuals receiving frequent blood transfusions will develop alloantibodies and autoantibodies to red blood cell (RBC) antigens over time making cross-matching increasingly difficult and thus increasing the risk of AIHTR (Aygun B, Padmanabhan S, Paley C, Chandrasekaran V. "Clinical significance of RBC alloantibodies and autoantibodies in sickle cell patients who received transfusions." *Transfusion.* 2002; 42(1):37-43]. Current transfusion safe-guards include 'typing', 'antibody screening' as well as 'cross matching', and while these measures have made transfusions safer than ever before, transfusion reactions still occur (Osterman J L, Arora S. "Blood product transfusions and reactions." *Emergency medicine clinics of North America.* 2014; 32(3):727-738]. AIHTR occurs when host antibodies bind to the transfused erythrocytes initiating classical complement pathway activation leading to the generation of the inflammatory mediators C3a and C5a as well as C3b opsonization and hemolysis of the transfused cells via the membrane attack complex (MAC) (Stowell S R, Winkler A M, Maier C L, et al. "Initiation and regulation of complement during hemolytic transfusion reactions." *Clinical & developmental immunology.* 2012; 2012:307093]. While the role of complement in AIHTR is well recognized, to date, only one case has been reported describing clinical intervention of an AIHTR by inhibiting generation of the complement anaphylatoxins C3a and C5a [Weinstock C, Mohle R, Dorn C, et al. "Successful use of eculizumab for treatment of an acute hemolytic reaction after ABO-incompatible red blood cell transfusion." *Transfusion.* 2015; 55(3):605-610].

The classical pathway of complement acts as an amplification cascade after initial activation of complement complex C1 by antibodies (Frank M M A J ed Complement system. In: Austen K F, Atkinson J P, Cantor H I ed. Samter's Immunologic Disease. New York: Lippincott Williams and Wilkins; 2001]. The C1 complex consists of the pattern recognition molecule C1q and the serine protease tetramer C1r-C1s-C1s-C1r. Upon binding of C1q to IgM or clustered IgG antibodies, C1q undergoes a conformational change to activate C1r-C1s-C1s-C1r and initiate classical pathway-mediated complement activation. The Peptide Inhibitor of Complement C1 (PIC1) described herein is a peptide inhibitor of the classical pathway of complement (Mauriello C T, Pallera H K, Sharp J A, et al. "A novel peptide inhibitor of classical and lectin complement activation including ABO incompatibility." *Mol Immunol.* 2013; 53(1-2):132-139; Sharp J A, Whitley P H, Cunnion K M, Krishna N K. "Peptide inhibitor of complement C1, a novel suppressor of classical pathway activation: mechanistic studies and clinical potential." *Front Immunol.* 2014; 5:406; Gronemus J Q, Hair P S, Crawford K B, Nyalwidhe J O, Cunnion K M, Krishna N K. "Potent inhibition of the classical pathway of complement by a novel C1q-binding peptide derived from the human astrovirus coat protein."*Mol Immunol.* 2010; 48(1-3):305-313). PIC1 inhibits antibody-initiated activation of C1 by binding C1q and preventing activation of C1r-C1s-C1s-C1r12. PIC1 also has also been shown to inhibit classical complement pathway-mediated ABO incompatible hemolysis of human erythrocytes in vitro (Mauriello C T, Pallera H K, Sharp J A, et al. "A novel peptide inhibitor of classical and lectin complement activation including ABO incompatibility." *Mol Immunol.* 2013; 53(1-2):132-139; Sharp J A, Whitley P H, Cunnion K M, Krishna N K. "Peptide inhibitor of complement C1, a novel suppressor of classical pathway activation: mechanistic studies and clinical potential." *Front Immunol* 2014; 5:406; Shah T A, Mauriello C T, Hair P S, et al. "Complement inhibition significantly decreases red blood cell lysis in a rat model of acute intravascular hemolysis." *Transfusion.* 2014). When the aqueous polyethylene glycol (PEG)-conjugated version of the PIC1, PA-dPEG24 (SEQ ID NO: 21), described herein is administered intravascularly into rats, it can achieve greater than 90% systemic inhibition of the animal's serum complement levels within 30 seconds (Sharp J A, Whitley P H, Cunnion K M, Krishna N K. "Peptide inhibitor of complement C1, a novel suppressor of classical pathway activation: mechanistic studies and clinical potential." *Front Immunol.* 2014; 5:406]. The ability of PIC1 to inhibit complement activation makes it an ideal molecule to block the rapid complement-mediated hemolysis that typifies AIHTR.

A rat AIHTR disease model based on xenotransfusion of human RBCs was established (Shah T A, Mauriello C T, Hair P S, et al. "Complement inhibition significantly decreases red blood cell lysis in a rat model of acute intravascular hemolysis." *Transfusion.* 2014]. Wistar rats have natural hemagglutinins in their serum that will bind to human AB erythrocytes (Shah et al; Aptekman P M, Bogden A E. "Characterization of the natural hemagglutinins in normal rat serum associated with a negative phase following tumor implantation." *Cancer Research.* 1956; 16(3):216-221). Upon transfusion of human erythrocytes, they will produce a rapid ABO incompatibility-like hemolysis via antibody-initiated classical complement pathway activation (Yazdanbakhsh K, Kang S, Tamasauskas D, Sung D, Scaradavou A. "Complement receptor 1 inhibitors for prevention of immune-mediated red cell destruction: potential use in transfusion therapy." *Blood.* 2003; 101(12):5046-50521.

PIC1 peptides, including PA (SEQ ID NO: 3) and PA-dPEG24 (SEQ ID NO: 21), can block complement-mediated lysis of AB human red blood cells (RBC) by O serum in vitro. This assay mimics ABO incompatibility. PA-dPEG24 has efficacy in a rodent model of AIHTR demonstrating inhibition of human RBC lysis in a prevention and rescue scenario. Thus PIC1 peptides can be used in the treatment of transfusion reactions in humans for which no current therapy exists.

Current blood banking organization or transfusion medicine practice does not have a method to directly evaluate risk for complement mediated RBC lysis between donor and recipient. The disclosed peptide compounds can be used as a diagnostic tool. The disclosed peptide compounds can also be used as a prophylactic treatment to prevent AIHTR or as a rescue treatment during an AIHTR has significant clinical implications. The disclosed peptide compounds can prevent the high concentrations of free hemoglobin that cause acute kidney injury in AIHTR. There are currently no therapies for ATRs other than supportive care.

The disclosed peptide compounds can be used to detect complement-mediated lysis of RBCs and are thus ideal for discriminating if an erythrocyte transfusion may cause AIHTR. The disclosed peptide compounds can be used to predict AIHTR.

In certain aspects, the invention provides a method of treating acute transfusion reaction comprising administering to a subject a pharmaceutical composition comprising a therapeutically effective amount of a synthetic peptide comprising the amino acid sequence and modifications selected from SEQ ID NOs: 3-47. In one or more embodiments, the pharmaceutical composition is administered before the subject is administered a blood transfusion. In one or more embodiments, the pharmaceutical composition is administered after the subject is administered a blood transfusion. In one or more embodiments, the pharmaceutical composition is administered before and after the subject is administered a blood transfusion.

Complement Effectors in Cystic Fibrosis (CF)

In cystic fibrosis (CF), lung damage is believed to be mediated by a cycle of obstruction, infection, and inflammation. It has been determined that complement effectors are elevated in the lung fluids of CF patients compared to normal controls.

Cystic fibrosis (CF) afflicts 30,000 individuals in the United States (Boyle M P. "Adult cystic fibrosis." *JAMA* 2007; 298(15):1787-93) with respiratory failure causing the majority of deaths. Progressive destruction of lung parenchyma is mediated by a cycle of obstruction, infection with bacterial pathogens, and inflammation (Rowe S M, Miller S, Sorscher E J, "Cystic fibrosis." *N Engl J Med* 2005; 352 (19):1992-2001). As the cycle repeats there is progression from lung damage to lung scarring and finally pulmonary failure (Gibson R L, Burns J L, Ramsey B W. "Pathophysiology and management of pulmonary infections in cystic fibrosis."*Am J Respir Crit Care Med* 2003; 168(8):918-51].

Figure 9:
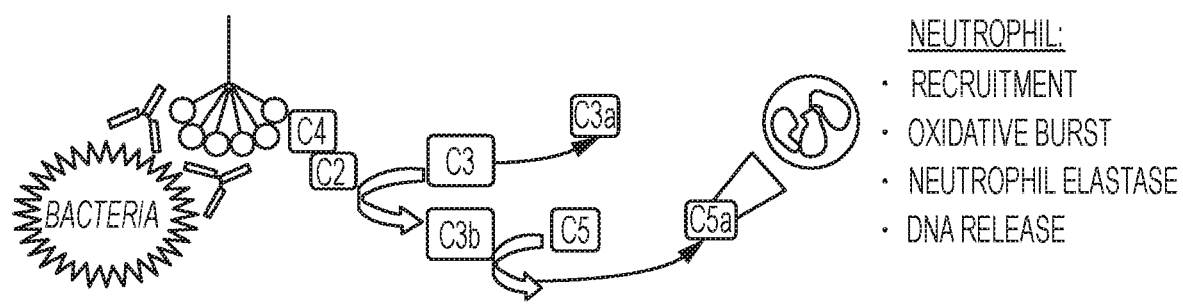
FIG. 9 shows bacteria initiating classical pathway complement activation with C5a-mediated neutrophil recruitment and activation.

The most destructive inflammatory cascade in the human body is the complement system, which contributes to host tissue damage in numerous inflammatory disease processes (Ricklin D, Lambris J D. "Complement-targeted therapeutics." *Nat Biotechnol* 2007; 25(11):1265-75). Recent evidence has shown that complement proteins are major constituents of lung fluid in CF patients and normal humans, where C3 and C4 account for two of the four most prevalent proteins (Gharib S A, Vaisar T, Aitken M L, et al. "Mapping the lung proteome in cystic fibrosis." *J Proteome Res* 2009; 8(6):3020-8). This suggests that complement may play a much larger role in CF lung inflammation than what has been previously suspected. Antibody binding to bacteria can activate the classical complement pathway via the initiating component C1 (FIG. 9). C4 is a cascade component for the classical (i.e. antibody initiated) pathway leading to formation of the opsonin C4b and downstream activation of C3 (Lambris J D, Sahu A, Wetsel R A. "The chemistry and biology of C3, C4, and C5." In: Volanakis J E, Frank M M, (eds). *The human complement system in health and disease.* New York: Marcel Dekker; 1998, 83-118.). C3 is the central complement component, which upon activation generates the complement effector C3a and covalently binds cells with the opsonic fragments C3b and iC3b. C3b then initiates activation of C5, generating the extremely potent anaphylatoxin C5a. C5a is among the most powerful stimulants for neutrophil migration and activation, leading to oxidative burst and degranulation (Lambris J D, Sahu A, Wetsel R A. "The chemistry and biology of C3, C4, and C5." In: Volanakis J E, Frank M M, (eds). *The human complement system in health and disease.* New York: Marcel Dekker; 1998, 83-118; Tralau T, Meyer-Hoffert U, Schroder J M, et al. "Human leukocyte elastase and cathepsin G are specific inhibitors of C5a-dependent neutrophil enzyme release and chemotaxis." *Exp Dermatol* 2004; 13(5):316-25). Neutrophil death, which follows degranulation, is a major source of the viscous DNA that contributes to the obstruction of airways in the CF lung (Dwyer M, Shan Q, D'Ortona S, et al. "Cystic Fibrosis Sputum DNA Has NETosis Characteristics and Neutrophil Extracellular Trap Release Is Regulated by Macrophage Migration-Inhibitory Factor." *J Innate Immun* 2014; Hodson M E. "Aerosolized dornase alfa (rhDNase) for therapy of cystic fibrosis." *Am J Respir Crit Care Med* 1995; 151(3 Pt 2): S70-4]. Among the neutrophil granule products released is neutrophil elastase, which is a major contributor to parenchymal lung damage in CF (Gifford A M, Chalmers J D. "The role of neutrophils in cystic fibrosis." *Curr Opin Hematol* 2014; 21(1):16-22; Le Gars M, Descamps D, Roussel D, et al. "Neutrophil elastase degrades cystic fibrosis transmembrane conductance regulator via calpains and disables channel function in vitro and in vivo." *Am J Respir Crit Care Med* 2013; 187(2):170-9; Sagel S D, Wagner B D, Anthony M M, et al. "Sputum biomarkers of inflammation and lung function decline in children with cystic fibrosis." *Am J Respir Crit Care Med* 2012; 186(9):857-65]. Thus, complement activation may play a significant role in neutrophil recruitment and activation in CF lungs, contributing to tissue damage. Additional properties of C5a that may also contribute to CF lung disease are stimulation of histamine release, enhancement of vascular permeability, and inducement of smooth muscle contraction (Lambris J D, Sahu A, Wetsel R A. "The chemistry and biology of C3, C4, and C5." In: Volanakis J E, Frank M M, (eds). *The human complement system in health and disease.* New York: Marcel Dekker; 1998, 83-11]. The known inflammatory properties of C5a are consistent with the increasing evidence of the role of C5a in inflammatory lung diseases (Schmudde I, Strover H A, Vollbrandt T, et al. "C5a receptor signalling in dendritic cells controls the development of maladaptive Th2 and Th17 immunity in experimental allergic asthma."*Mucosal Immunol* 2013; 6(4): 807-25; Bosmann M, Ward P A. "Role of C3, C5 and anaphylatoxin receptors in acute lung injury and in sepsis." *Adv Exp Med Biol* 2012; 946:147-59], including acute lung injury. Thus, although not bound by any theory, multiple lines of reasoning suggest that complement-mediated inflammation may be a major contributor to inflammatory lung damage in CF.

Some investigation into the potentially important role of C5a in the CF lung has been performed. In 1986, Fick et al. described the presence of increased amounts of C5a, measured by radioimmunoassay in the bronchoalveolar lavage (BAL) of nine CF patients with clinically stable lung disease compared with BAL from healthy controls. (Fick R B, Jr., Robbins R A, Squier S U, et al. "Complement activation in cystic fibrosis respiratory fluids: in vivo and in vitro generation of C5a and chemotactic activity." *Pediatr Res* 1986; 20(12):1258-68). The CF BAL fluids were chemotactic for neutrophils, which appeared to correlate with C5a concentrations. The BAL fluids showed evidence of prior complement activation by the presence of C3c, assayed by crossed-immunoelectrophoresis. Two CF patients with the lowest C5a measurements were noted to have normal $FEV_1$ and FVC measurements, suggesting a potential association with lung damage. However, no further studies were then performed to test whether C5a concentrations in CF lung fluid correlate with either acute lung exacerbations or chronic lung disease progression in CF.

Although not bound by any mechanism, the disclosed peptide compounds can selectively regulate C1q and MBL activation without affecting alternative pathway activity and are, thus, ideal for treating cystic fibrosis. In one or more embodiments, the disclosed peptide compounds can be used to treat cystic fibrosis. In one or more embodiments, the disclosed peptide compounds can be used as anti-inflammatory and anti-microbial agents. In one or more embodiments, the disclosed peptide compounds can be used to treat cystic fibrosis by administrating the peptide(s) via nebulization directly into the lung. In one or more embodiments, administration of the disclosed peptide compound(s) via nebulization mitigates lung destruction caused by cystic fibrosis. The disclosed peptide compounds have clinical benefit for CF patients by slowing the progression of lung damage leading to increased life span and quality of life.

In certain aspects, the invention provides a method of treating cystic fibrosis comprising administering to a subject a pharmaceutical composition comprising a therapeutically effective amount of a synthetic peptide comprising an amino acid sequence and modifications selected from SEQ ID NOs: 3-47.

Modulation of C1q Interaction with C1q Receptors

C1q interactions with C1q receptors appear to play important roles in homeostatic functions such as scavenging of apoptotic cellular debris and immune complexes as well as T cell signaling through antigen presenting cells (macrophage and dendritic cells). Currently, no clinical pharmacological agents modulate the interaction of C1q with C1q receptors.

The disclosed peptide compounds can be used to block C1q binding to C1q receptors, including calreticulin/cC1qR. The ability of the disclosed peptide compounds to block binding of C1q to cellular receptors may have an important role in modulating intracellular signaling processes mediated by C1q binding to C1q receptors. The disclosed peptide compounds can be used to regulate the complement response in disease processes such as systemic lupus erythematosus and cancer.

Brain Damage in Birth Asphyxia

Complement activation is instrumental in the development of ischemia-reperfusion injuries such as neonatal hypoxic ischemic encephalopathy (HIE). Therapeutic hypothermia (HT) offers only an 11% reduction in death or disability. Published in vitro data has shown that HT paradoxically increase pro-inflammatory complement activation potentially limiting its benefit.

PIC1 peptides can reduce brain infarct volumes without prolonged systemic complement depletion. PIC1 peptides can be a useful adjunct to HT to improve neurological outcomes in HIE.

The disclosed peptide compounds can be us to prevent brain damage from birth asphyxia. The disclosed peptide compounds can also be used to prevent ischemia-reperfusion injury (IRI) in diseases such as myocardial infarct, coronary artery bypass surgery, stroke, etc. The disclosed peptide compounds can also be used to prevent hyperacute and acute solid organ transplantation rejection, which are classical complement pathway mediated events.

In certain aspects, the invention provides a method of treating birth asphyxia comprising administering to a subject a pharmaceutical composition comprising a therapeutically effective amount of a synthetic peptide comprising an amino acid sequence and modifications selected from SEQ ID NOs: 3-47. In some embodiments, the subject is further treated by therapeutic hypothermia.

In certain aspects, the invention provides a method of treating hypoxic ischemic encephalopathy comprising administering to a subject a pharmaceutical composition comprising a therapeutically effective amount of a synthetic peptide comprising an amino acid sequence and modifications selected from SEQ ID NOs: 3-47. In some embodiments, the subject is further treated by therapeutic hypothermia.

Myeloperoxidase (MPO) Activity

Myeloperoxidase (MPO) is an enzyme from neutrophils that creates hypochlorite (bleach) in acute inflammation and damages invading and host cells alike. This enzyme is known to be destructive to host tissues in Cystic Fibrosis (CF) and Hypoxic Ischemic Encephalopathy (HIE).

In some embodiments, PIC1 blocked the enzymatic activity of MPO in the sputum of cystic fibrosis patients. In some embodiments, PIC1 blocked enzymatic activity in brain tissue from HIE patents. In some embodiments, MPO activity present in the lysates of purified human neutrophils can be directly inhibited by PIC1. In some embodiments, the invention demonstrates that PIC1 has anti-inflammatory activity against cystic fibrosis and HIE.

Autoimmune Hemolytic Anemia

The present disclosure provides peptide compounds capable of treating autoimmune hemolytic anemia. Autoimmune hemolytic anemia is a group of disorders characterized by a malfunction of the immune system that produces autoantibodies, which attack red blood cells as if they were substances foreign to the body. Autoimmune hemolytic anemia may be characterized by one or more of elevated serum bilirubin, excess urinary urobilinogen, reduced plasma haptoglobin, raised serum lactic dehydrogenase (LDH), hemosiderinuria, methemalbuminemia, spherocytosis, reticulocytosis, and/or erythroid hyperplasia of the bone marrow. In certain aspects of the invention, treating autoimmune hemolytic anemia comprises administering a peptide compounds selected from the group consisting of SEQ ID NO: 3-47.

Pharmaceutical Formulation and Administration

The present disclosure provides pharmaceutical compositions capable of regulating the complement system, comprising at least one peptide compound, as discussed above, and at least one pharmaceutically acceptable carrier, diluent, stabilizer, or excipient. Pharmaceutically acceptable carriers, excipients, or stabilizers are nontoxic to recipients at the dosages and concentrations employed. They can be solid, semi-solid, or liquid. The pharmaceutical compositions of the present invention can be in the form of tablets, pills, powders, lozenges, sachets, cachets, elixirs, suspensions, emulsions, solutions, or syrups.

Some examples of pharmaceutically acceptable carriers, diluents, stabilizers, or excipients include: lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The pharmaceutical compositions of the present invention can be formulated using procedures known in the art to provide quick, normal, or sustained or delayed release of the active ingredient.

The disclosure relates to a method of regulating the complement system in a subject comprising administering to a subject the compositions described above. The pharmaceutical compositions of the present invention are prepared by mixing the peptide compound having the appropriate degree of purity with pharmaceutically acceptable carriers, diluents, or excipients. Examples of formulations and methods for preparing such formulations are well known in the art. The pharmaceutical compositions of the present invention are useful as a prophylactic and therapeutic agent for various disorders and diseases, as set forth above. In one embodiment, the composition comprises a therapeutically effective amount of the peptide compound. In another embodiment, the composition comprises at least one other active ingredient effective in treating at least one disease associated with complement-mediated tissue damage. The term "therapeutically effective amount," as used herein, refers to the total amount of each active component that is sufficient to show a benefit to the subject.

The therapeutically effective amount of the peptide compound varies depending on several factors, such as the condition being treated, the severity of the condition, the time of administration, the route of administration, the rate of excretion of the compound employed, the duration of treatment, the co-therapy involved, and the age, gender, weight, and condition of the subject, etc. One of ordinary skill in the art can determine the therapeutically effective amount. Accordingly, one of ordinary skill in the art may need to titer the dosage and modify the route of administration to obtain the maximal therapeutic effect.

The effective daily dose generally is within the range of from about 0.001 to about 200 milligrams per kilogram (mg/kg) of body weight, preferably about 80 to about 160 mg/kg, more preferably about 0.1 to about 20 mg/kg. This dose can be achieved through a 1-6 time(s) daily dosing regimen. Alternatively, optimal treatment can be achieved through a sustained release formulation with a less frequent dosing regimen.

Pharmaceutical formulations may be adapted for administration by any appropriate route, for example, by the oral, nasal, topical (including buccal, sublingual, or transdermal), or parenteral (including subcutaneous, intracutaneous, intramuscular, intraarticular, intraperitoneal, intrasynovial, intrasternal, intrathecal, intralesional, intravenous, or intradermal injections or infusions) route. For human administration, the formulations preferably meet sterility, pyrogenicity, general safety, and purity standards, as required by the offices of the Food and Drug Administration (FDA).

Combination Therapies

A further embodiment of the invention provides a method of preventing or treating a disease associated with complement-mediated tissue damage, comprising administering to a subject a pharmaceutical composition of the present invention. While the pharmaceutical compositions of the present invention can be administered as the sole active pharmaceutical agent, they can also be used in combination with one or more therapeutic or prophylactic agent(s) that is(are) effective for preventing or treating the disease. In this aspect, the method of the present invention comprises administrating a pharmaceutical composition of the present invention before, concurrently, and/or after one or more additional therapeutic or prophylactic agents effective in treating at least one disease associated with complement-mediated tissue damage.

For example, the pharmaceutical compositions of the present invention can be used to treat brain asphyxia or hypoxic ischemic encephalopathy, either alone or in combination with therapeutic hypothermia.

For example, the pharmaceutical compositions of the present invention can be used to treat rheumatoid arthritis, either alone or in combination with a non-steroidal anti-inflammatory agent (NSAID), a corticosteroid, or a disease modifying anti-rheumatic drug (DMARD).

Examples of NSAIDs include: salicylates (such as aspirin, amoxiprin, benorilate, choline magnesium salicylate, diflunisal, faislamine, methyl salicylate, magnesium salicylate, and salicyl salicylate (salsalate)), arylalkanoic acids (such as diclofenac, aceclofenac, acemetacin, bromfenac, etodolac, indometacin, ketorolac, nabumetone, sulindac, and tolmeti), 2-arylpropionic acids (such as ibuprofen, carprofen, fenbufen, fenoprofen, flurbiprofen, ketoprofen, loxoprofen, naproxen, tiaprofenic acid, and suprofen), N-arylanthranilic acids (such as mefenamic acid and meclofenamic acid), pyrazolidine derivatives (such as phenylbutazone, azapropazone, metamizole, oxyphenbutazone, and sulfinprazone), oxicams (such as piroxicam, lomoxicam, meloxicam, and tenoxicam), COX-2 inhibitors (such as etoricoxib, lumiracoxib, and parecoxib), sulphonanilides such as nimesulide, and others such as licofelone and omega-3 fatty acids.

Examples of corticosteroids include: triamcinolone (Aristocort®), cortisone (Cortone® Acetate Tablets), dexamethasone (Decadron® Elixir), prednisone (Deltasone®), and methylprednisolone (Medrol®).

Examples of DMARDs include: methotrexate (Rheumatrex®), leflunomide (Arava®), etanercept (Enbrel®), infliximab (Remicade®), adalimumab (Humira®), anakinra (Kineret®), sulfasalazine (Azulfidine EN-Tabs®), antimalarials, gold salts, d-penicillamine, cyclosporin A, cyclophosphamide and azathioprine.

Soliris™ (eculizumab) is a humanized anti-C5 monoclonal antibody. It has been approved by the FDA for the treatment of the rare form of hemolytic anemia, paroxysmal nocturnal hemoglobinuria. In one embodiment, the pharmaceutical compositions of the present invention can be used in combination with Soliris™ in treating paroxysmal nocturnal hemoglobinuria, atypical hemolytic uremic syndrome, heart disease, pulmonary diseases, autoimmune diseases, asthma, as well as the ancillary care of transplants.

The pharmaceutical compositions of the present invention can be administered with additional agent(s) in combination therapy, either jointly or separately, or by combining the pharmaceutical compositions and the additional agent(s) into one composition. The dosage is administered and adjusted to achieve maximal management of the conditions. For example, both the pharmaceutical compositions and the additional agent(s) are usually present at dosage levels of between about 10% and about 150%, more preferably, between about 10% and about 80%, of the dosage normally administered in a mono-therapy regimen.

EXAMPLES

The invention is further illustrated by the following examples, provided for illustrative purposes only. They are not to be construed as limiting the scope or content of the invention in any way.

Example 1: Solubility and Hemolytic Assay of Sarcosine (SAR) Substitution Peptides Methods: Hemolytic Assay.

Peptides were diluted to 0.77 mM in factor B-depleted human sera (Complement Technologies, Inc.) and incubated for 1 hour at 37° C. These peptides were then diluted with $GVBS^{++}$ to equal 2.5% serum, of which 0.25 ml was combined with 0.4 ml of $GVBS^{++}$ and 0.1 ml of sensitized sheep red blood cells (RBCs) and again incubated for 1 hour at 37° C. The procedure was stopped by the addition of 4.0 ml of $GVBS^{--}$ centrifuged for 5 minutes at 1,620×g, and the absorbance of the supernatants was read at 412 nm in a spectrophotometer. The percent lysis of each sample was standardized to that of the serum only control.

Results: Solubility of Sarcosine Substituted Peptides

TABLE 5 shows the solubility and hemolytic assay in factor B depleted serum of sarcosine (Sar) substitution peptides. The final concentration of peptide in factor B-depleted serum was 0.77 mM. Each peptide was evaluated in triplicate and the mean values are reported. Peptides not soluble in water were re-suspended in DMSO. In the hemolytic assay, soluble peptides are standardized to water and insoluble peptides standardized to DMSO.

412 nm in a spectrophotometer. The percent lysis of each sample was standardized to that of the serum only control.

Initially, PA was PEGylated with 24 PEG moieties on the N terminus (dPEG24-PA, SEQ ID NO: 20), on the C terminus (PA-dPEG24, SEQ ID NO: 21), or on both the N terminus and C terminus (dPEG24-PA-dPEG24, SEQ ID NO: 19). All three PEGylated peptides were soluble in water and showed varying degrees of complement inhibition with

TABLE 5

| Peptide Name and Controls | Peptide Amino Acid Sequence | SEQ ID NO | Solubility in water | Hemolysis (%) |
|---|---|---|---|---|
| Water | — | | - | 100.00 |
| GVBS++ | — | | - | 1.31 |
| DMSO | — | | - | 95.13 |
| PA | IALILEPICCQERAA | SEQ ID NO: 3 | No | 3.15 |
| PA-I1Sar | (Sar)ALILEPICCQERAA | SEQ ID NO: 4 | No | 84.49 |
| PA-A2Sar | I(Sar)LILEPICCQERAA | SEQ ID NO: 5 | Yes | 37.72 |
| PA-L3Sar | IA(Sar)ILEPICCQERAA | SEQ ID NO: 6 | Yes | 87.36 |
| PA-I4Sar | IAL(Sar)LEPICCQERAA | SEQ ID NO: 7 | Yes | 93.19 |
| PA-L5Sar | IALI(Sar)EPICCQERAA | SEQ ID NO: 8 | Yes | 85.13 |
| PA-E6Sar | IALIL(Sar)PICCQERAA | SEQ ID NO: 9 | No | 5.19 |
| PA-P7Sar | IALILE(Sar)ICCQERAA | SEQ ID NO: 10 | Yes | 3.01 |
| PA-I8Sar | IALILEP(Sar)CCQERAA | SEQ ID NO: 11 | Yes | 33.92 |
| PA-C9Sar | IALILEPI(Sar)CQERAA | SEQ ID NO: 12 | Yes | 5.63 |
| PA-C10Sar | IALILEPIC(Sar)QERAA | SEQ ID NO: 13 | No | 56.18 |
| PA-Q11Sar | ALILEPICC(Sar)ERAA | SEQ ID NO: 14 | No | 3.02 |
| PA-E12Sar | IALILEPICCQ(Sar)RAA | SEQ ID NO: 15 | No | 105.72 |
| PA-R13Sar | IALILEPICCQE(Sar)AA | SEQ ID NO: 16 | No | 3.42 |
| PA-A14Sar | IALILEPICCQER(Sar)A | SEQ ID NO: 17 | No | 3.88 |
| PA-A15Sar | IALILEPICCQERA(Sar) | SEQ ID NO: 18 | No | 21.68 |

Peptide derivatives PA-P7Sar (SEQ ID NO: 10) and PA-C9Sar (SEQ ID NO: 12) were both water soluble and inhibited complement activity to the same degree as the PA peptide (SEQ ID NO: 3). A dose-dependent inhibition of complement activity by both PA-P7Sar and PA-C9Sar in a hemolytic assays is shown in FIG. 1.

Example 2—Solubility and Hemolytic Assay of PEGylated PA Peptides

Methods: Hemolytic Assay.

Polar Assortant peptides were serially diluted in undiluted factor B-depleted human sera (Complement Technologies, Inc.) and incubated for 1 hour at 37° C. Water, GVBS++ and DMSO were included as controls. These peptides were then diluted with GVBS++ to equal 2.5% serum, of which 0.25 ml was combined with 0.4 ml of GVBS++ and 0.1 ml of sensitized sheep red blood cells (RBCs) and again incubated for 1 hour at 37° C. The procedure was stopped by the addition of 4.0 ml of GVBS-- centrifuged for 5 minutes at 1,620×g, and the absorbance of the supernatants was read at PA-dPEG24 (SEQ ID NO: 21) inhibiting complement activation to the same degree as PA (FIG. 2A).

Figure 3:
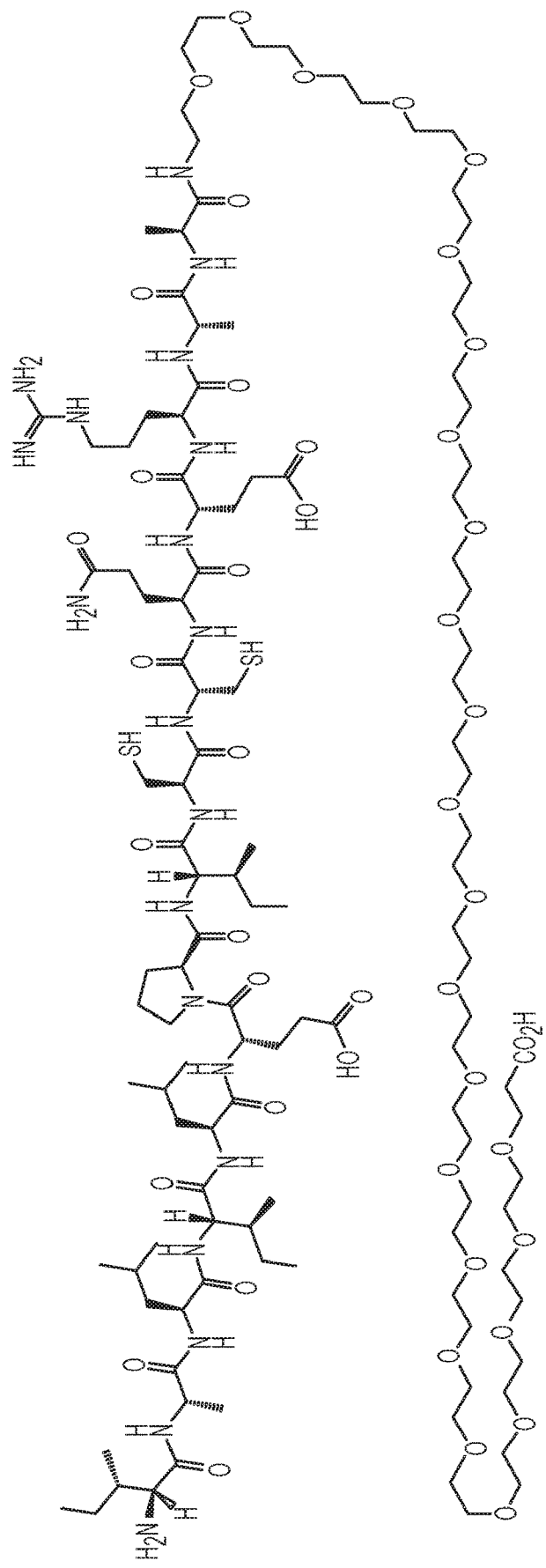
FIG. 3 shows the structure of PA-dPEG24 (SEQ ID NO: 21).
Figure 4A:
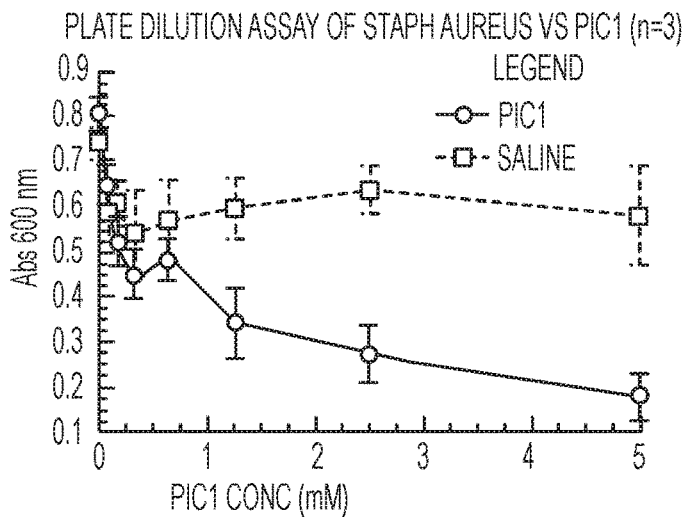
FIGS. 4A-E show plate dilution assays.
Figure 4B:
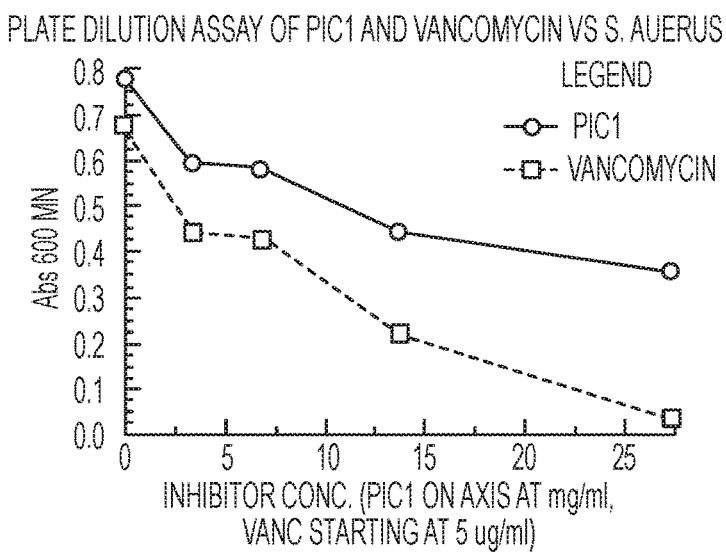
Figure 4C:
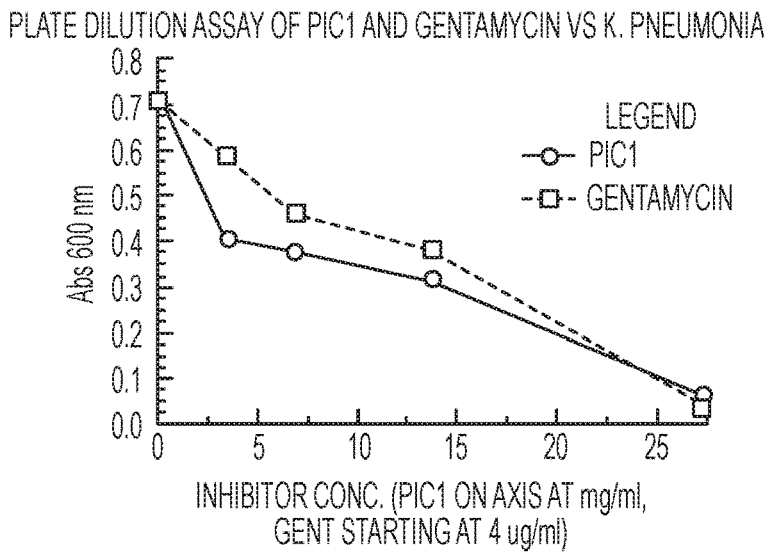
Figure 4D:
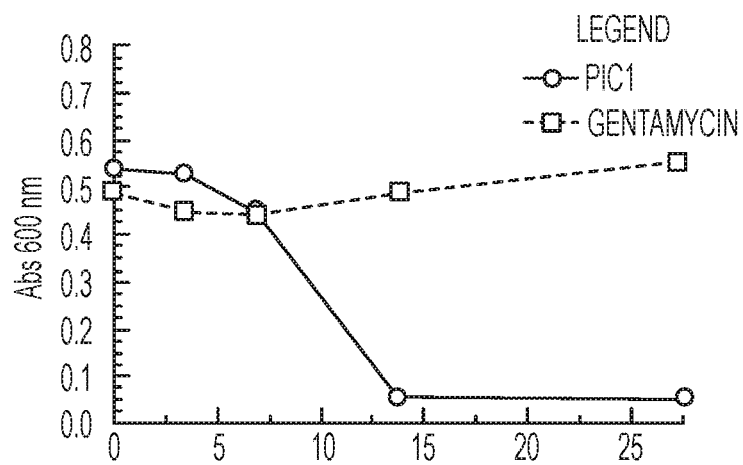
Figure 4E:
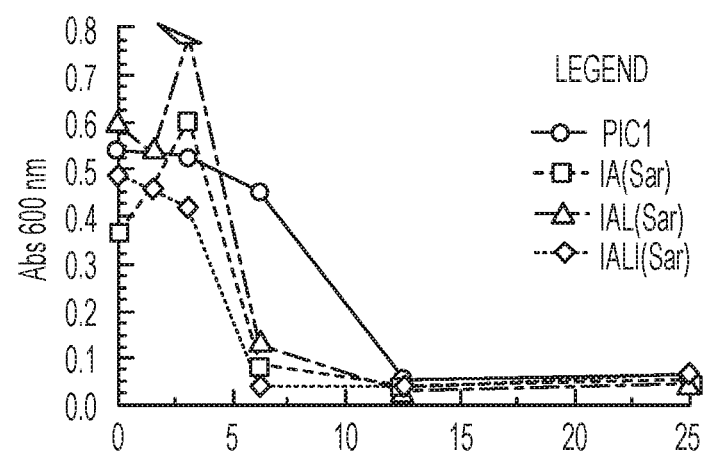
Figure 6:
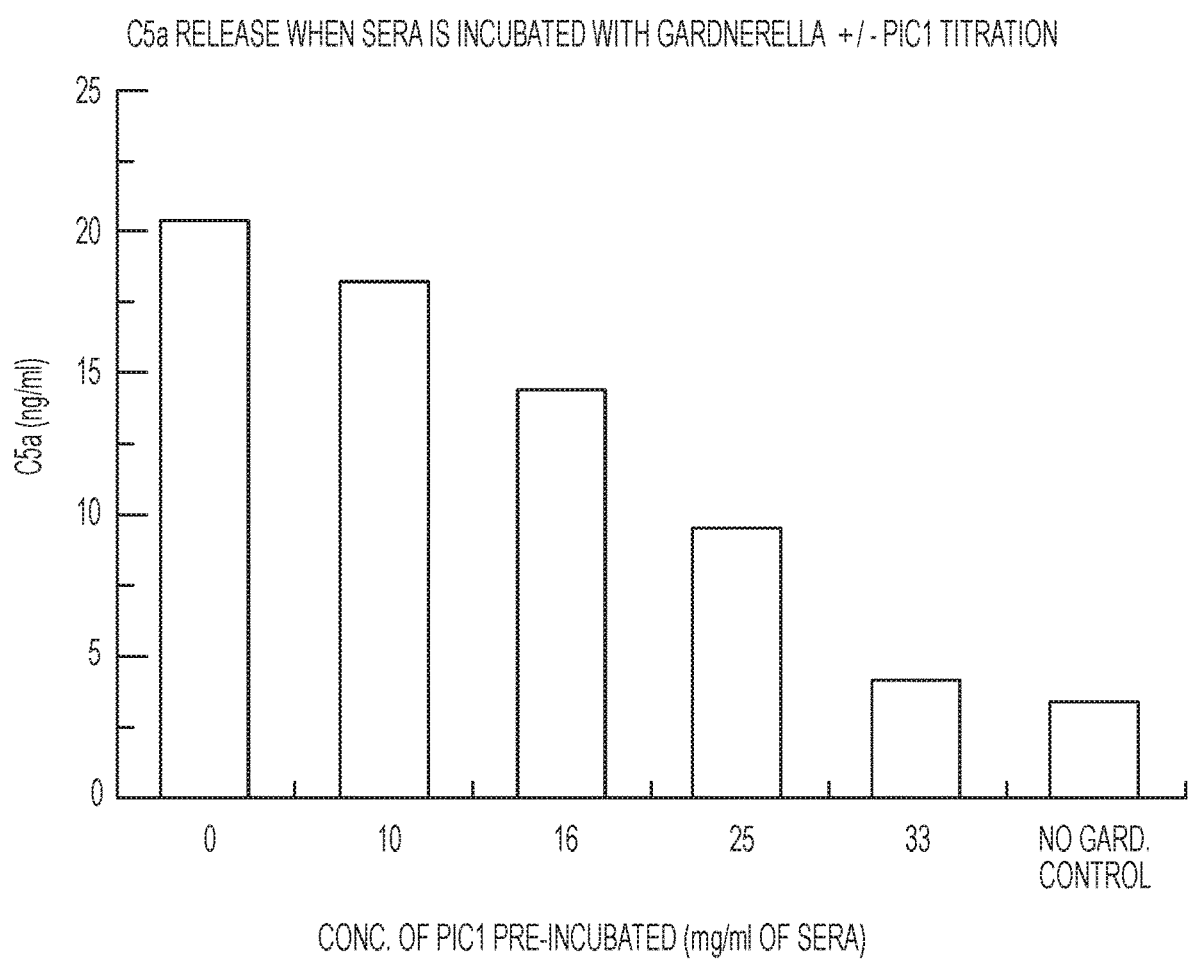
FIG. 6 shows C5a release when serum is incubated with *Gardnerella* at different concentrations of PA-dPEG24 (SEQ ID NO: 21). PIC1=PA-dPEG24 (SEQ ID NO: 21).

As shown in FIG. 2B, PA-dPEG24 (SEQ ID NO: 21) inhibited complement activation to the same degree as PA and displayed a broader dose-response most likely due to its increased solubility in aqueous solution. The structure of PA-dPEG24 (SEQ ID NO: 21) is shown in FIG. 3.

Next, PEGylated PIC1 derivatives were designed with decreasing numbers of PEG moieties on the C terminus. As shown in TABLE 6 below, most of these peptides retained solubility and complement inhibitory activity, with PA-dPEG24 (SEQ ID NO: 21) demonstrating the best inhibitory activity.

Results: Solubility of PEGylated Peptides

TABLE 6 shows the solubility and hemolytic assay in factor B depleted serum of PEGylated PA peptides. The final concentration of peptide in factor B-depleted serum was 0.77 mM. Peptides not soluble in water were re-suspended in DMSO. In the hemolytic assay, soluble peptides were standardized to water and insoluble peptides standardized to DMSO.

TABLE 6

| Peptide name | Peptide sequence | SEQ ID NO | Solubility in water | Hemolysis (%) |
|---|---|---|---|---|
| Water | | | — | 100.00 |
| DMSO | | | — | 95.17 |
| PA-dPEG24 | IALILEPICCQERAA-dPEG24 | 21 | Yes | 2.99 |
| PA-dPEG20 | IALILEPICCQERAA-dPEG20 | 22 | Yes | 11.41 |
| PA-dPEG16 | IALILEPICCQERAA-dPEG16 | 23 | Yes | 12.04 |
| PA-dPEG12 | IALILEPICCQERAA-dPEG12 | 24 | Yes | 11.41 |
| PA-dPEG08 | IALILEPICCQERAA-dPEG08 | 25 | Yes | 34.66 |
| PA-dPEG06 | IALILEPICCQERAA-dPEG06 | 26 | No | 44.82 |
| PA-dPEG04 | IALILEPICCQERAA-dPEG04 | 27 | Yes | 12.36 |
| PA-dPEG03 | IALILEPICCQERAA-dPEG03 | 28 | Yes | 12.57 |
| PA-dPEG02 | IALILEPICCQERAA-dPEG02 | 29 | Yes | 11.62 |

Figure 20:
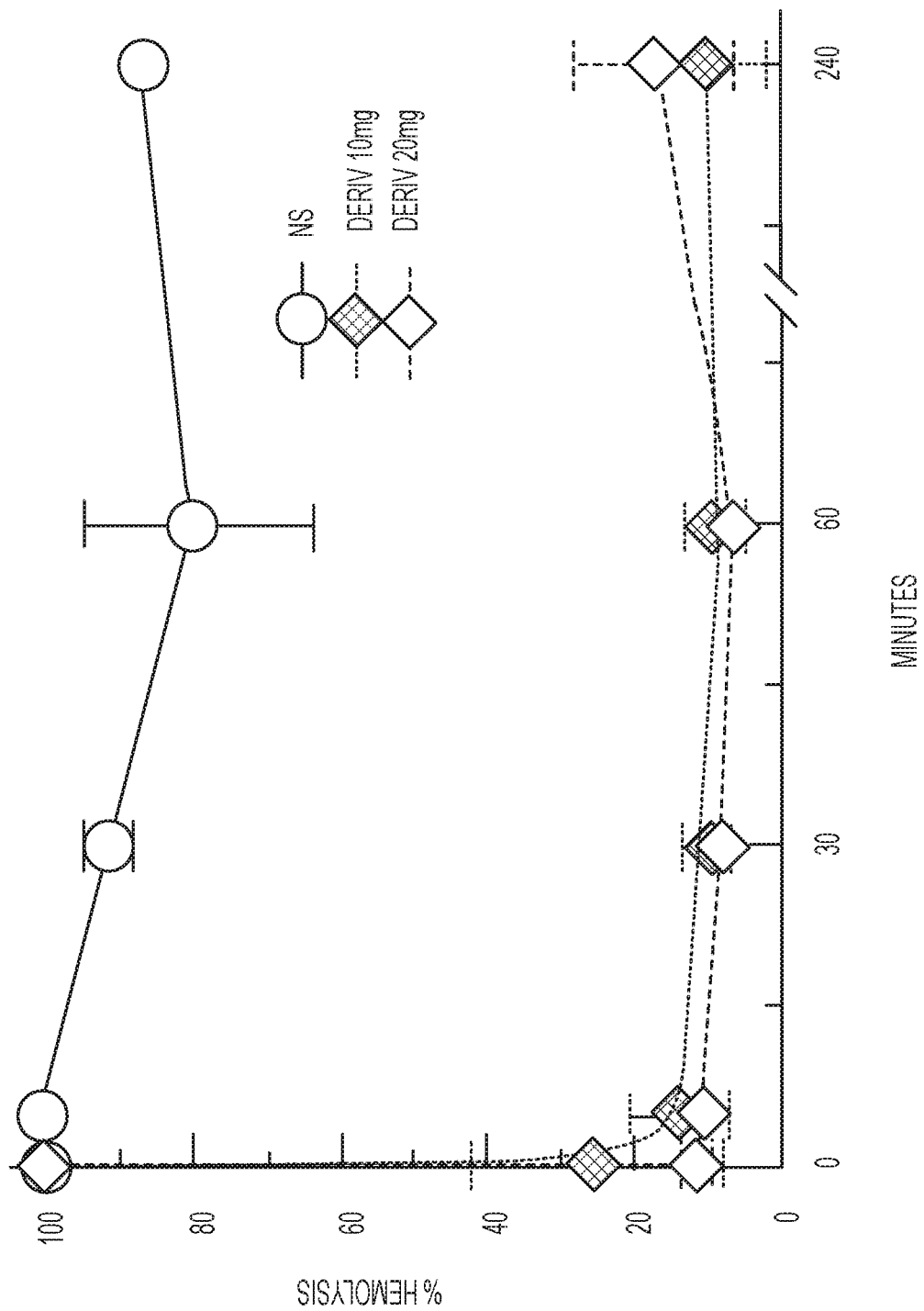
FIG. 20 shows red blood cell lysis in a hemolytic assay in rats treated with two different doses of PA-dPEG24 (SEQ ID NO: 21) or with normal saline.

In vivo data in rats demonstrated that PA-dPEG24 (SEQ ID NO: 21) inhibits complement activation (as measured by red blood cell lysis in a hemolytic assay) by up to 90% within 30 seconds upon injection into rats with inhibitory activity still observed up to 4 hours (FIG. 20). The two doses were given intravenously (IV). This was compared to the vehicle control (normal saline) which shows maximal hemolysis at all time points. PA-dPEG24 (SEQ ID NO: 21) was effective in vivo in 0.9% NaCl+10 mM NaHPO$_4$, but also works in saline and likely other common aqueous solutions (eg., Ringer's lactate, D5W, etc.) for IV infusion in humans.

Example 3—Solubility and Hemolytic Assay of PEGylated and Sarcosine (SAR) and/or Alanine Substitution Peptides Table 7 shows the solubility and hemolytic assay in factor B depleted serum of PEGylated and sarcosine (SAR) substitution peptides. The final concentration of peptide in factor B-depleted serum was 0.77 mM. Peptides not soluble in water were re-suspended in DMSO. In the hemolytic assay, soluble peptides are standardized to water and insoluble peptides standardized to DMSO.

TABLE 7

| Peptide name and controls | Peptide sequence | SEQ ID NO | Solubility in water | Hemolysis (%) |
|---|---|---|---|---|
| Water | — | | — | 100.00 |
| DMSO | — | | — | 95.17 |
| PA-dPEG24 | IALILEPICCQERAA-dPEG24 | 21 | Yes | 2.99 |
| PA-C9SarC10A | IALILEPI(Sar)AQERAA | 30 | Yes | 99.37 |
| PA-C9SarD10 | IALILEPI(Sar)QERAA | 31 | Yes | 100.52 |
| PA-P7SarC9Sar | IALILE(Sar)I(Sar)CQERAA | 32 | Yes | 82.72 |
| PA-E6Sar-dPEG24 | IALIL(Sar)PICCQERAA-dPEG24 | 33 | Yes | 12.88 |
| PA-Q11Sar-dPEG24 | IALILEPICC(Sar)ERAA-dPEG24 | 34 | Yes | 12.04 |
| PA-R13Sar-dPEG24 | IALILEPICCQE(Sar)AA-dPEG24 | 35 | Yes | 4.26 |
| PA-A14Sar-dPEG24 | IALILEPICCQER(Sar)A-dPEG24 | 36 | Yes | 3.68 |
| E6SarP7Sar | IALIL(Sar)(Sar)ICCQERAA | 37 | Yes | 3.57 |
| E6SarC9Sar | IALIL(Sar)PI(Sar)CQERAA | 38 | Yes | 6.21 |
| Q11SarP7Sar | IALILE(Sar)ICC(Sar)ERAA | 39 | Yes | 3.22 |
| Q11SarC9Sar | IALILEPI(Sar)C(Sar)ERAA | 40 | Yes | 15.42 |
| R13SarP7Sar | IALILE(Sar)ICCQE(Sar)AA | 41 | No | 26.35 |
| R13SarC9Sar | IALILEPI(Sar)CQE(Sar)AA | 42 | No | 84.81 |

TABLE 7-continued

| Peptide name and controls | Peptide sequence | SEQ ID NO | Solubility in water | Hemolysis (%) |
|---|---|---|---|---|
| A14SarP7Sar | IALILE(Sar)ICCQER(Sar)A | 43 | Yes | 4.37 |
| A14SarC9Sar | IALILEPI(Sar)CQER(Sar)A | 44 | No | 14.73 |
| E6AE12A-dPEG24 | IALILAPICCQARAA-dPEG24 | 45 | Yes | 4.95 |
| E6AE12AC9Sar | IALILAPI(Sar)CQARAA | 46 | No | 2.99 |
| E6AE12AP7Sar | IALILA(Sar)ICCQARAA | 47 | Yes | 4.60 |

Changes were made to the PA peptide in which multiple amino acids were substituted with sarcosine and/or alanine. Some peptides were further combined with PEGylation. Multiple peptides retained the same level of inhibitory activity and solubility as PA-dPEG24 (SEQ ID NO: 21), including, PA-R13Sar-dPEG24 (SEQ ID NO:35), PA-A14Sar-dPEG24 (SEQ ID NO: 36), E6SarP7Sar (SEQ ID NO: 37), Q11SarP7Sar (SEQ ID NO: 39), A14SarP7Sar (SEQ ID NO: 43), E6AE12A-dPEG24 (SEQ ID NO: 45), and E6AE12AP7Sar (SEQ ID NO: 47).

Example 4—Minimum Inhibitory Concentration (MIC) for PIC1 Peptides

Methods: Minimum Inhibitory Concentration (MIC) Assay.

A microdilution minimum inhibitory concentration (MIC) assay was performed where increasing amounts of PA-dPEG24 (SEQ ID NO:21) or sarcosine-derivatives (SEQ ID NO: 4-18, 30-47) was added to various bacteria growing in broth culture in a microtiter plate. The plates were then incubated at 37° C. overnight and then the plates were read on a spectrophotometer at an absorbance of OD600 nm to determine the turbidity of the solution. Decreased turbidity is indicative of inhibition of bacterial growth.

Results

PA-dPEG24 (SEQ ID NO: 21) was able to dose-dependently inhibit *Staphylococcus aureus* growth compared to a saline control (FIG. 4A) above 1 mM concentration and inhibited the same pathogen in a similar manner to the antibiotic vancomycin (FIG. 4B). PA-dPEG24 (SEQ ID NO: 21) was able to inhibit *Klebsiella pneumonia* at >3 mg/ml similar to gentamycin (FIG. 4C) and also inhibit *Pseudomonas aeruginosa* (FIG. 4D) at >13 mg/ml. The activity of PA-dPEG24 (SEQ ID NO: 21) was compared to 3 water soluble sarcosine substitution peptides (PA L3Sar (SEQ ID NO: 6), PA I4Sar (SEQ ID NO: 7) and PA L5Sar (SEQ ID NO: 8)) against *Pseudomonas aeruginosa* and it was found that all 3 sarcosine-derivatives peptides dose-dependently inhibited this species of bacteria at >6 mg/ml (FIG. 4E). These results demonstrate a completely novel antimicrobial property of these peptides which has not been previously reported that is completely independent of the complement suppressing properties of the PIC1 family of peptides.

Next, it was tested whether PA-dPEG24 (SEQ ID NO: 21), PA L3Sar (SEQ ID NO: 6), PA I4Sar (SEQ ID NO: 7) and PA L5Sar (SEQ ID NO: 8) could inhibit the growth of *Gardnerella*, a Gram variable, anaerobic coccobacillus that is a common cause of bacterial vaginosis. All 4 peptides inhibited the growth of *Gardnerella* (FIG. 5). It was also assayed whether PA-dPEG24 (SEQ ID NO: 21) could inhibit *Gardnerella*-mediated complement activation. In this assay normal human serum was incubated with *Gardnerella* in the presence of increasing amounts of PA-dPEG24 (SEQ ID NO: 21) for 1 hour at room temperature. Complement activation was assayed by measuring the production of C5a using ELISA methodology. Increasing amounts of PA-dPEG24 (SEQ ID NO: 21) inhibited C5a formation (FIG. 6). These results suggest that PIC1 peptides (e.g. SEQ ID NOs: 3-47) could be delivered locally in the vagina to treat bacterial vaginosis by inhibiting the replication of *Gardnerella* as well as *Gardnerella*-initiated inflammation. The associated inflammation causes the symptoms of bacterial vaginosis and increases the risk of HIV-transmission by disrupting normal barrier defenses in the vagina.

Example 5—Assay to Detect Complement-Mediated Hemolysis can Discriminate Erythrocyte Transfusions Likely to Cause Acute Transfusion Reactions (ATR)

Methods: Assay to Detect Complement-Mediated Hemolysis.

A 13 year old female B+ with sickle cell disease received three units of O+ packed red blood cells (pRBCs) from two different donors. During the first transfusion of two units, the patient experienced hypotension (BP 89/39) followed by fever (Tmax 102.6° F.). Transfusions of the third transfused product was tolerated without complications. Due to suspicion for an acute transfusion reaction (ATR), transfusion reaction work-up of the first transfused blood product revealed elevated anti-B titers. Subsequent investigative study of both identified donors indicated the following: Donor #1 was a 48 year old male with no reported transfusion adverse events. Donor #2 was a 61 year old female with prior pregnancies, but no reported transfusion adverse events.

Plasma from both donors were diluted with GVBS++ (veronal buffered saline with 0.1% gelatin, 0.15 mM $CaCl_2$) and 1 mM $MgCl_2$) and incubated with purified erythrocytes from a B+ donor at 37° C. for 1 hour. Free hemoglobin was measured by spectrophotometer at 412 nm. Classical complement activation was further evaluated by adding the classical complement pathway inhibitor PA-dPEG24 (SEQ ID NO: 21) to the hemolytic plasma sample prior to incubation with erythrocytes.

Results

Complement mediated hemolysis was >100-fold different between the two plasma samples from the different donors (TABLE 8). TABLE 8 shows plasma anti-B titers and complement hemolysis for two O+ donors. Classical complement activation was confirmed by blocking hemolysis with the classical complement pathway inhibitor, PA-dPEG24 (SEQ ID NO: 21).

TABLE 8

| | Anti-B titer (plasma) | | Complement hemolysis | Hemolysis in presence of |
|---|---|---|---|---|
| | RT | 37° C. | IgG | (Abs 412 nm) | PA-dPEG24 |
| Donor O+ #1 | 128 | 64 | 256 | 0.747 | 0.008 |
| Donor O+ #2 | 128 | 16 | 256 | 0.007 | |

Figure 7:
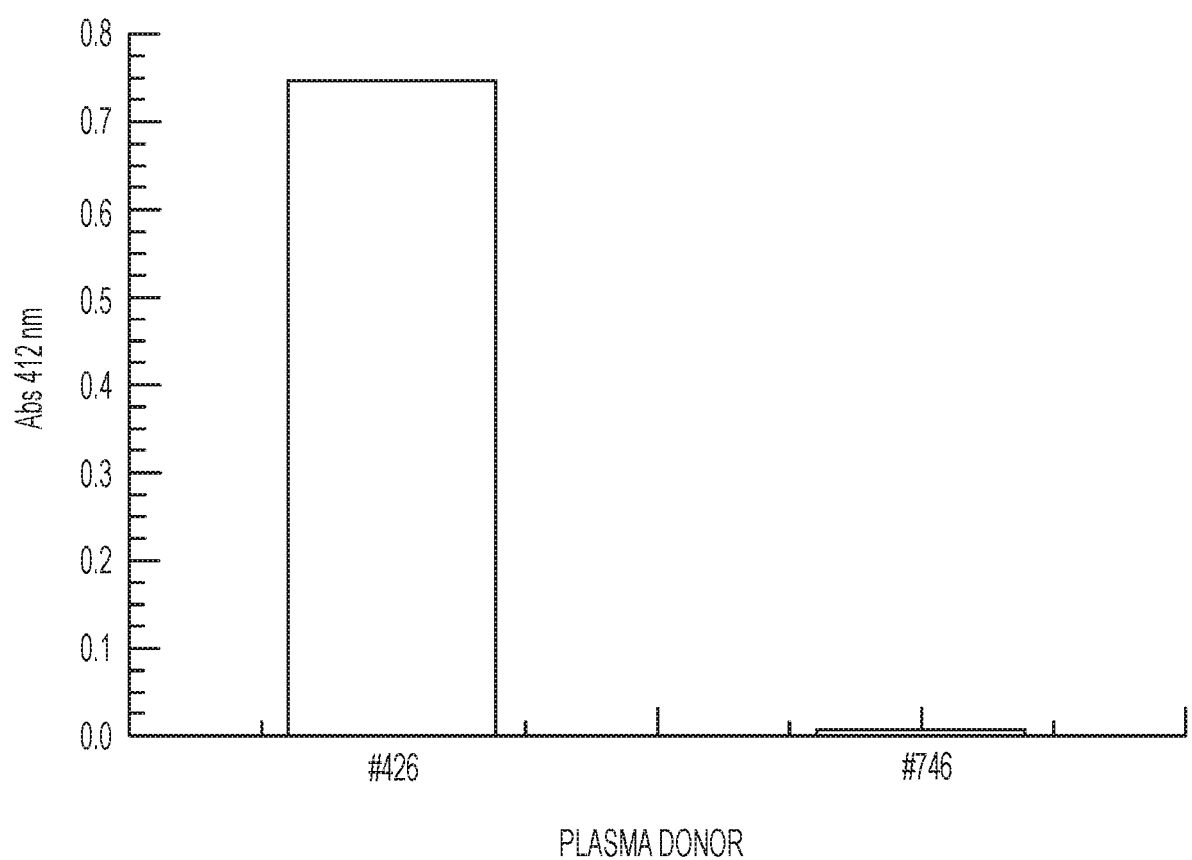
FIG. 7 shows two type-O plasmas from the RBC transfusions that caused ATR in a blood type-B recipient. The IgG titers for each plasma was quite high, but non-discriminatory. However, in a CH50-type hemolytic assay, they behave drastically differently. One is highly hemolytic, while the other does not cause significant hemolysis.
Figure 8:
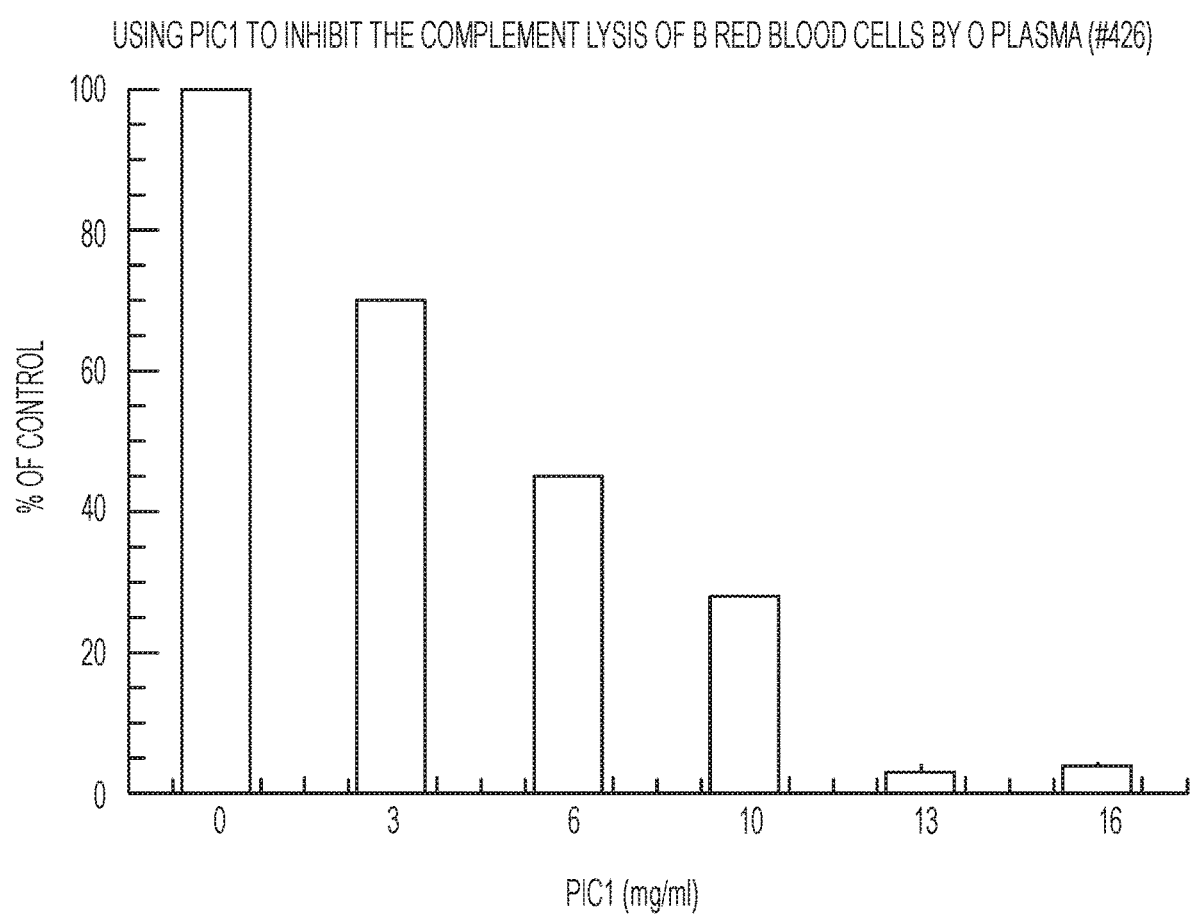
FIG. 8 shows the type-O plasma (#426) from the RBC transfusions that caused ATR in blood type-B recipient. Prior to adding B erythrocytes, PA-dPEG24 (SEQ ID NO: 21) was added to the plasma in increasing concentrations. A dose-response inhibition of hemolysis was demonstrated with PA-dPEG24 (SEQ ID NO: 21) demonstrating up to >95% inhibition.

This data demonstrates that PIC1 peptides (e.g. SEQ ID NOs: 3-47) could be utilized to ascertain if ATRs are complement mediated. The data in TABLE 8 above is shown in FIG. 7 along with a dose-response PA-dPEG24 (SEQ ID NO: 21) inhibition study of the highly hemolytic plasma sample (FIG. 8). A dose-response inhibition of hemolysis was demonstrated with PA-dPEG24 (SEQ ID NO: 21) up to >95% inhibition. This showed that the type-O RBC transfusion leading to ATR in the type-B recipient was a classical complement-mediated event. FIG. 8 showed it was possible to pharmacologically block the extremely robust hemolytic activity mediated by this donor's plasma in this ATR in vitro model.

Conclusion

Past methodologies have not been able to adequately predict the likelihood of complement-mediated ATR. In this case two units of type-O RBCs were given to a type-B recipient who then suffered ATR. There was estimated to be about 30-40% plasma by volume in a unit of packed RBCs (pRBCs) (i.e. 150-200 ml plasma per 500 ml unit). The antibodies in the plasma of the RBC transfusions likely initiated classical pathway complement-mediated ATR. The IgG titers for the plasma from donor of each RBC transfusion were both high, and thus non-predictive of this platelet transfusion caused the AHTR. A CH50-type complement hemolytic assay, however, was able to readily identify which type-O plasma causes massive hemolysis of type-B erythrocytes (>100-fold increase). Therefore, a hemolytic complement assay performed before platelet transfusion would have identified that one of the units of platelets was likely to cause AHTR and could have prevented this serious adverse event.

Therefore, PIC1 peptides (SEQ ID NOS: 3-47) can be used to discriminate risk of complement-mediated ATR before a blood transfusion. This data also supports the use of PIC1 peptides (SEQ ID NOS: 3-47) as a treatment for ATRs in various clinical scenarios.

Example 6—PIC1 (SEQ ID NO: 21) Enhances Survival of Human Erythrocytes in an Animal Model of Acute Intravascular Hemolytic Transfusion Reaction Methods: Ethics Statement.

Adolescent male Wistar rats (200-250 g) with indwelling jugular catheters were purchased from Harlan laboratories and used under the Eastern Virginia Medical School (EVMS) IACUC (Institutional Animal Care and Use Committee) approved protocols 12-003 and 15-003. Central line maintenance was followed as recommended by the animal vendor, with approval from the EVMS IACUC.

After written informed consent was provided, a healthy human volunteer donated AB blood which was used to generate purified red blood cells (RBCs) (EVMS IRB protocol 02-06-EX 0216). These RBCs were also used for in vitro analyses as the source of human RBCs (huRBC).

Methods: Human RBC Purification and Animal Experiments

Human RBCs (huRBCs) acquired the morning of the animal experiments were processed as described in (Shah et al., "Complement inhibition significantly decreases red blood cell lysis in a rat model of acute intravascular hemolysis." Transfusion. 2014). This process generates 1 ml huRBCs at 80% hematocrit, which was given as a 15% transfusion to the rats.

Figure 21A:
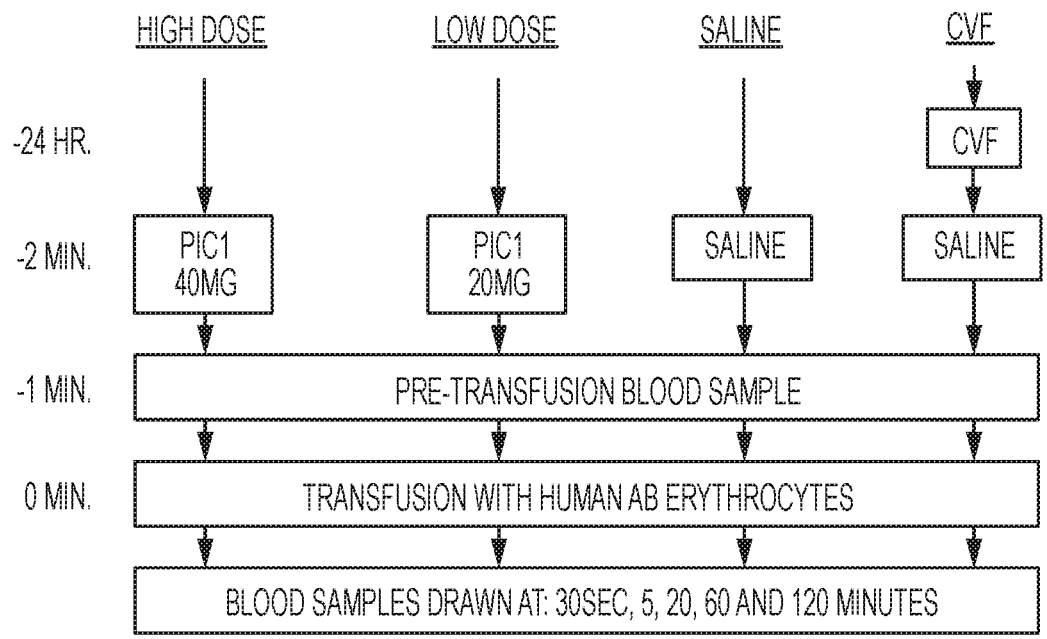
FIGS. 21A-B shows the experimental design and study arms.
Figure 21B:
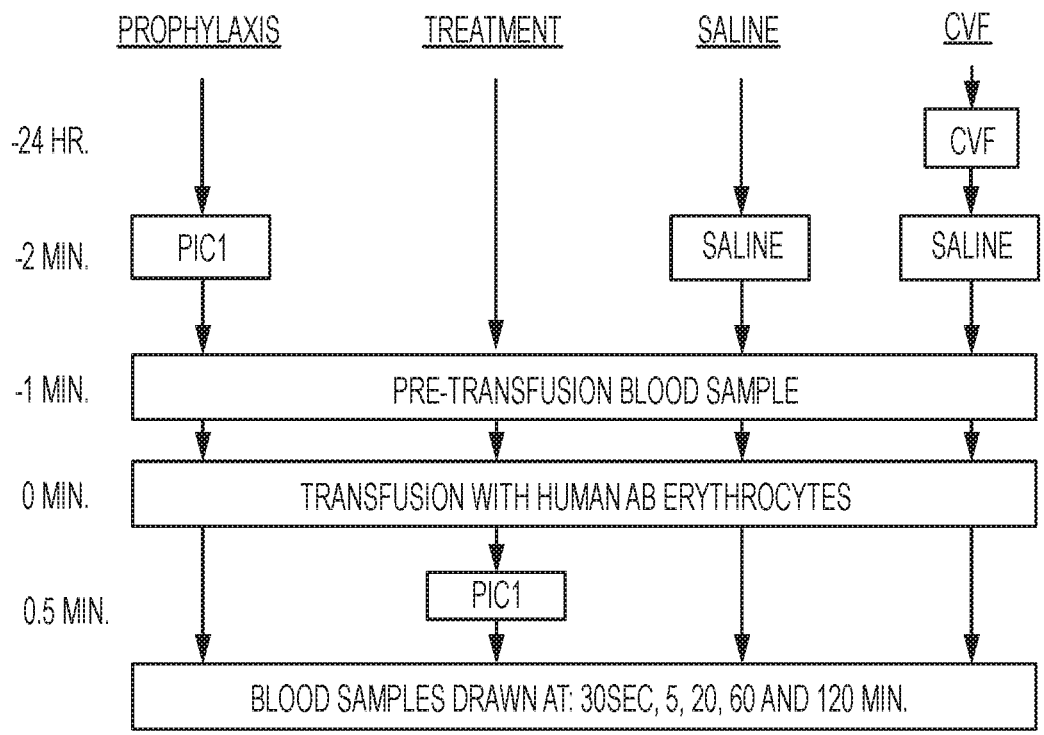

The AIHTR Wistar rat model was previously established in which cobra venom factor (CVF) was demonstrated to inhibit complement-mediated lysis of huRBCs, whereas animals receiving normal saline (NS) demonstrated classical pathway, complement-mediated hemolysis. (Shah T A, Mauriello C T, Hair P S, et al. "Complement inhibition significantly decreases red blood cell lysis in a rat model of acute intravascular hemolysis." Transfusion. 2014). Dosing of the PEGylated derivative, PA-dPEG24 (SEQ ID NO: 21) (New England Peptide, MA) was established in Wistar rats. FIG. 21A shows the sequence of events in a dosing experiment using a low (20 mg) and high dose (40 mg) of PA-dPEG24 (SEQ ID NO: 21) in the AIHTR animal model. Animals were randomly assigned to various groups where they received either normal saline (n=6), 20 mg PA-dPEG24 (SEQ ID NO: 21) (n=4) or 40 mg PA-dPEG24 (SEQ ID NO: 21) (n=7) before the huRBC transfusion (prophylaxis arm). FIG. 21B shows the second set of experiments where one group of animals received 40 mg PA-dPEG24 (SEQ ID NO: 21) (n=8) before the huRBC transfusion (prophylaxis arm) and a separate set of animals (n=10) receiving 40 mg PA-dPEG24 (SEQ ID NO: 21) after the huRBC transfusion (rescue arm). For both experiments, animals allotted to the saline control group received NS prior to huRBC transfusion whereas the CVF group received 130 μg CVF (Complement Technologies, Inc.) intra-peritoneum (I.P.) 24 hours prior to the huRBC transfusion. In an additional experiment, separate groups of animals were injected with 40 mg Immune globulin intravenous (POLYGAM®, Baxter Healthcare Corporation, CA) IVIG (n=3) and 40 mg PA-dPEG24 (SEQ ID NO: 21) (n=3) before the huRBC transfusion (IVIG vs. PA-dPEG24).

Using weight-based doses of ketamine and acepromazine, animals were sedated throughout the course of the experiment with periodic monitoring of vital signs. Blood samples were collected into EDTA microtainer tubes (BD) from the animals prior to the huRBC transfusion and then at 30 seconds, 5 minutes, 20 minutes, 60 minutes and 120 minutes after the huRBC transfusion. In the group of animals receiving WIG vs. PA-dPEG24 (SEQ ID NO: 21), blood samples were drawn prior to the huRBC transfusion and then 30 seconds, 5 minutes, 20 minutes, 60 minutes, 120 minutes, 180 minutes, 240 minutes, 300 minutes and 360 minutes after the huRBC transfusion. These samples were kept shaking at room temperature prior to processing and centrifuged at 2655×g for five minutes to separate out the plasma and sediment the RBCs. Plasma was aliquoted and the RBC pellet was processed separately as described below. Upon completion of the final (120 minutes or 360 minutes) blood draw, the animal was euthanized using Fatal Plus (Vortech). A necropsy was completed to collect organs (liver, spleen and bilateral kidney) for histopathology. In the experiment IVIG vs. PA-dPEG24 (SEQ ID NO: 21), bilateral kidneys acquired from each animal were weighted separately and stored in formalin prior to processing and paraffin embedding. Hematoxylin and eosin (H&E) stained sections were reviewed by a blinded pathologist.

Methods: Flow Cytometry

Flow cytometry was performed on the collected RBCs using a FACS Calibur flow cytometer (Becton Dickinson, Franklin Lakes, N.J.) with DXP 8 Color 488/637/407 Upgrade (Cytek Development, Fremont, Calif.). Samples were stained with either FITC and/or APC labeled antibodies. The data was acquired using Cytek FlowJo CE version 7.5.110.6. Approximately $1\times10^5$ and $5\times10^5$ events per sample were gathered for single and double labeled flow, respectively. Data was analyzed using FlowJo X version 10.0.7r2 (FlowJo LLC, Ashland, Oreg.). Although FITC and APC are not expected to cause much spillover, digital compensation was used in the analysis.

Single labeled flow: The RBC pellet collected after separating the plasma was washed, diluted and stained with FITC-conjugated anti-human CD235a (glycophorin A, eBioscience, San Diego, Calif.) at 1:200 in GVBS-- (veronal-buffered saline (VBS) with 0.1% gelatin, 0.01 mol/L EDTA) over 20 min while shaking at room temperature to minimize agglutination. An antibody control consisted of the RBC pellet washed, diluted and unstained or stained with mouse IgG2b Iso Control FITC at 1:200 (eBioscience, San Diego, Calif.).

Dual labeled flow: The RBC pellet generated above was washed and double stained with APC-conjugated mouse anti-human CD235a (glycophorin A, BD Bioscience, San Jose, Calif.) at 1:50 and FITC-conjugated goat-anti-rat C3 (MP Biomedical, Santa Ana, Calif.) at 1:200 in GVBS-- for 20 min at room temperature. Three controls consisting of unstained RBCs, RBCs acquired at 30 sec stained with the APC tagged antibody and FITC tagged antibody were used for quadrant analysis.

In vitro flow cytometry experiment: 100% complement sufficient Wistar rat sera (Innovative Research, Novi, Mich.) was incubated with PA-dPEG24 (SEQ ID NO: 21) at 12 mg/ml (4 mMol) for 5 minutes at room temperature to generate PA-dPEG24 (SEQ ID NO: 21) treated serum. HuRBC's prepared as above were then incubated with PA-dPEG24 (SEQ ID NO: 21) treated serum or with 100% complement sufficient Wistar rat sera untreated serum for 5 min each at 37° C. The cells were then washed twice with GVBS to terminate complement activation. These cells were then double stained with APC-conjugated mouse anti-CD235a and FITC-conjugated goat anti-C3 as described above. After washing, the cells were combined with 85% non-opsonized, non-stained cells to mimic the 15% transfusion used in vivo and analyzed by flow cytometry using the same conditions stated in dual labeled flow, above.

Methods: Hemoglobin and Bilirubin Measurements

Plasma generated from the above experiments was analyzed for the free hemoglobin using spectrophotometry, as described previously (Shah et al. "Clinical hypothermia temperatures increase complement activation and cell destruction via the classical pathway." *J Transl Med* 2014; 12:181.). For bilirubin measurements, the pre-bleed and 120 minute plasma samples from the prophylaxis (n=8) and NS (n=7) groups were analyzed for the amount of bilirubin present using the Bilirubin Assay Kit (Sigma-Aldrich, St. Louis, Mo.) in half the manufacturer's recommend volume. Due to large amounts of hemolysis in the latter time points and the associated optical interference in bilirubin analysis, all the samples were pre-treated with HemogloBind™ (Biotech, NJ) prior to analysis with the Bilirubin Assay Kit. (Koseoglu M, Hur A, Atay A, Cuhadar S. "Effects of hemolysis interferences on routine biochemistry parameters." *Biochemia medica*. 2011; 21(1):79-85].

Results

PA-dPEG24 (SEQ ID NO: 21) blocked AIHTR in rats when given prophylactically before the transfusion, as well as when PA-dPEG24 (SEQ ID NO: 21) was administered as rescue treatment after transfusion. PA-dPEG24 (SEQ ID NO: 21) was compared in a dose comparable fashion against intravenous immunoglobulin (IVIG) in the AIHTR disease animal model. IVIG is being used in clinical practice in conjunction with phototherapy to reduce the need for exchange transfusion in neonates with hyperbilirubinemia due to ABO incompatibility related hemolytic disease [Schwartz H P, Haberman B E, Ruddy R M. "Hyperbilirubinemia: current guidelines and emerging therapies." *Pediatric emergency care*. 2011; 27(9):884-889; "Management of hyperbilirubinemia in the newborn infant 35 or more weeks of gestation." *Pediatrics*. 2004; 114(1):297-316; Cortey A, Elzaabi M, Waegemans T, Roch B, Aujard Y. "Efficacy and safety of intravenous immunoglobulins in the management of neonatal hyperbilirubinemia due to ABO incompatibility: a meta-analysis."*Archives de pediatrie: organe officiel de la Societe francaise de pediatric*. 2014; 21(9):976-983].

Figure 22A:
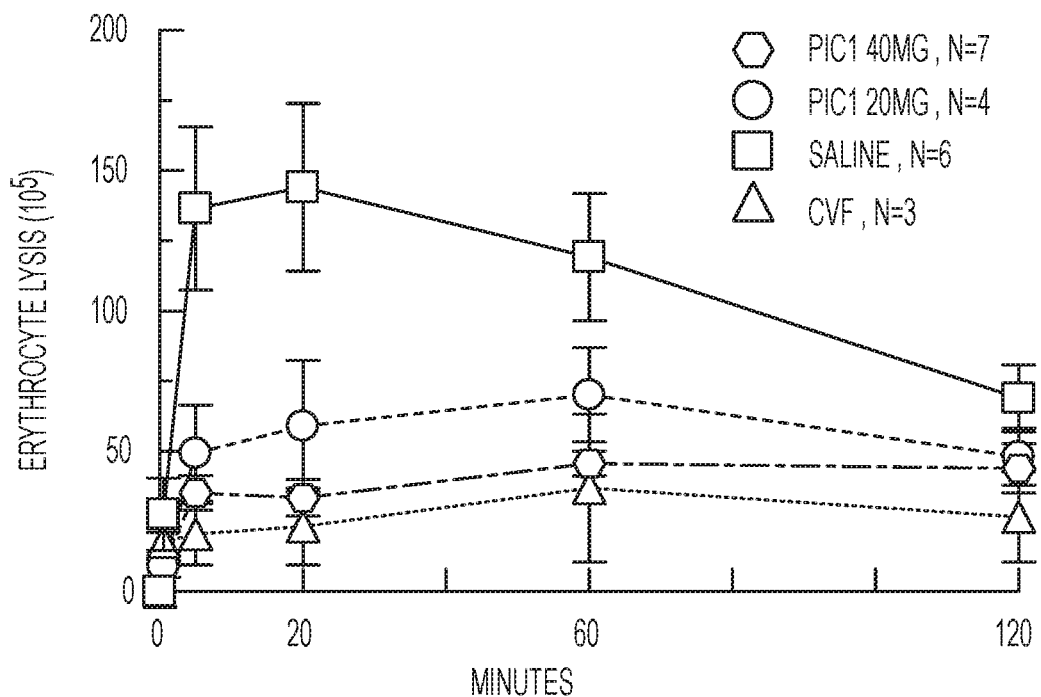
FIGS. 22A-B shows PA-dPEG24 (SEQ ID NO: 21) dosing studies in AIHTR model comparing high dose PA-dPEG24 (SEQ ID NO: 21) (40 mg) vs. lose dose PA-dPEG24 (SEQ ID NO: 21) (20 mg).
Figure 22B:
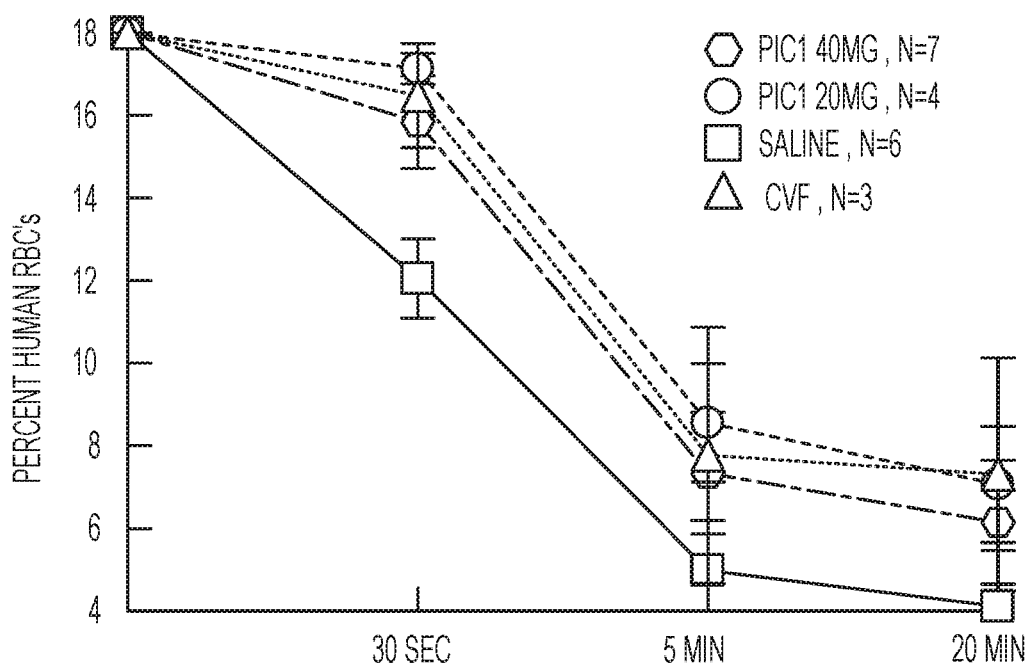

Example 7—PIC1 (SEQ ID NO: 21) Enhances Survival of Human Erythrocytes in an Animal Model of Acute Intravascular Hemolytic Transfusion Reaction—Prophylactic Administration of SEQ ID NO: 21 Reduces Hemolysis of huRBCs in the AIHTR Model Previous work had established the AIHTR model in Wistar rats and demonstrated that a 15% transfusion of HuRBC resulted in classical pathway-mediated intravascular lysis of the xenotransfused cells [Shah et al. "*Complement inhibition significantly decreases red blood cell lysis in a rat model of acute intravascular hemolysis*." Transfusion. 2014 November; 54(11):2892-900.] "Clinical hypothermia temperatures increase complement activation and cell destruction via the classical pathway." *J Transl Med* 2014; 12:1811. Depletion of complement activity by CVF led to increased survival of HuRBC as shown by flow cytometry and free hemoglobin measurements with the transfused cells eventually being sequestered in the spleen and liver [Shah et al. "*Complement inhibition significantly decreases red blood cell lysis in a rat model of acute intravascular hemolysis*." Transfusion. 2014 November; 54(11):2892-900]. To assess the efficacy of PA-dPEG24 (SEQ ID NO: 21) inhibition on the survival of huRBCs in this AIHTR model, animals were prophylactically treated with PA-dPEG24 (SEQ ID NO: 21) at doses of 20 and 40 mg/animal followed by 15% xenotransfusion of HuRBCs and blood draws at the indicated time points (FIG. 22A). Animals pre-treated with CVF served as a positive control for complement depletion and a separate set of animals received NS (vehicle control). Plasma isolated from NS-treated animals demonstrated a spike of hemolysis as assayed by released free hemoglobin (FIG. 22A). In contrast, animals pre-treated with CVF had low levels of free hemoglobin as previously reported (FIG. 22A) [Shah et al. "*Complement inhibition significantly decreases red blood cell lysis in a rat model of acute intravascular hemolysis*." Transfusion. 2014 November; 54(11):2892-900.]. Animals receiving both doses of PA-dPEG24 (SEQ ID NO: 21) showed decreased levels of free hemoglobin similar to that observed for CVF-treated animals; animals receiving 40 mg PA-dPEG24 (SEQ ID NO: 21) showed significant reduction of free hemoglobin compared to NS control animals at 5 minutes and 20 minutes ($P<0.05$) (FIG. 22A). To verify the complement-mediated destruction of the transfused huRBC, RBCs from blood collected at the indicated time points were isolated and labeled with antibody to human glycophorin A (CD235a)

and analyzed by flow cytometry. Animals receiving 20 or 40 mg doses of PA-dPEG24 (SEQ ID NO: 21) showed survival of transfused cells comparable to that observed in the CVF treated animals up to 20 minutes (FIG. 22B). There was no statistically significant difference observed between the effects caused by both doses of PA-dPEG24 (SEQ ID NO: 21) and CVF in these experiments. These results show the protective effect of PA-dPEG24 (SEQ ID NO: 21) on the survival of incompatible HuRBCs in the animal model of AIHTR.

Figure 23A:
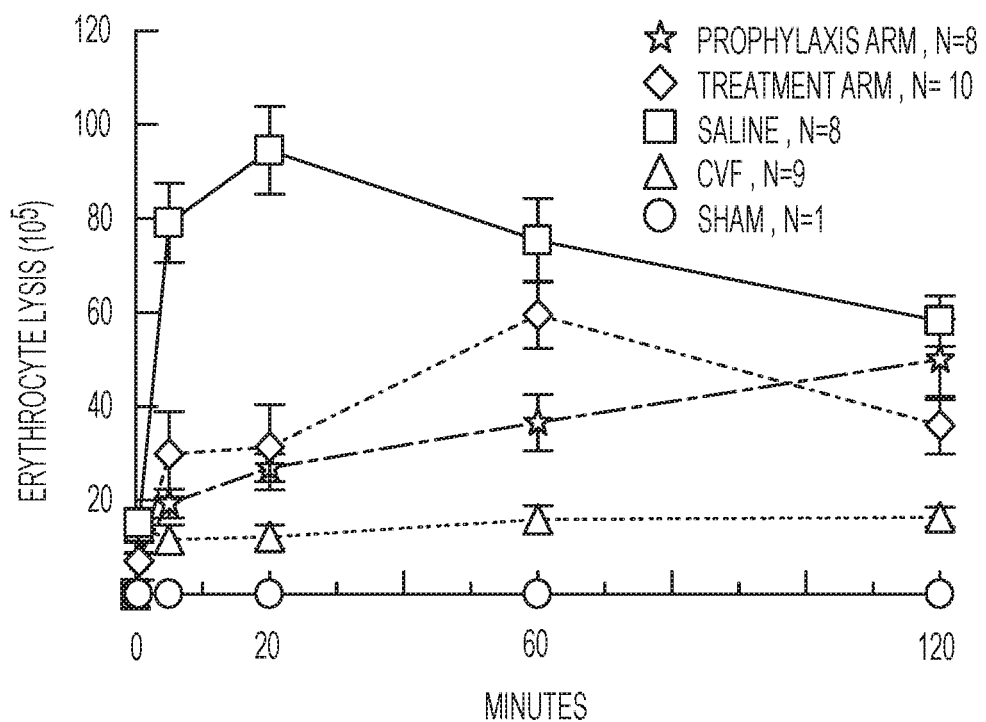
FIGS. 23A-C shows PA-dPEG24 (SEQ ID NO: 21) efficacy in prophylaxis (pre-transfusion) vs. treatment (rescue therapy, given after transfusion) in AIHTR model.
Figure 23B:
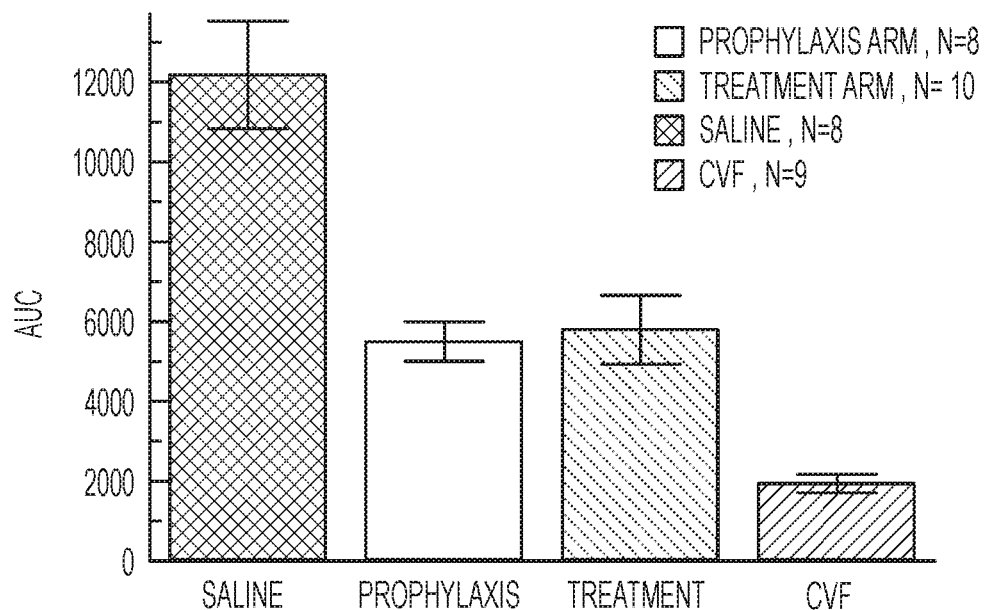
Figure 23C:
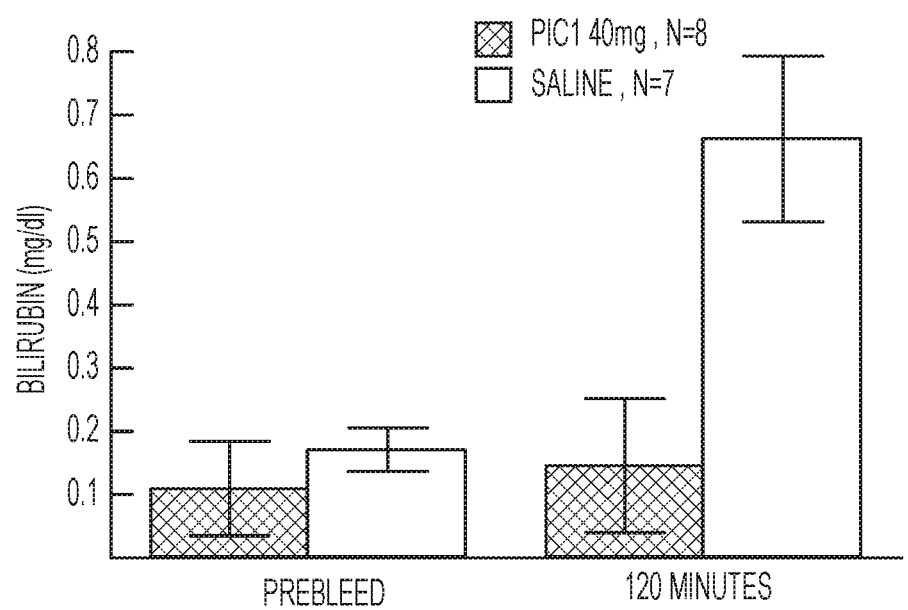

Example 8—PIC1 (SEQ ID NO: 21) Enhanced Survival of Human Erythrocytes in an Animal Model of Acute Intravascular Hemolytic Transfusion Reaction—Administration of SEQ ID NO: 21 after HuRBC Transfusion Protects the Transfused Cells from Complement-Mediated Hemolysis PA-dPEG24 (SEQ ID NO: 21) was able to show protection of the HuRBC when administered to rats prior to xenotransfusion, It was also discovered that PA-dPEG24 (SEQ ID NO: 21) given immediately after xenotransfusion could protect the HuRBCs from complement-mediated attack. Rats received a 40 mg dose of PA-dPEG24 (SEQ ID NO: 21) either 30 seconds before (prophylaxis arm) or 30 seconds after xenotransfusion of HuRBCs (treatment/rescue arm). A separate group of animals also received NS vehicle control or were pre-treated with CVF (FIG. 21B). The protective effect of 40 mg PA-dPEG24 (SEQ ID NO: 21) given before the transfusion (prophylaxis group) and after the transfusion (treatment/rescue group) on the amount of hemolysis as assayed by free hemoglobin was significantly reduced compared to the animals who received NS at 5 minutes (P<0.005) and 20 minutes (P<0.005) (FIG. 23A), representing the greatest amount of hemolysis in this AIHTR model (FIGS. 22A & 23A) FIG. 23B shows the cumulative hemolysis occurring in the various groups of animals (Saline, Prophylaxis, Treatment and CVF). Both the treatment and prophylaxis groups demonstrated reduced hemolysis compared to the saline group of animals (P<=0.05). Another common pathway of hemoglobin metabolism when it is released into the plasma as a result of intravascular hemolysis is indirect bilirubinemia [Strobel E. "Hemolytic Transfusion Reactions." *Transfusion medicine and hemotherapy offizielles Organ der Deutschen Gesellschaft fur Transfusionsmedizin and Immunhamatologie.* 2008; 35(5):346-353]. NS treated animals showed a large increase in free bilirubin between the pre-bleed and 120 minute time point (FIG. 23C), consistent with RBC lysis as assessed by free hemoglobin and flow cytometry. In contrast to the NS treated animals, 40 mg PA-dPEG24 (SEQ ID NO: 21) given prior to the transfusion of HuRBCs significantly reduced the amount of bilirubin circulating at 120 minutes compared to the animals receiving NS (P=0.0015) (FIG. 23C).

Figure 24A:
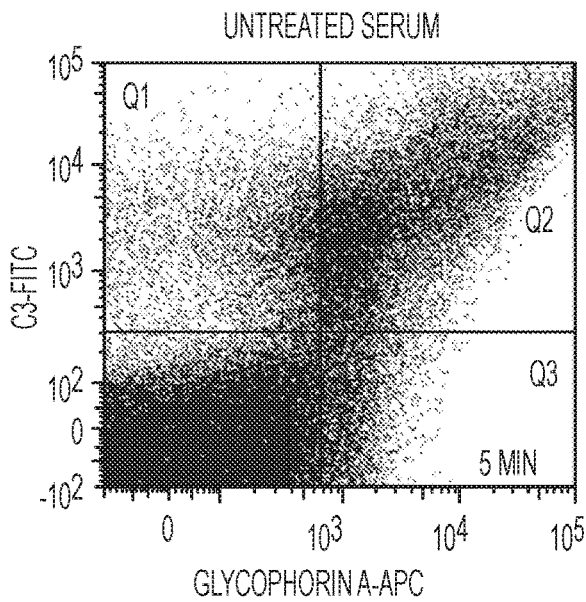
FIGS. 24A-D shows PA-dPEG24 (SEQ ID NO: 21) protection of human RBCs from lysis by rat serum in vitro.
Figure 24B:
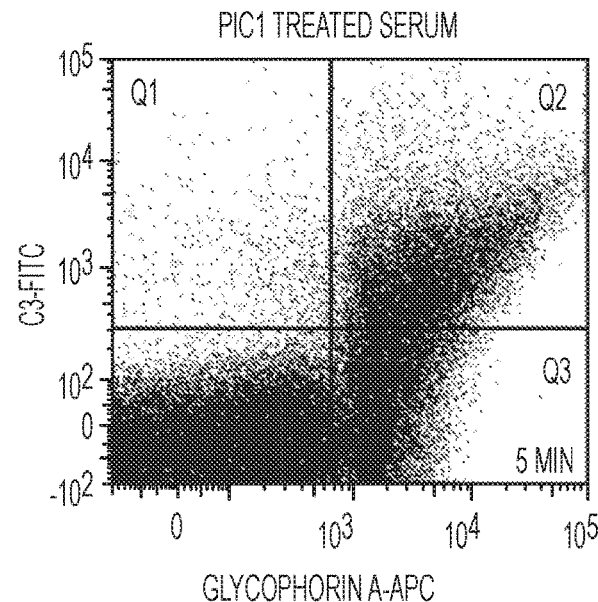
Figure 24C:
Figure 24D:
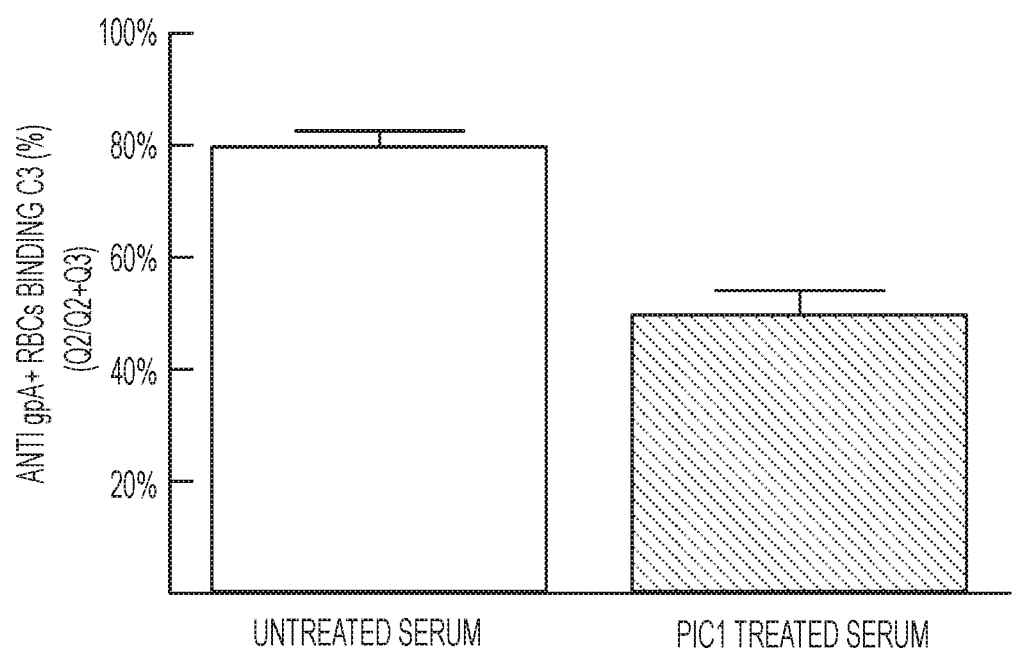

Example 9—Peptide Inhibitor of Complement C1 (SEQ ID NO: 21) Enhances Survival of Human Erythrocytes in an Animal Model of Acute Intravascular Hemolytic Transfusion Reaction—Assessment of Complement Deposition on Transfused HuRBCs The results described above demonstrate that PIC1 (SEQ ID NO: 21) can be utilized in both a prophylactic and treatment strategy to prevent hemolysis of transfused huRBC as assayed by huRBC survival, free hemoglobin levels and bilirubin release. To gain a more complete understanding of the role of complement deposition on the transfused cells, an analysis of C3 binding to huRBCs was conducted. To establish experimental conditions, an in vitro study was performed using HuRBCs exposed to rat serum followed by analysis of C3 deposition on the cells by flow cytometry. Rat serum treated with and without PA-dPEG24 (SEQ ID NO: 21) was added to HuRBCs and allowed to opsonize for 5 minutes. Cells were then analyzed by dual labeled flow cytometry with representative plots for HuRBCs exposed to untreated or PA-dPEG24 (SEQ ID NO: 21)-treated serum shown in FIGS. 24A and 24B, respectively. Quantification of HuRBCs opsonized in rat serum with and without PA-dPEG24 (SEQ ID NO: 21) showed a relative increase in the number of cells with no C3 deposition in PA-dPEG24 (SEQ ID NO: 21)-treated serum (FIG. 24C). When the fraction of dual labeled cells relative to the total number of glycophorin A labeled cells was calculated, there was a >1.5 fold reduction in C3 deposition on cells incubated with PA-dPEG24 (SEQ ID NO: 21)-treated serum versus untreated serum (FIG. 24D). In untreated serum, a larger population of dual labeled cells (Q2) was observed to shift over to Quadrant 1 which represented cells with C3 deposition. These findings demonstrated that PA-dPEG24 (SEQ ID NO: 21) rescued HuRBCs from opsonization and impending hemolysis through activation of the complement proteins in vitro.

Figure 25A:
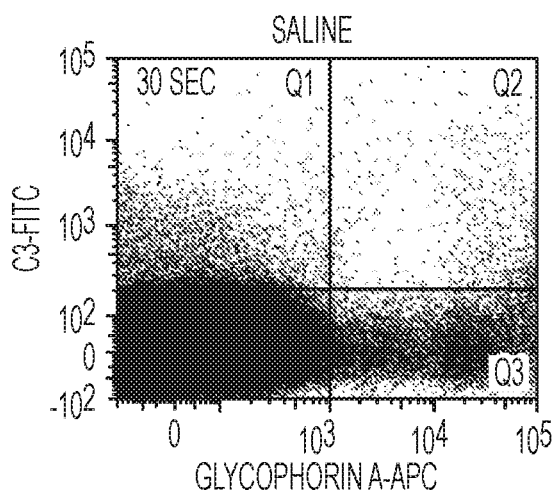
FIGS. 25A-F shows PA-dPEG24 (SEQ ID NO: 21) protection versus saline of human RBCs transfused into rats at 30 seconds (FIGS. 25A and 25D), 5 minutes (FIGS. 25B and 25E) and 20 minutes (FIGS. 25C and 25F). Flow cytometry analysis of RBCs recovered from blood draws and labeled with anti-glycophorin A (APC) and anti-C3 (FITC).
Figure 25D:
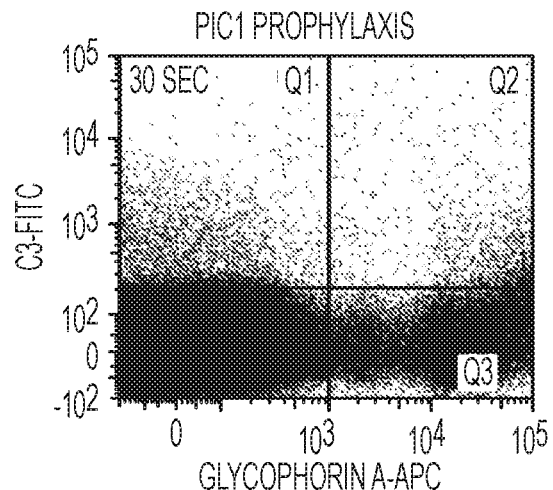
Figure 25B:
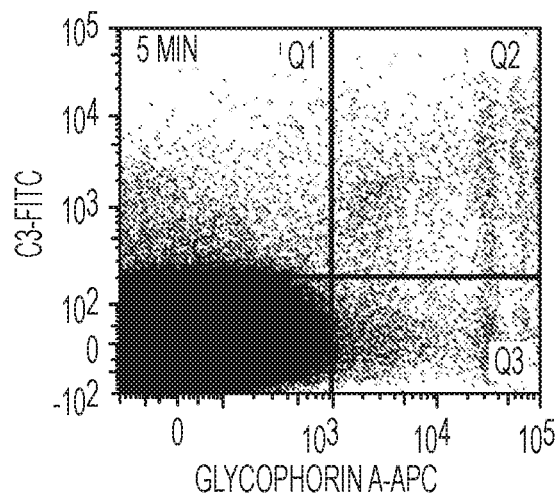
Figure 25E:
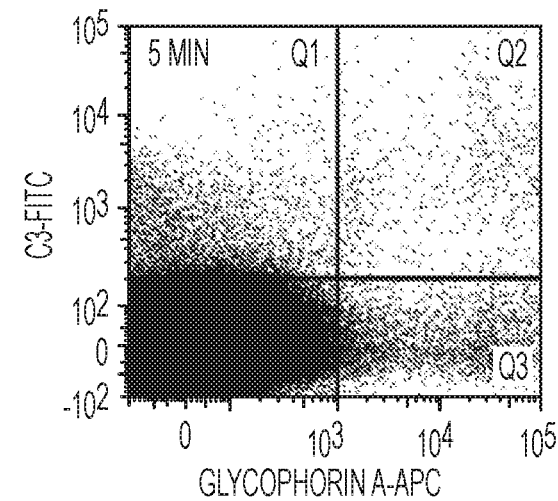
Figure 25C:
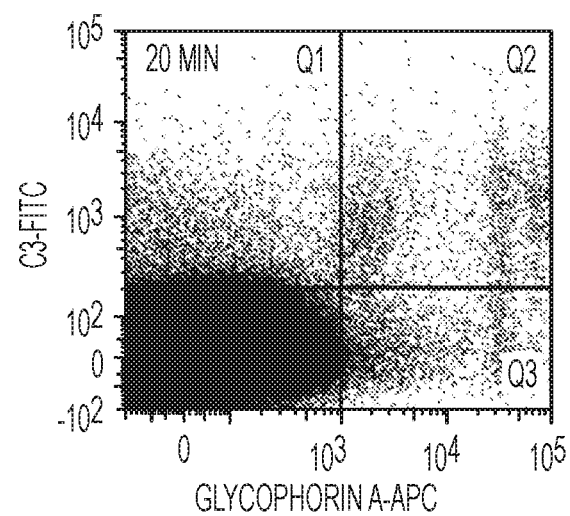
Figure 25F:
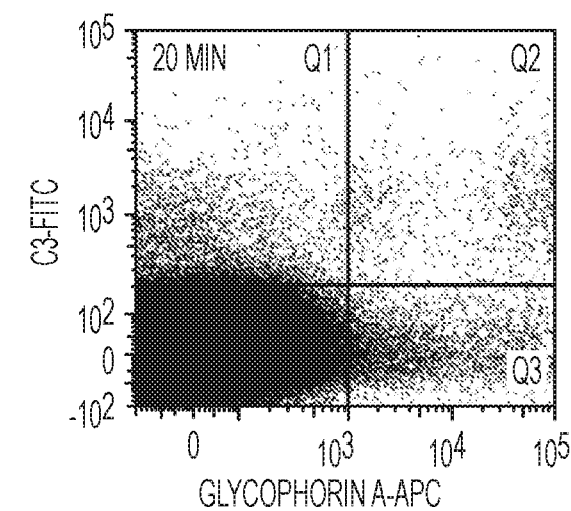
Figure 26A:
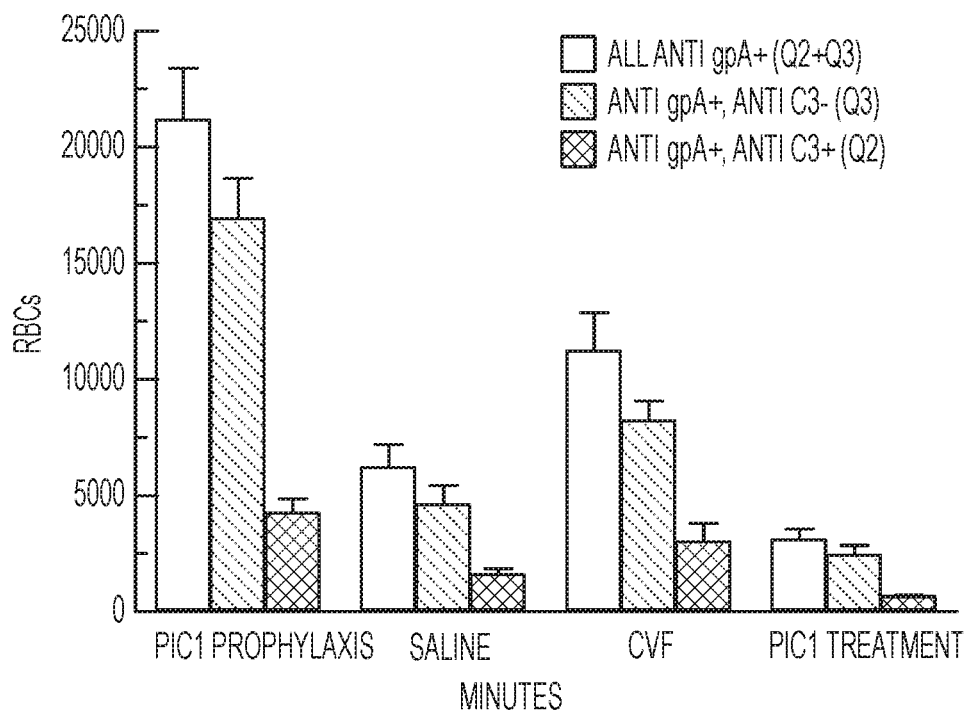
FIGS. 26A-D show transfused human RBC survival in rats.
Figure 26B:
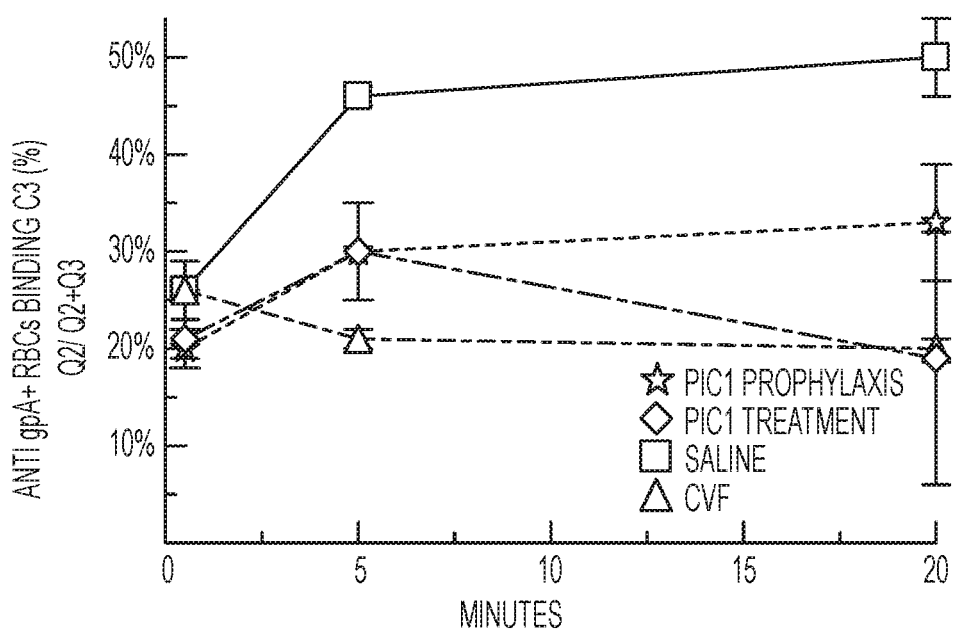
Figure 26C:
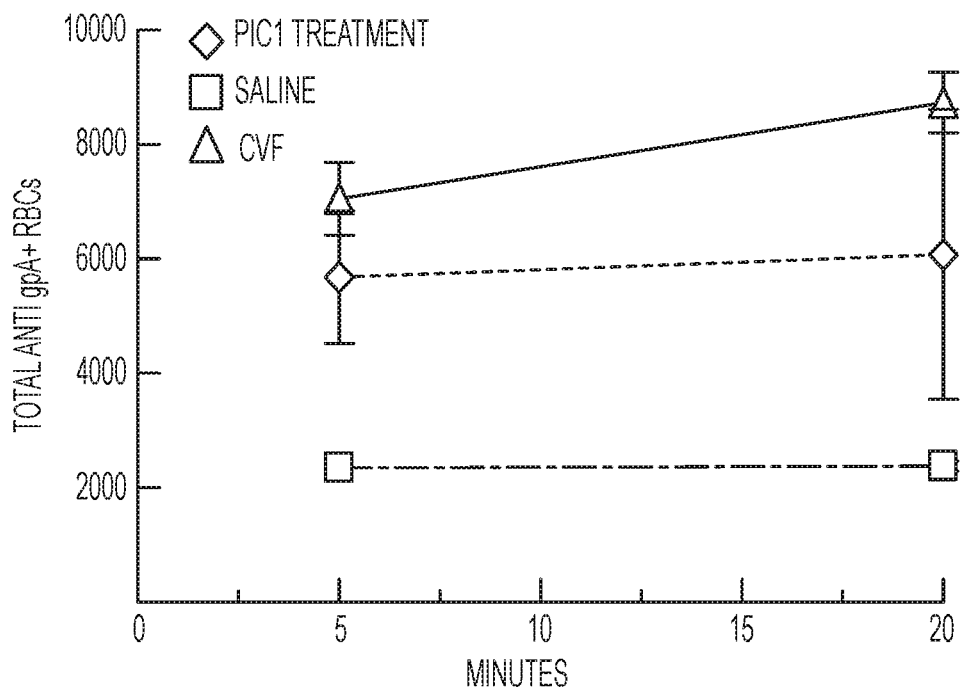
Figure 26D:
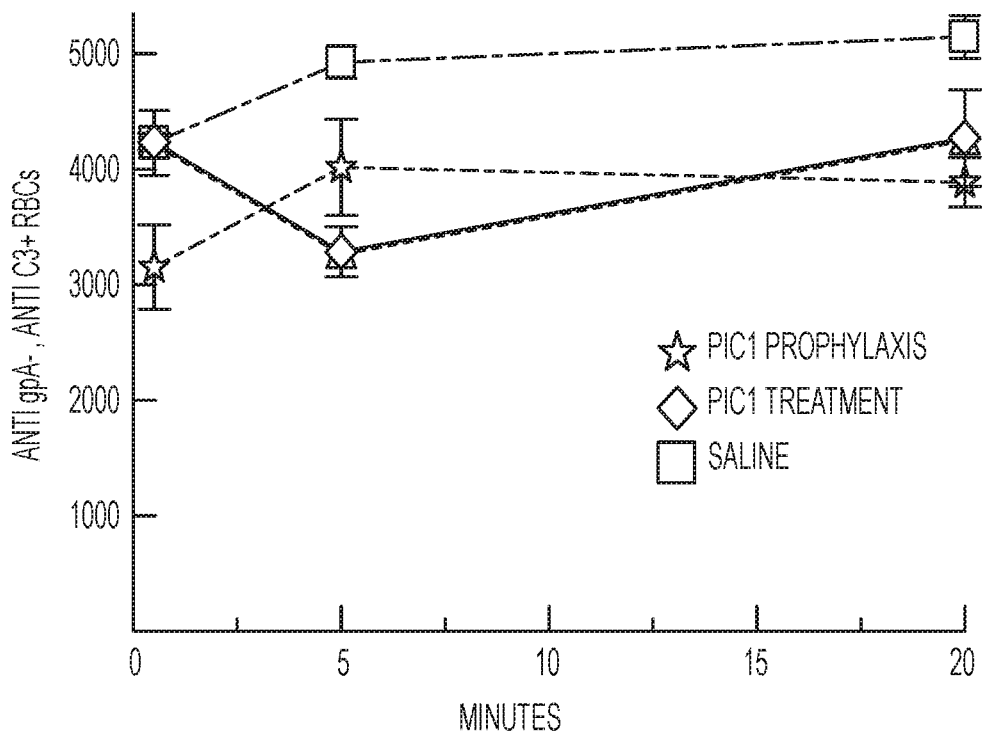

To evaluate the effect of PA-dPEG24 (SEQ ID NO: 21) on C3 deposition of transfused HuRBCs in the AIHTR model, RBCs isolated from the blood of animals that received either CVF, NS or PA-dPEG24 (SEQ ID NO: 21) prior to xenotransfusion or post-xenotransfusion were subject to two color flow cytometry for both human glycophorin A expression and rat C3. Representative flow cytometry plots of RBCs at 30 seconds, 5 minutes and 20 minutes post-transfusion are shown for NS (FIG. 25A-C) and PA-dPEG24 (SEQ ID NO: 21) treated (FIG. 25D-F) animals. NS-treated animals exhibited an increased number of double-positive cells over time compared to PA-dPEG24 (SEQ ID NO: 21)-treated animals. Conversely, PA-dPEG24 (SEQ ID NO: 21)-treated animals had more glycophorin A positive cells consistent with increased RBC survival as assessed by single label flow cytometry and free hemoglobin measurements (FIGS. 22A-B & 23A-C). To more precisely quantify these results, the numbers of events captured by flow cytometry were analyzed and graphed (FIG. 26A). At 30 seconds after HuRBC transfusion prophylactic treatment with PA-dPEG24 (SEQ ID NO: 21) showed a dramatic increase in the numbers of circulating HuRBCs (Human—No C3) compared with no intervention (NS) or even CVF-treated animals (FIG. 26A). The amount of surviving HuRBCs at 30 seconds for the PA-dPEG24 (SEQ ID NO: 21) treatment group was similar to the animals receiving NS, which was expected as PA-dPEG24 (SEQ ID NO: 21) was given 30 seconds after the transfusion (FIG. 26A). At 5 and 20 minutes after transfusion, groups of animals receiving prophylaxis and treatment with PA-dPEG24 (SEQ ID NO: 21) showed decreased C3 deposition on the surface of circulating HuRBCs compared with animals receiving no intervention (NS) (FIG. 26B). For animals receiving PA-dPEG24 (SEQ ID NO: 21) after transfusion (treatment arm), while many HuRBCs were cleared from the circulation prior to PA-dPEG24 (SEQ ID NO: 21) treatment (FIG. 26A), HuRBCs persisted in circulation through 20 minutes at higher numbers than that observed for the NS group (FIG. 26C). In order to evaluate complement attack of innocent bystander RBCs (i.e. rat RBCs), C3-fragment bound RBCs that were not labeled with anti-glycophorin A were counted. Prophylactic administration of PA-dPEG24 (SEQ ID NO: 21) decreased innocent bystander attack of non-glycophorin A RBCs at all observed time points compared to the NS control animals. Post-transfusion treatment with PA-dPEG24 (SEQ ID NO: 21) decreased 'innocent bystander' attack at the 5 and 20 minute time points (FIG. 26D).

Example 10—Investigation of Complement Effectors of Inflammation in Cystic Fibrosis Lung Fluid—Complement Anaphylatoxins in CF Lung Fluid Methods: Ethics Statement.

Sputum samples were obtained from consented patients as part of their standard of care visit at the Children's Hospital of The King's Daughters Cystic Fibrosis Center and collected from the Clinical Microbiology Laboratory prior to being discarded. This was performed under an Eastern Virginia Medical School IRB approved protocol 12-08-EX-0200. Samples were given a numerical code that was linked in an encrypted file to the clinical database. Control sputum samples were obtained from healthy human volunteers.
Methods: Sputum Sols Sputum samples were obtained as expectorated sputum and placed immediately on ice. To confirm that induction of sputum did not alter complement in the sol, a control experiment was performed with a healthy human volunteer who produced an expectorated sputum and an induced sputum showing no differences in complement activation or complement effector concentrations. The soluble (sol) fraction was generated by cold (4° C.) centrifugation at 14,000 g for 60 minutes and recovery of the free flowing liquid fraction, similar to methods previously described [Davies J R, Svitacheva N, Lannefors L, et al. "Identification of MUCSB, MUCSAC and small amounts of MUC2 mucins in cystic fibrosis airway secretions." *Biochem J* 1999; 344 Pt 2:321-30]. The sols were aliquoted and frozen at −80° C.
Clinical Data Clinical Data were obtained from data entered into Port CF for the clinic visit at which the sputum sample was collected and from review of the medical record. The FEV1% predicted value was obtained from pulmonary function testing performed at the clinic visit when the sputum sample was collected. The bronchiectasis score was based on the most recent radiographic lung study prior to obtaining the sputum sample, usually plain radiograph. A bronchiectasis score was assigned as follows: 0=normal; 1=1 lobe, mild; 2=2-4 lobes; 3=all lobes. Cystic fibrosis related diabetes (CFRD) status was based on the most recent endocrinology assessment prior to obtaining the sputum sample. CFRD status was scored as follows: 0=normal; 1=glucose intolerance; 2=CFRD. Part of each sputum sample was sent for microbiologic testing in the clinical microbiology laboratory at CHKD and organisms were recorded. The organisms were categorized as to whether the following were present or absent: *Pseudomonas aeruginosa, Staphylococcus aureus, Burkholderia cepacia* complex, or *Candida* species. Patient medications at the time of clinic visit were also recorded. Medications were categorized as to whether the following were present or absent: systemic corticosteroid, inhaled corticosteroid, azithromycin, inhaled antibiotic, or systemic antibiotic (excluding azithromycin).
Methods: ELISAs & Western Blots The C5a concentration in sputum sol was quantitated using a C5a ELISA kit (R&D Systems). C3a and C4a from sputum sol were both measured using their respective ELISA kits (BD Biosciences). Bound C3-fragments were determined using a total C3 ELISA. Briefly, a goat anti-human C3 antibody (Complement Technology) was used to coat flat-bottom Immulon-2 plates the night before. The plates were then washed with PBST (PBS with 0.1% TWEEN), blocked for two hours with 3% BSA/PBS, washed again, and followed by the addition of samples and a pure C3 standard (Complement Technology) for 1 hour in block buffer. Plates were washed, incubated with a chicken anti-human C3 antibody (Sigma) for 1 hour, washed again, and incubated with a goat anti-chicken HRP antibody (Genway). Plates were developed with TMB Substrate Solution (Thermo Scientific) and stopped with 2.5 N H2504 (Hair P S, Echague C G, Rohn R D, et al. "Hyperglycemic conditions inhibit C3-mediated immunologic control of *Staphylococcus aureus.*" *J Transl Med* 2012; 10:35]. Bound C4-fragments were evaluated with the same ELISA method as for C3, except using a goat anti-human C4 antibody to coat the plates, a pure C4 as the standard (both Complement Technologies), and a chicken anti-human C4 antibody (Abcam) as the primary antibody.

Figure 10C:
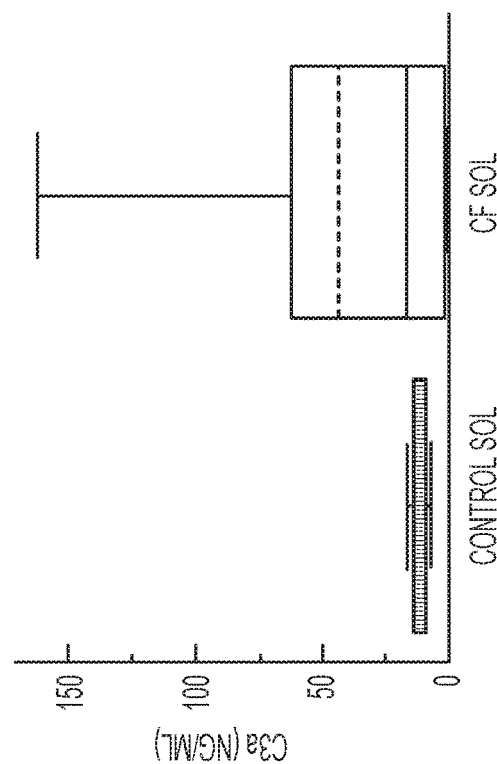
FIGS. 10A-D shows complement anaphylatoxins in CF and control lung fluid.
Figure 10D:
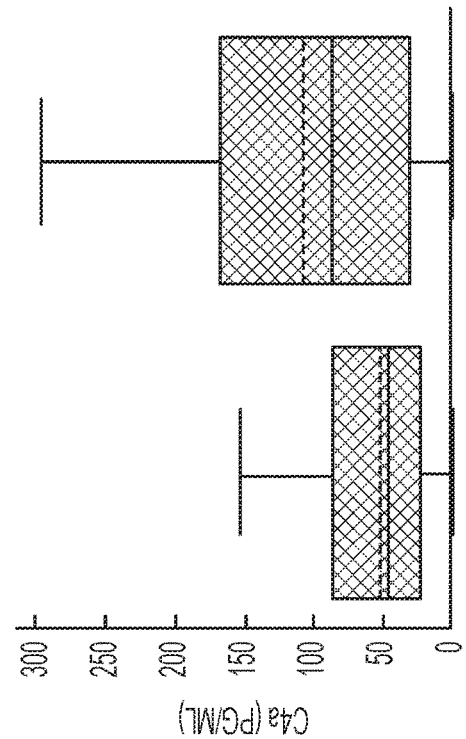
Figure 10A:
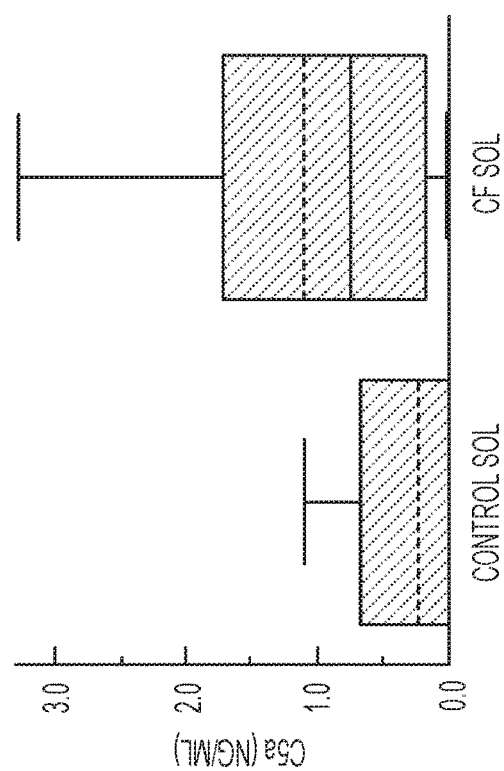
Figure 10B:
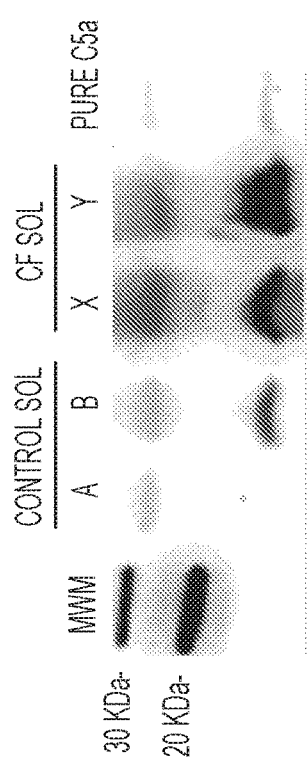

C5a fragments were analyzed by Western Blot using a mouse anti-human C5a antibody (R&D Systems) to probe followed by a goat anti-mouse HRP antibody (Sigma) and detected with ECL.
Results To evaluate whether complement anaphylatoxins were elevated in CF lung fluid, CF sols from the sputum of CF patients were assayed for each complement anaphylatoxin and compared with sputum sols from healthy human controls. The most inflammatory complement anaphylatoxin was C5a, which was assayed by ELISA and Western blot. Mean C5a concentration in CF sols was 4.8-fold higher (P=0.04) compared with the mean for healthy controls (FIG. 10A). Qualitative analysis by Western blot probing for C5a confirmed that large amounts of C5a were present in CF sols compared with controls (FIG. 10B). C3a is a complement effector that is generated during activation of the central complement component C3. Mean C3a concentrations in CF sols was 4-fold higher (P=0.03) compared with controls (FIG. 10C). C4a is the least potent of complement anaphylatoxins and is generated during classical or lectin pathway complement activation. Mean C4a concentration was 2-fold higher in CF sols (P=0.05) compared with controls (FIG. 10D). Together these data show that the concentration of complement anaphylatoxins in CF lung fluid was significantly elevated, suggesting significant complement activation in CF lung fluid. The potent ability of C5a to recruit neutrophils and stimulate degranulation [Lambris J D, Sahu A, Wetsel R A. "The chemistry and biology of C3, C4, and C5. In: Volanakis J E, Frank M M, (eds)." *The human complement system in health and disease.* New York: Marcel Dekker; 1998, 83-118; Mollnes T E, Brekke O L, Fung M, et al. "Essential role of the C5a receptor in *E coli*-induced oxidative burst and phagocytosis revealed by a novel lepirudin-based human whole blood model of inflammation." *Blood* 2002; 100(5):1869-77; Laursen N S, Magnani F, Gottfredsen R H, et al. "Structure, function and control of complement C5 and its proteolytic fragments." *Curr Mol Med* 2012; 12(8):1083-97], suggested that C5a could contribute to the high concentrations of neutrophil elastase in CF lung fluid, which is associated with parenchymal destruction. Additionally, the elevated levels of C4a in CF lung fluid, suggested that much of the complement activation occurring in CF lung fluid may be occurring via the classical or lectin complement pathways.

Example 11—Investigation of Complement Effectors of Inflammation in Cystic Fibrosis Lung Fluid—Complement Opsonization of *Staphylococcus aureus* in CF Lung Fluid Methods: *S. aureus* Opsonization With CF Sols

Figure 11A:
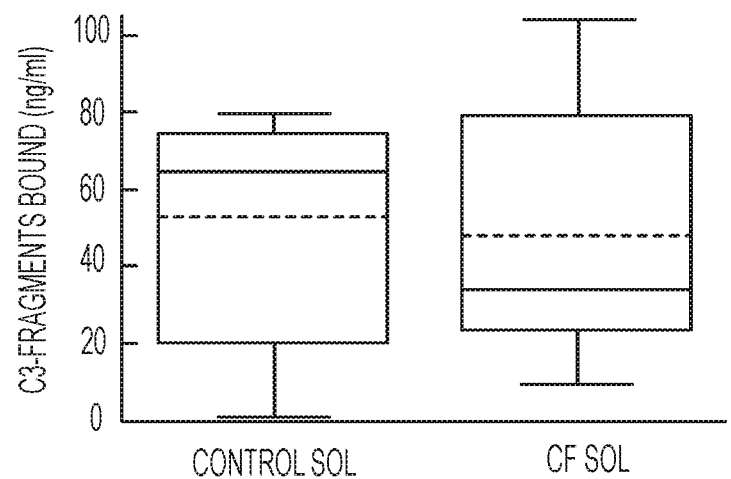
FIGS. 11A-B shows complement opsonization of *Staphylococcus aureus*.
Figure 11B:
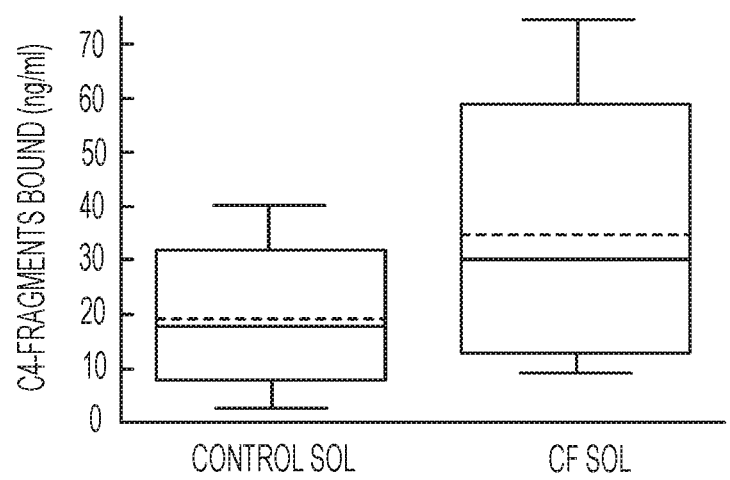

*Staphylococcus aureus* strain Reynolds was grown in 2% NaCl Columbia broth at 37° C. to log phase, washed twice with GVBS$^{++}$ (vernal buffered saline with 0.1% gelatin, 0.15 mM $CaCl_2$), and 1.0 mM $MgCl_2$), and resuspended to $1\times10^9$ cells/ml. An equal volume of bacteria and CF or control sol were incubated for one hour at 37° C. The bacteria were washed twice with GVBS$^{--}$ (VBS with 0.1% gelatin and 0.01 M EDTA), and then stripped of bound complement fragments using methylamine, as previously described [Cunnion K M, Lee J C, Frank M M. "Capsule production and growth phase influence binding of complement to *Staphylococcus aureus*." Infect Immun 2001; 69(11):6796-803]. Results In order to evaluate whether complement in CF lung fluid could adequately opsonize a pathogenic bacteria, CF sol opsonization of *Staphylococcus aureus* was evaluated. Given the large amounts of complement activation that had already occurred in the CF lung fluids, it was important to determine whether there was residual complement-mediated host defense. *Staphylococcus aureus* were incubated with CF or control sols, washed and stripped of bound C3-fragments and bound C4-fragments. *Staphylococcus aureus* was robustly opsonized in CF sol yielding a nearly identical mean level of bound C3-fragments compared with normal controls (FIG. 11A). *Staphylococcus aureus* was also robustly bound by C4-fragments (P=0.13) with a non-significant trend towards increased mean C4-fragment binding by CF sols compared with normal controls (FIG. 11B). These results suggested that CF lung fluid retained a normal capacity to opsonize bacteria, suggesting that this facet of host defenses is not compromised. These results also show that despite significant complement activation having occurred, as evident by very high anaphylatoxin levels, significant complement remains in CF lung fluid. This suggested a cycle of complement activation and repletion consistent with persistent inflammation. The robust opsonization with C4-fragments suggested that the classical or lectin complement pathway was active in CF lung fluid and may be the predominant pathway of complement activation.

Example 12—Investigation of Complement Effectors of Inflammation in Cystic Fibrosis Lung Fluid—C5a Generation in CF Lung Fluid by *Pseudomonas aeruginosa* and *Staphylococcus aureus*

*Pseudomonas aeruginosa* was acquired as a discarded de-identified clinical isolate. It was grown in Mueller Hinton broth to log phase and washed and re-suspended as was done with the *Staphylococcus aureus*. Both bacteria were gently heat killed by incubating in a 70° C. water bath for 15 minutes. Samples were plated to confirm that the bacteria were dead. CF or control sols were incubated with either live or dead *Pseudomonas aeruginosa* or *Staphylococcus aureus* at equal volumes for one hour at 37° C. Afterward, the samples were spun at 14,000×g for 5 minutes and the supernatant was collected and analyzed for C5a. Equal volume of CF sol and PA-dPEG24 (SEQ ID NO: 21) [Shah et al. "Clinical hypothermia temperatures increase complement activation and cell destruction via the classical pathway." *J Transl Med* 2014; 12:181; Mauriello C T, Pallera H K, Sharp J A, et al. "A novel peptide inhibitor of classical and lectin complement activation including ABO incompatibility."*Mol Immunol* 2012; 53(1-2):132-9], at 50 mg/ml, or saline for controls, were combined and pre-incubated for 30 minutes at room temperature. Afterward, $5\times10^7$ CFU heat-killed *Pseudomonas aeruginosa* were added and incubated at 37° C. for 30 minutes. The samples were then spun at 14,000×g for 2 minutes and the supernatant was collected and assayed in the C5a ELISA.

Figure 12B:
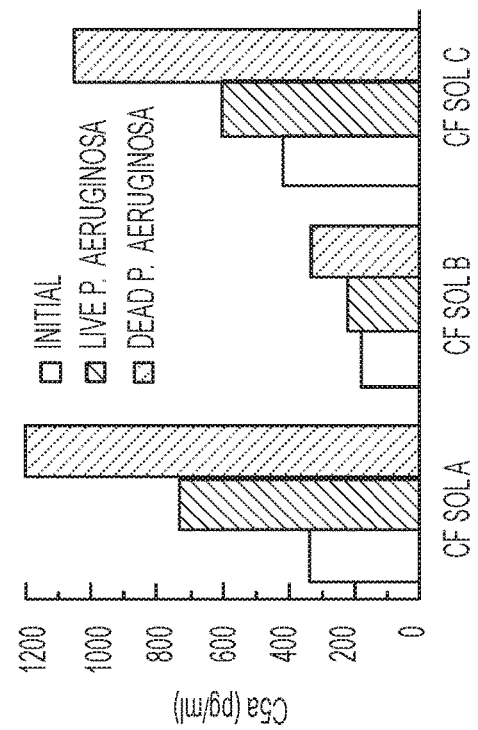
FIGS. 12A-D shows C5a generated by bacteria in CF sols.
Figure 12D:
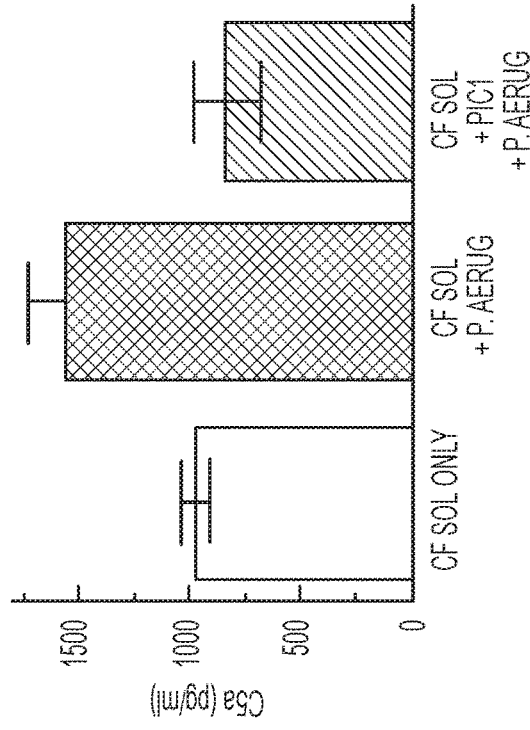
Figure 12A:
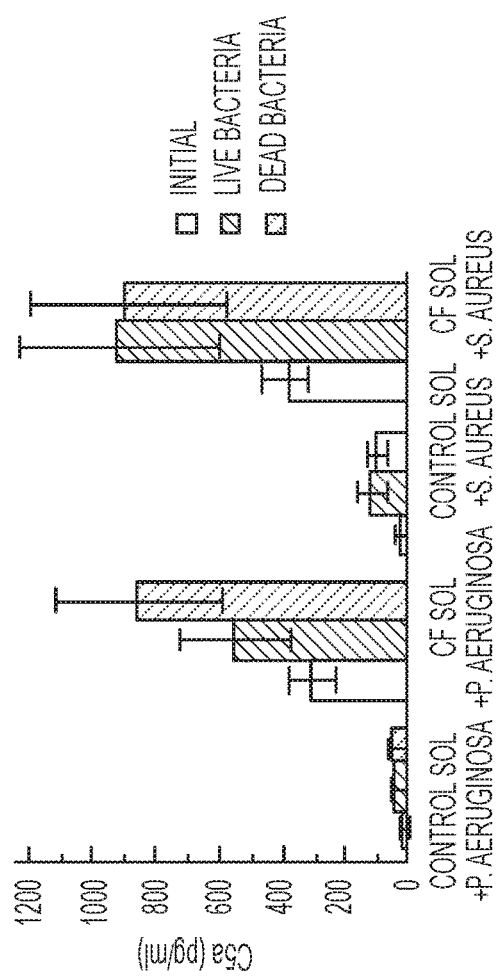
Figure 12C:
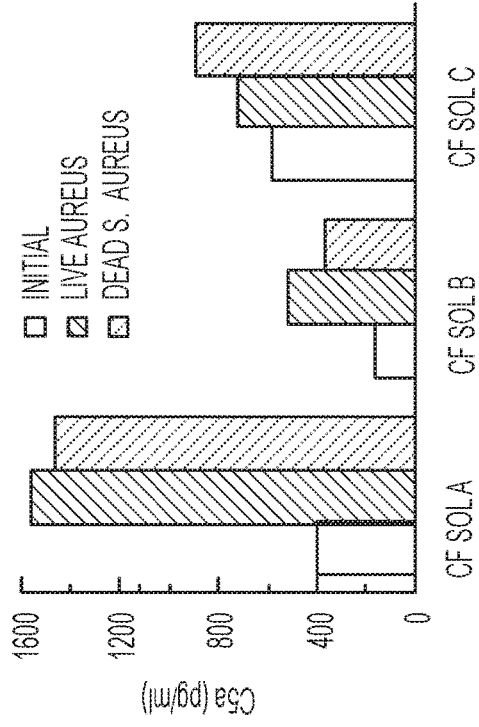

In order to evaluate whether CF lung fluid challenged with pathogenic bacteria commonly present in CF lungs would generate new C5a, the most inflammatory anaphylatoxin, CF sols were incubated with live and dead *Pseudomonas aeruginosa* and *Staphylococcus aureus*. Live and dead versions of each bacteria were tested because both forms are likely to be present in an infected CF lung. Additionally, secreted factors or adaptive changes that could be produced by live bacteria would also alter C5a generation. Before and after incubation with bacteria, C5a concentrations were measured in CF to determine if new C5a were generated. Incubation of CF sols with live or dead *Pseudomonas aeruginosa* lead to an average increase in C5a generation of 2.3-fold (P=0.02). Similarly, incubation with live or dead *Staphylococcus aureus* lead to an average increase in C5a generation of 2.4-fold (P=0.02) (FIG. 12A). These data also showed a difference in C5a generation between live or dead *Pseudomonas aeruginosa* (P=0.05), but not between live or dead *Staphylococcus aureus*. This relationship between live or dead *Pseudomonas aeruginosa* challenge appeared consistent for the different CF sol samples (FIG. 12B), but there was no consistent relationship between live or dead *Staphylococcus aureus* challenge (FIG. 12C). These data showed that *Pseudomonas aeruginosa* and *Staphylococcus aureus* both provoke robust generation of the highly inflammatory C5a anaphylatoxin in CF lung fluid, suggesting that the presence of these bacteria in the CF lung may be enhancing inflammation and subsequent host tissue damage. *Pseudomonas aeruginosa* may have some ability to moderate C5a generation in CF lung fluid compared to dead *Pseudomonas aeruginosa*.

In order to evaluate the likely complement pathways by which *Pseudomonas aeruginosa* was activating C5a generation, an inhibitor of classical and lectin complement pathway activation was tested. Peptide inhibitors of complement C1 are small peptide inhibitors of the classical and lectin pathways of complement activation CF sols were incubated in buffer alone, with dead *Pseudomonas aeruginosa*, or with PA-dPEG24 (SEQ ID NO: 21) and dead *Pseudomonas aeruginosa* (FIG. 12D). Dead *Pseudomonas aeruginosa* increased C5a concentration by 1.6-fold compared to incubation of the CF sol in buffer alone. Addition of PA-dPEG24 (SEQ ID NO: 21) to the CF sol decreased C5a generation by *Pseudomonas aeruginosa* (P=0.001) to a level not significantly different from CF sol alone (P=0.22). Thus, addition of a classical/lectin pathway inhibitor blocked C5a generation by *Pseudomonas aeruginosa*, suggesting that *Pseudomonas aeruginosa* activates complement and C5a generation via the classical or lectin complement pathways. This finding was congruent with elevated C4a levels and robust C4-fragment opsonization.

Example 13—Investigation of Complement Effectors of Inflammation in Cystic Fibrosis Lung Fluid—Complement Anaphylatoxin Correlation with Clinical Characteristics Methods: Statistical Analysis of Clinical Measures with C5a/C3a and of Laboratory Data The data were analyzed using SAS 9.4 (SAS Institute, Cary, N.C.) and SPSS 19 (SPSS Inc., Chicago, Ill.) software.

The level of significance was set at 0.05. Pearson and Spearman correlation coefficients were reported, where appropriate, for C5a level, C3a level, and the clinical measures. Descriptive statistics were reported for C5a and C3a level stratified by clinical measures. Simple linear regression and Mann-Whitney U tests were used, where appropriate, to determine associations between C5a level, C3a level, and the clinical measures. A multivariable linear regression model for FEV1% was used to determine associations with C5a level and C3a level.

Medians, quartiles, and 90$^{th}$ percentiles were calculated using PSI plot. Means and standard error of the means (SEM) were calculated from independent experiments. Statistical comparisons were made using Student's t-test where appropriate with a level of significance set at 0.05.

Results

Figure 13A:
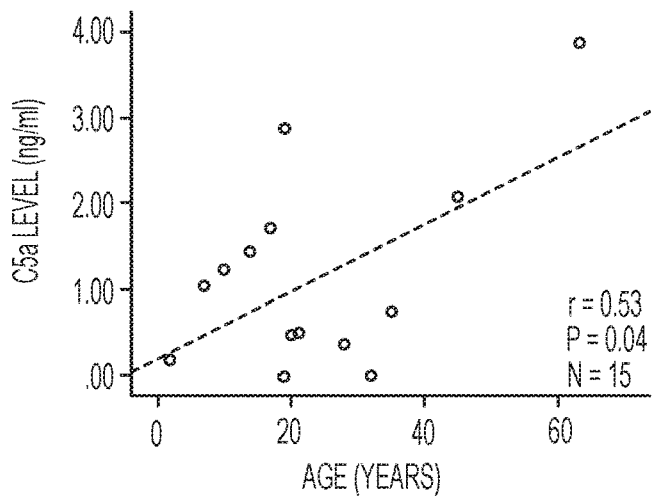
FIGS. 13A-C shows correlation plots for complement effectors and clinical measures.
Figure 13B:
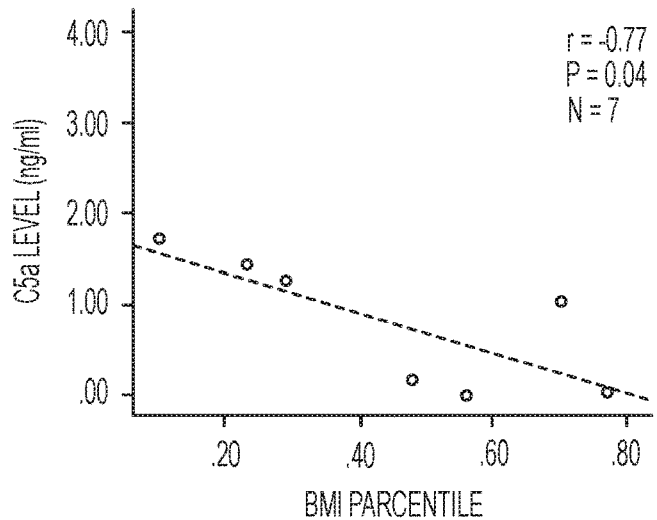
Figure 13C:
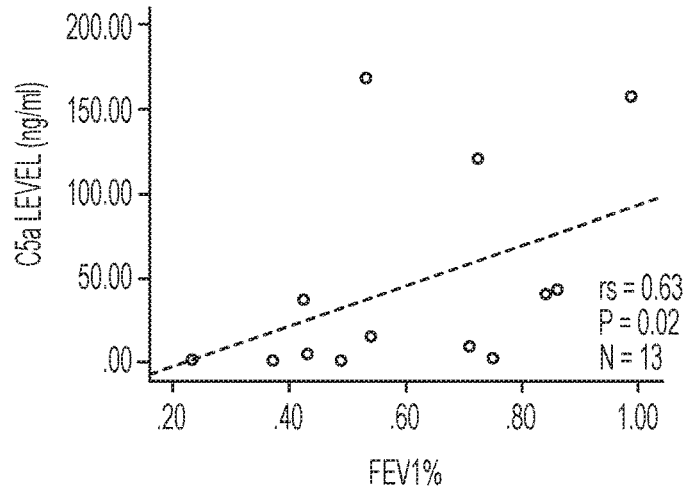

CF sputum samples were collected from 15 patients. The clinical characteristics of these 15 subjects is shown in TABLE 9. The subjects span a wide range of ages from 2-65 years old with a median age of 19. Median FEV1% predicted was 59; for children (n=7) the median BMI was 48% and for adults (n=4) the median BMI was 23.87 mg/kg$^2$. Clinical data collected at the time of sputum sampling was obtained for a wide range of measures including FEV1% predicted, BMI percentage (children), bronchiectasis, CFRD status, pathogenic microorganisms cultured from the sputum and medications (i.e. corticosteroids, azithromycin, and antibiotics). Statistical correlations were assessed between the anaphylatoxins, C5a and C3a, and the clinical measures, see TABLE 10. Increased concentration of the highly inflammatory C5a positively correlated with increased age (r=0.53, P=0.04), as shown in FIG. 13A. Increased C5a concentration correlated inversely with BMI percentile in children (r=−0.77, P=0.04) as shown in FIG. 13B. Increased C3a levels positively correlated with increased FEV1% predicted ($r_s$=0.63, P=0.02), as shown in FIG. 13C. Microorganisms (i.e. *Pseudomonas aeruginosa, Burkholderia cepacia, Staphylococcus aureus*, or yeast) recovered from the sputum, corticosteroids, azithromycin, or antibiotics did not correlate with levels of C5a or C3a. These results showed that increasing C5a concentration correlated with decreased BMI percentile in children, suggesting that increased complement inflammatory C5a in lung fluid may be associated with poorer overall health in children with CF. C3a level positively correlated with FEV1% predicted, suggesting a potentially protective effect from C3a on CF lung function.

TABLE 9

Characteristics of the CF subjects.

| | Median (range) |
|---|---|
| Age, y | 19 (2-65) |
| Gender, % female | 60 |
| Child BMI, % | 26 (10-70) |
| Adult BMI | 23.8 (21.8-25.9) |
| FEV1% | 59 (23-99) |

TABLE 10

Correlation coefficients for complement effectors and clinical measures

| | | C5a (ng/ml) | C3a (ng/ml) |
|---|---|---|---|
| Correlation coefficient | Age, y | 0.53$^a$ | −0.12$^b$ |
| P value (H$_0$: rho = 0) | | 0.04 | 0.68 |
| N | | 15 | 14 |
| Correlation coefficient | Child BMI, % | −0.77$^a$ | −0.39$^b$ |
| P value (H$_0$: rho = 0) | | 0.04 | 0.38 |
| N | | 7 | 7 |
| Correlation coefficient | FEV1% | 0.04$^a$ | 0.63$^b$ |
| P value (H$_0$: rho = 0) | | 0.89 | 0.02 |
| N | | 14 | 13 |
| Correlation coefficient | Bronchiectasis Score | 0.12$^b$ | 0.15$^b$ |
| P value (H$_0$: rho = 0) | | 0.68 | 0.61 |
| N | | 15 | 14 |
| Correlation coefficient | CFRD Score | 0.27$^b$ | 0.01$^b$ |
| P value (H$_0$: rho = 0) | | 0.38 | 0.98 |
| N | | 13 | 12 |

Bronchiectasis score: 0 = normal; 1 = 1 lobe, mild; 2 = 2-4 lobes; 3 = all lobes
CFRD score: 0 = normal; 1 = glucose intolerance; 2 = CFRD
$^a$Pearson correlation coefficient
$^b$Spearman correlation coefficient Example 14—Modulation of C1q Interaction with C1q Receptors—Binding to Calreticulin Receptor Methods To demonstrate that PA blocks binding to the calreticulin receptor, the following experiment was performed. Recombinant calreticulin or BSA (negative control) was used to coat a microtiter plate. C1q was then added to the plate alone was incubated with increasing amounts of PA peptide (SEQ ID NO: 3) and then assessed for binding to calreticulin. As a negative control, a 15 amino acid peptide (CP2) that does not bind C1q was used.

The interaction of labeled C1q with Raji cells was tested by confocal microscopy. Labeled C1q was added to Raji cells. 1.4125×10$^6$ cells/ml were fixed with 4% paraformaldehyde for 5 min and stored over-night at 4° C. 1×10$^5$ cells stained with: 1:40 C1q 488 for 20 min, washed ×2, and stained with DAPI mounting medium, and stored over-night at 4° C.

PA-dPEG24 (SEQ ID NO: 21) was pre-incubated with C1q at two different concentrations before adding to Raji cells. 1.4125×10$^6$ cells/ml were fixed with 4% paraformaldehyde for 5 minutes and stored over-night at 4° C. 1×10$^5$ cells stained with: 1:40 C1q 488 plus 1.45 mg/ml PA-dPEG24 (SEQ ID NO: 21) (1:20 of 29 mg/ml) or 2.9 mg/ml PA-dPEG24 (SEQ ID NO: 21) (1:10 of 29 mg/ml) for 20 minutes, washed twice, stained with DAPI mounting medium, and stored overnight 4° C.

Results

PA-dPEG24 (SEQ ID NO: 21) blocked C1q binding to a specific C1q cell receptor (calreticulin/cC1qR) in an in vitro assay and also blocked binding of C1q to Raji cells (an immortalized B lymphocyte cell line that is used for evaluating C1q interactions with C1q receptors).

Figure 14A:
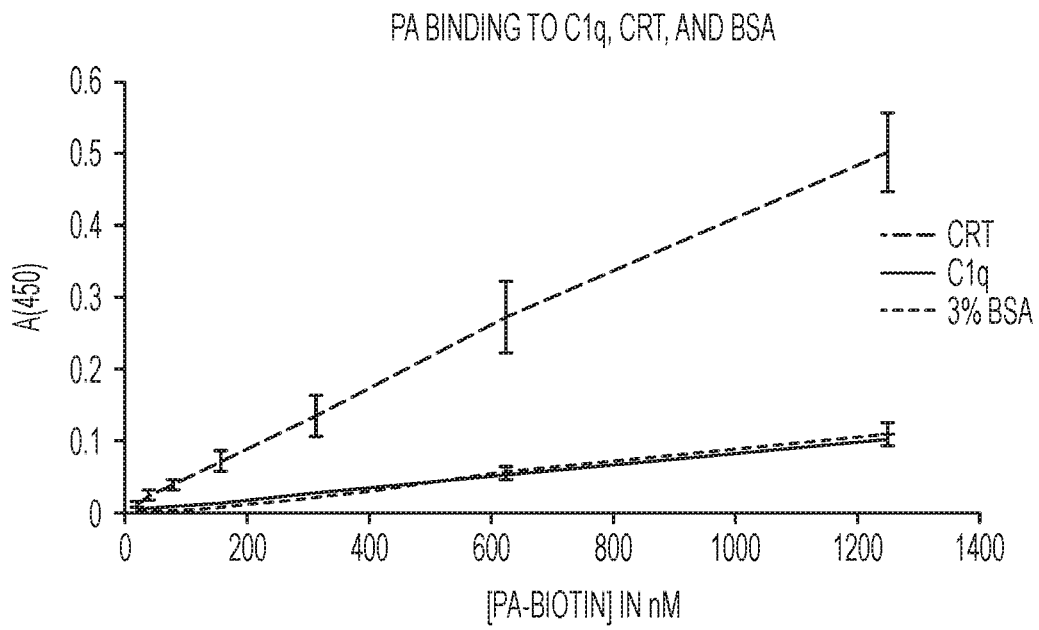
Figure 14B:
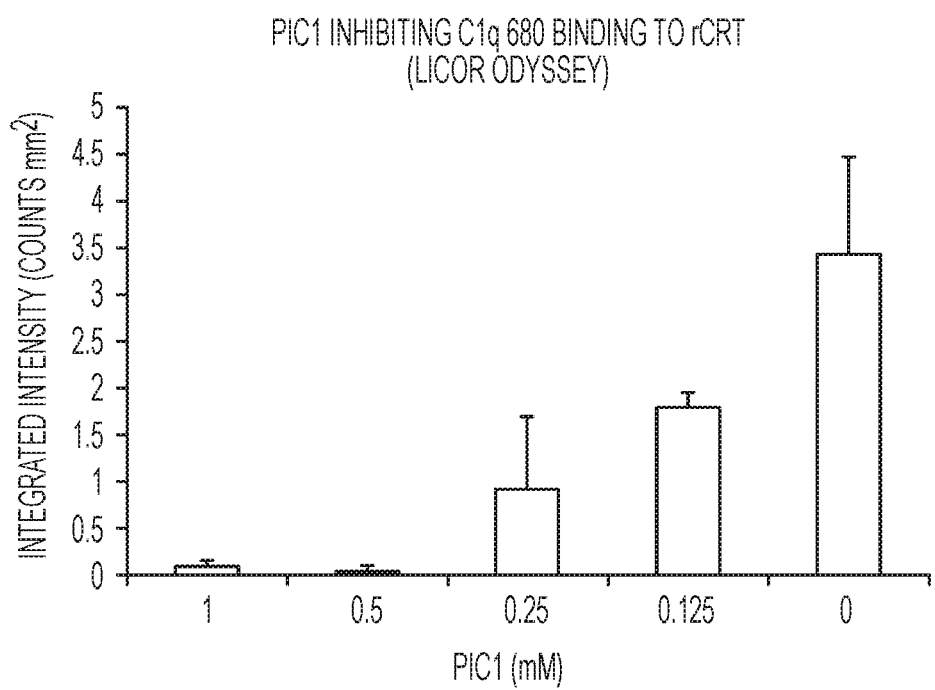
Figure 15:
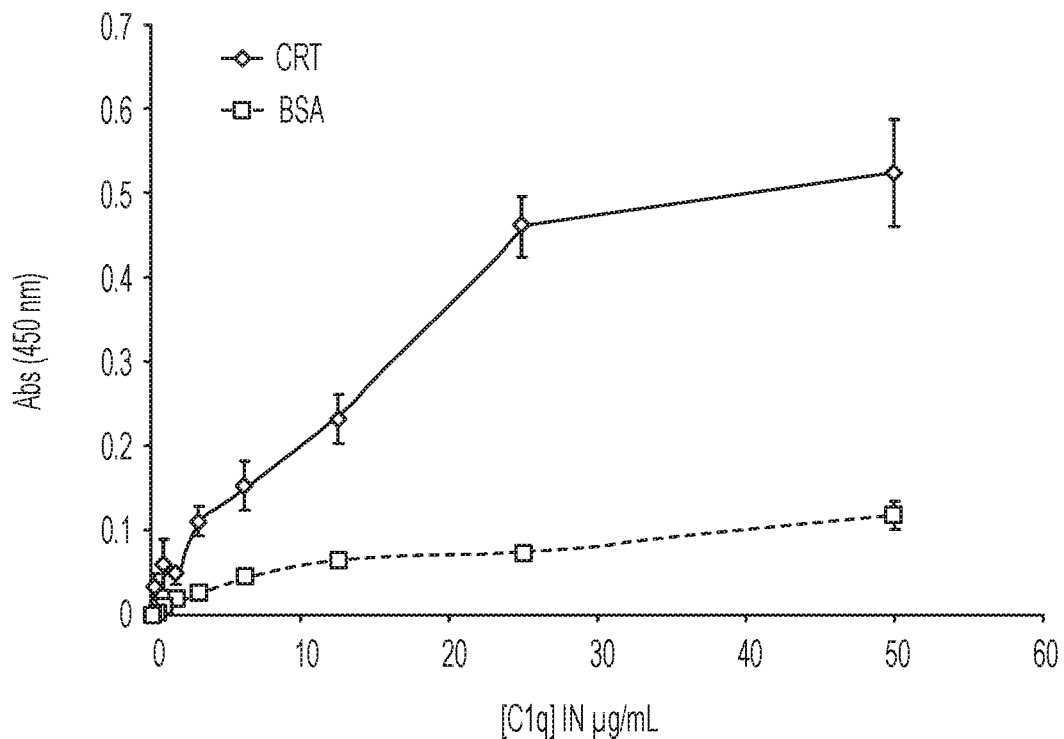
FIG. 15 shows soluble C1q binding calreticulin (CRT), but not BSA.
Figure 16:
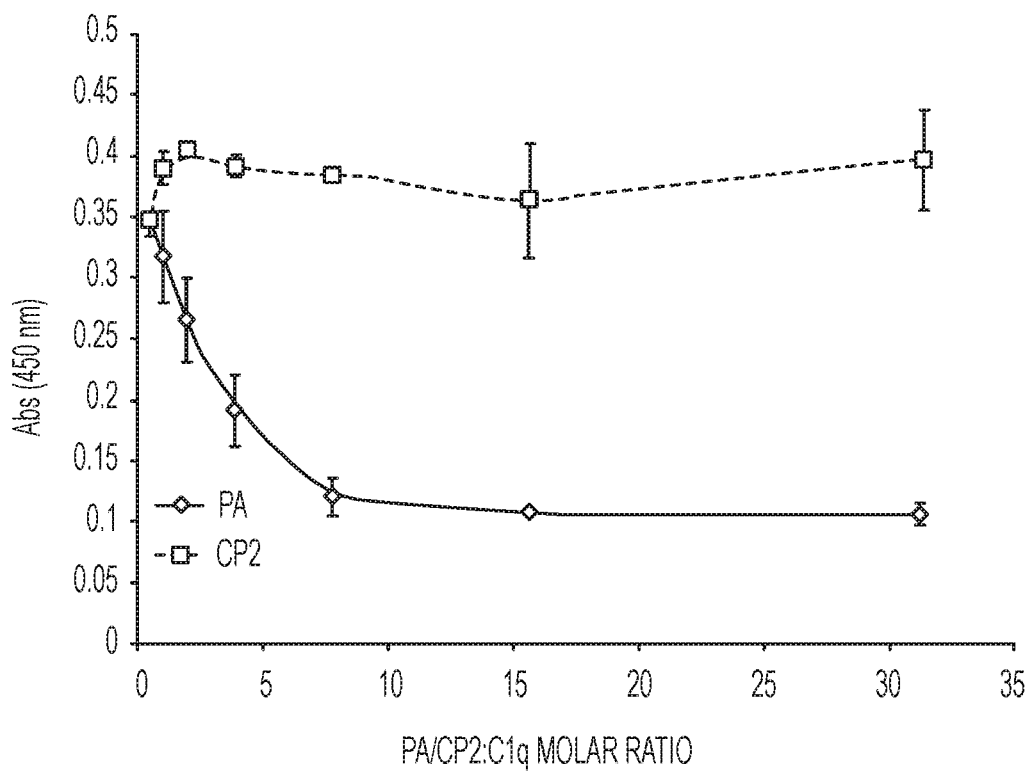
FIG. 16 shows PA (SEQ ID NO: 3) inhibiting C1q binding to calreticulin (CRT) compared to a negative control peptide CP2.

C1q was added to a plate coated with calreticulin, the results showed that C1q binds specifically to calreticulin but not BSA, as expected (FIG. 15). When plates were coated with C1q, calreticulin and BSA, PA peptide (SEQ ID NO: 3) bound specifically to C1q, the interaction between PA was specific for C1q and not calreticulin or BSA (FIG. 14A). When C1q was incubated with increasing amounts of PA peptide (SEQ ID NO: 3) and then assessed for binding to calreticulin, PA dose-dependently inhibited binding to calreticulin (FIG. 16). As a negative control, a 15 amino acid peptide (CP2) that does not bind C1q did not show competitive inhibition of C1q binding to calreticulin (FIG. 16). Additionally, PA (SEQ ID NO: 3) inhibited C1q binding to purified calreticulin (FIG. 14B) and Raji cells (FIG. 14C-D) consistent with inhibition of C1q binding to surface CRT. The experiment setup is show in FIG. 14E.

Figure 17A:
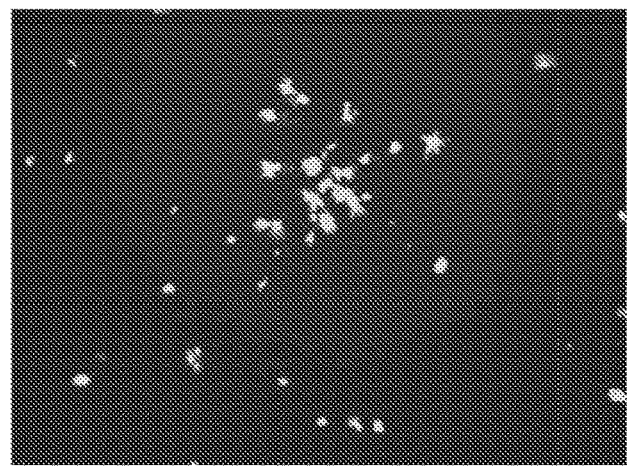
FIGS. 17A-C shows Raji cells at 20× magnification.
Figure 17B:
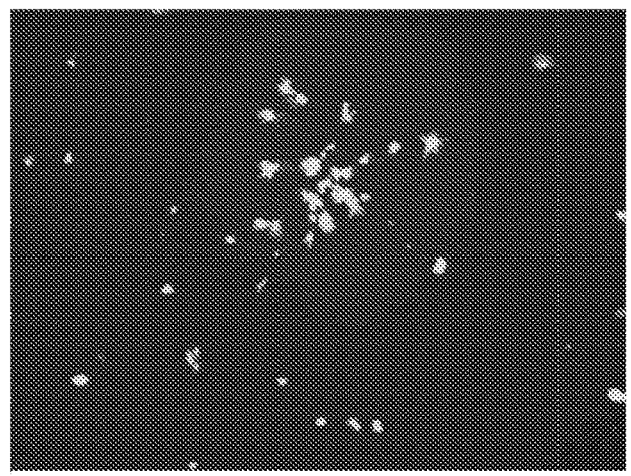
Figure 17C:
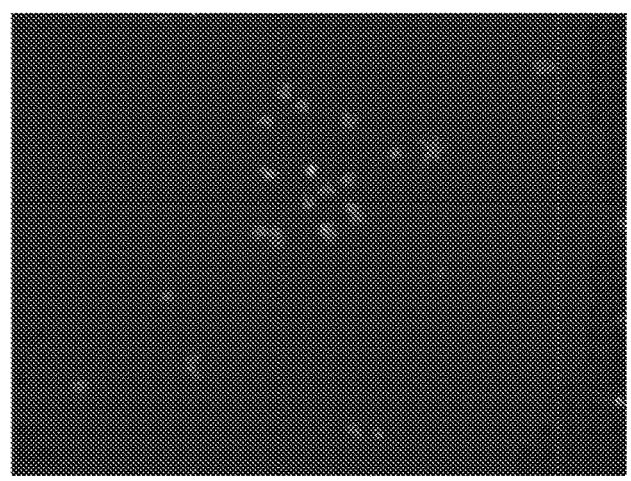
Figure 18A:
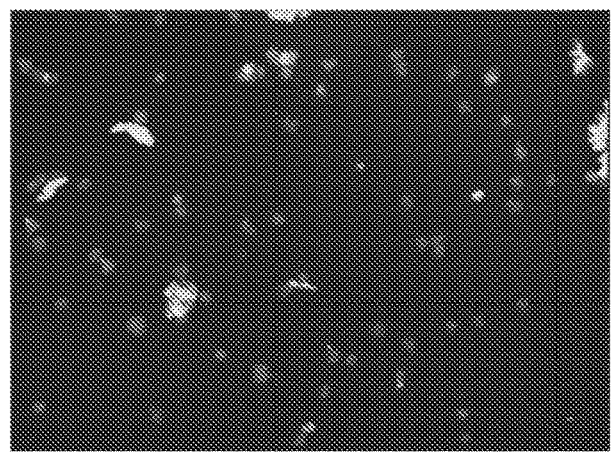
FIGS. 18A-C shows Raji cells at 20× magnification treated with 0.523 mM PA-dPEG24 (SEQ ID NO: 21).
Figure 18B:
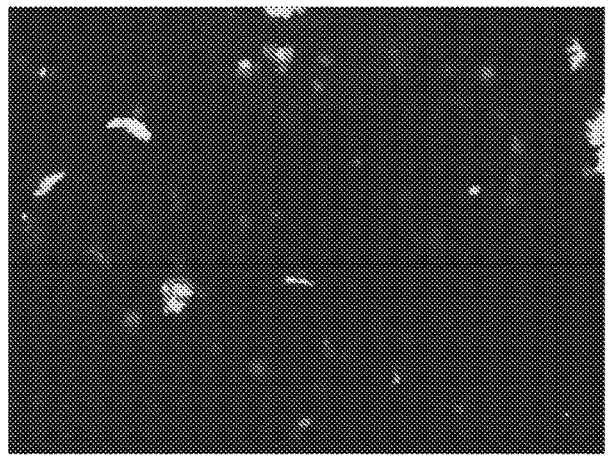
Figure 18C:
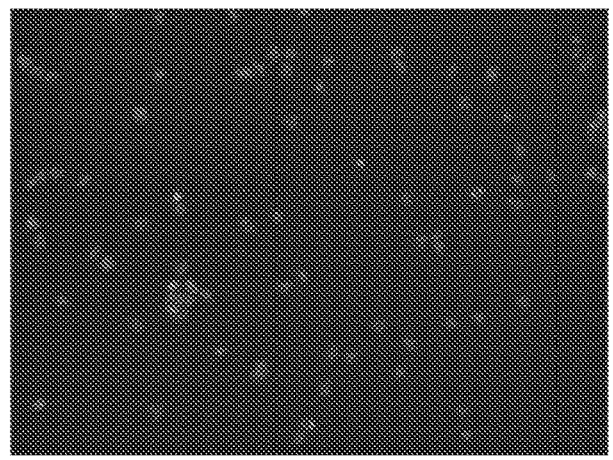
Figure 19A:
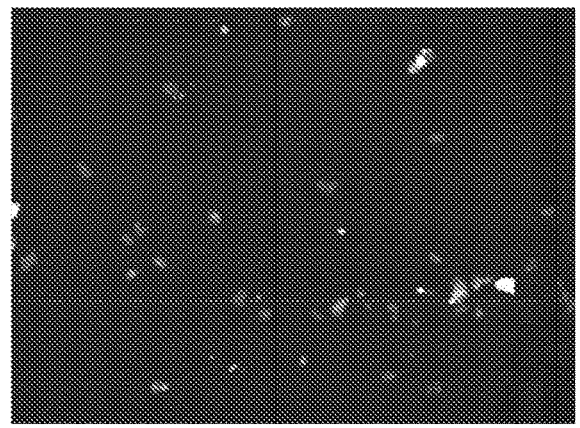
FIGS. 19A-C shows Raji cells at 20× magnification treated with 1.05 mM PA-dPEG24 (SEQ ID NO: 21).
Figure 19B:
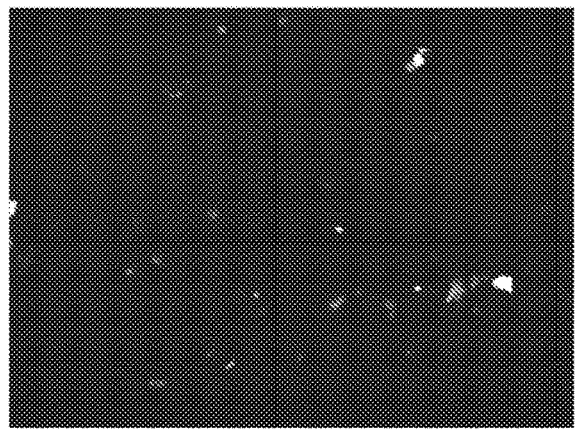
Figure 19C:
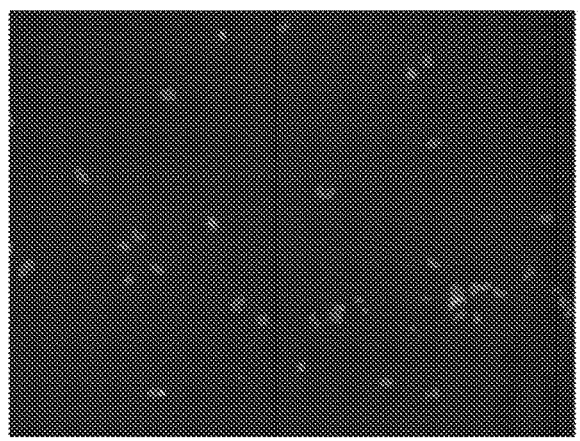

The interaction of labeled C1q with Raji cells was investigated by confocal microscopy. Labeled C1q (FITC) bound to Raji cells (DAPI) as shown in FIGS. 17A-C. When PA-dPEG24 (SEQ ID NO: 21) was preincubated with C1q at two different concentrations, the amount of labeled C1q bound to Raji cells decreased significantly (FIGS. 18A-C and 19A-C), demonstrating that (SEQ ID NO: 21) inhibited binding of C1q to these cells. Although not bound by any theory, (SEQ ID NO: 21) presumably inhibited binding of C1q by disrupting C1q interaction with a C1q receptor(s) on the cell surface.

Example 15—Peptide Compounds Significantly Reduced Brain Injury in a Rat Model of Neonatal Hypoxic Ischemic Encephalopathy Methods P10 Wistar rat pups were subjected to unilateral right carotid ligation (Vannucci model) followed by 8% hypoxia. Experimental animals were injected with 150 mg/kg PA-dPEG24 (SEQ ID NO: 21) intraperitoneally. Controls included 1) cobra venom factor (CVF) injection to deplete complement 2) therapeutic hypothermia for 6 hours. Animals were harvested at 4, 8, 16 and 48 hours after intervention. CH50 assay was performed on rat plasma to measure systemic complement activity. Cerebral infarct volumes were measured by staining harvested brain tissue with 2% TTC using image J software.

Results

Figure 30:
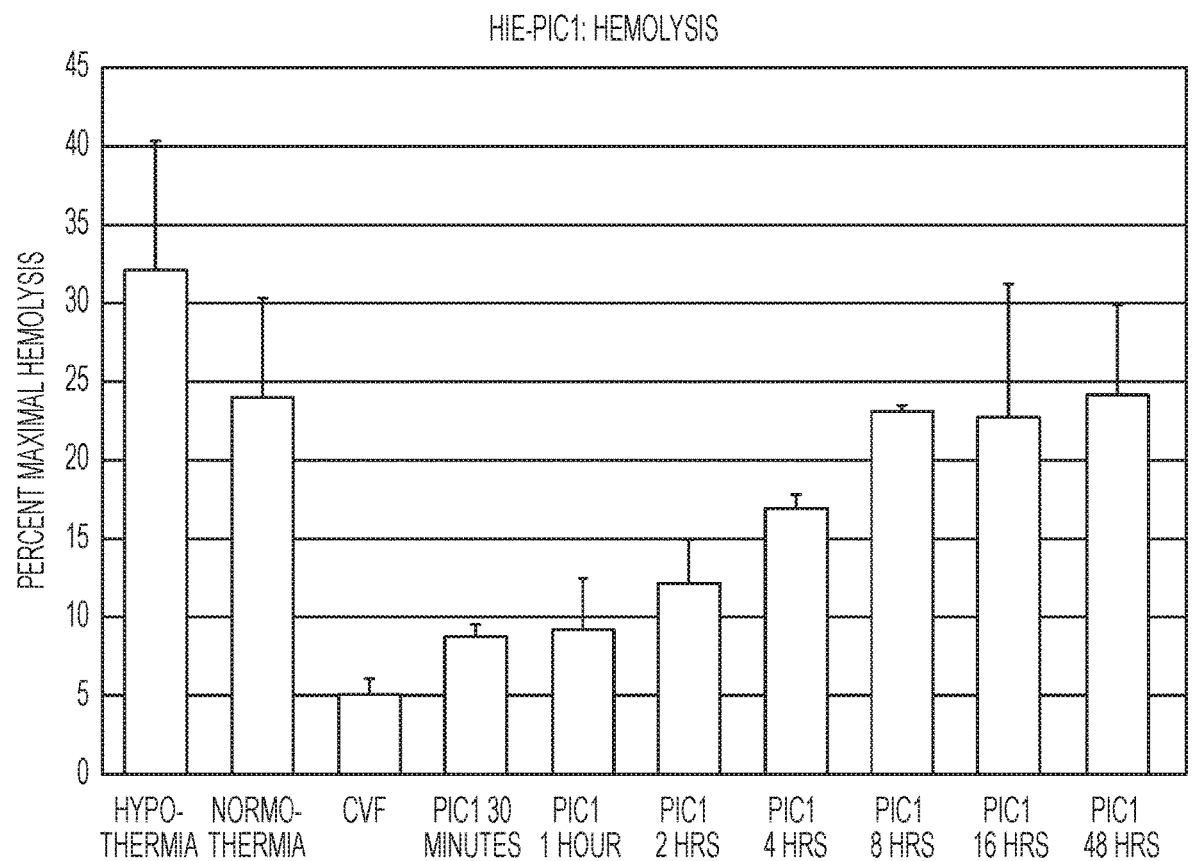
FIG. 30 shows percent maximal serum hemolysis after hypoxia in rats at 1, 2, 4, 8, 16, 24, 48 hours post-treatment with PIC1 (PA-dPEG24) (SEQ ID NO: 21), cobra venom factor (CVF), or therapeutic hypothermia (31-32° C. for 6 hours).
Figure 31:
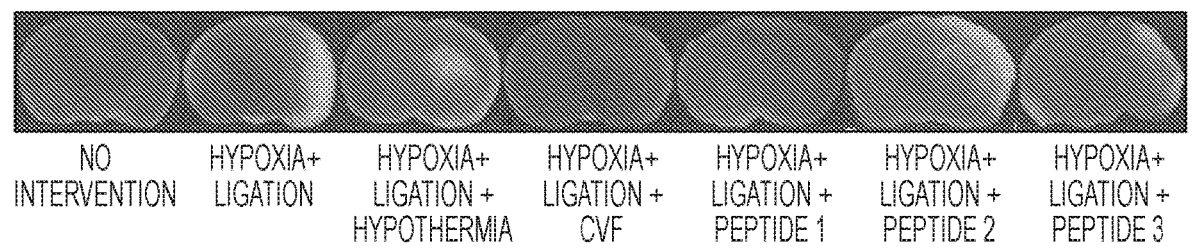
FIG. 31 shows images of brain slices after hypoxia in rats treated with PIC1 peptide (PA-dPEG24), cobra venom factor (CVF) therapeutic hypothermia (31-32° C. for 6 hours).
Figure 32A:
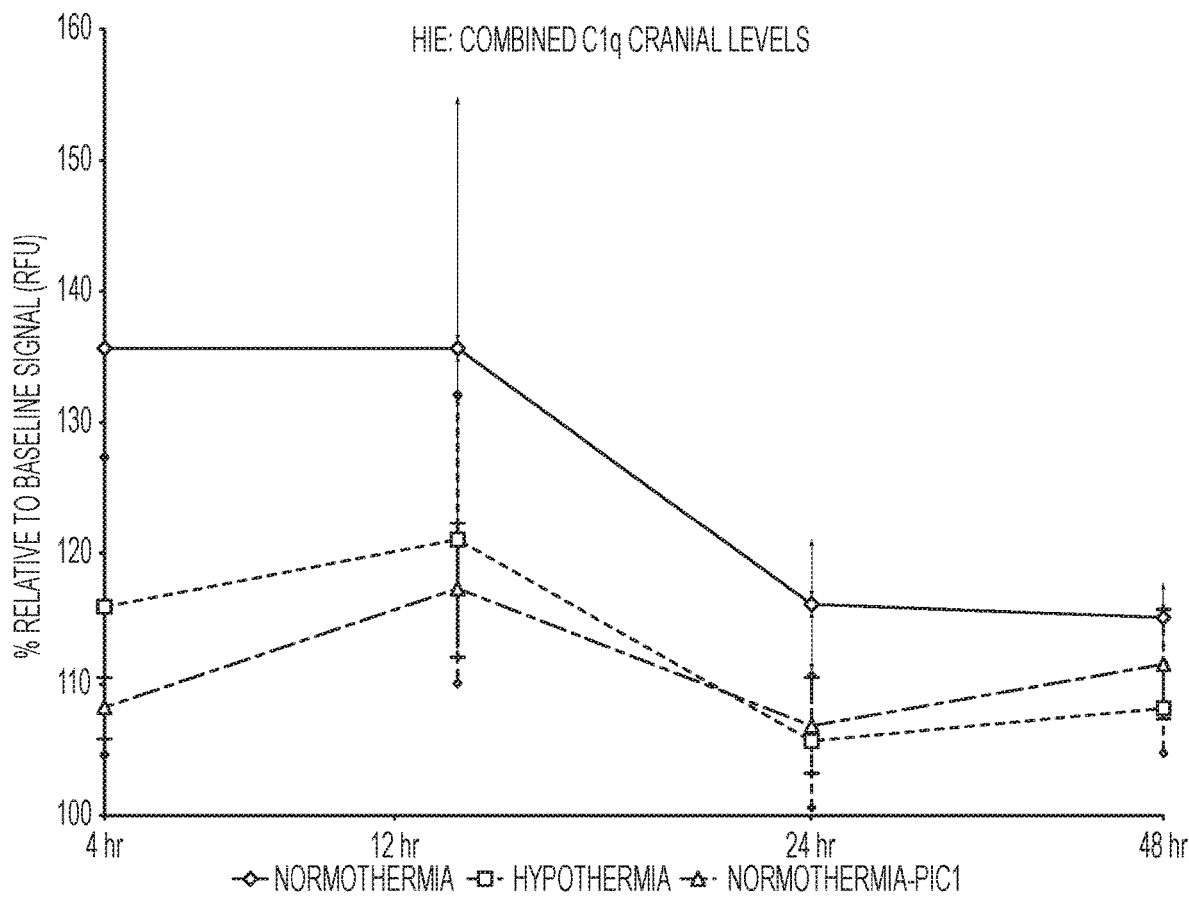
FIG. 32A shows combined C1q cranial levels in HIE. There is significantly less C1q deposition in the PIC1 (SEQ ID NO: 21) treated group (Normothermia+PIC1 (SEQ ID NO: 21)–triangle) when compared to untreated HIE controls (Normothermia–diamond) at 4, 12, and 24 hours after brain injury. PIC1 (SEQ ID NO: 21) treated animals had similar levels of C1q compared to animals who underwent therapeutic hypothermia (square).

Systemic complement activity was almost completely eliminated in animals injected with CVF for 72 hours after injection as expected. In the PA-dPEG24 (SEQ ID NO: 21) group, systemic complement activation was decreased by 70% at 0.5 hours after injection before gradually returning to baseline at 8 hours (FIG. 30). Hypoxia after carotid ligation yielded 20% infarction. CVF injection before ligation/hypoxia almost completely attenuated brain injury. HT reduces infarction by 50%. Injection with PA-dPEG24 (SEQ ID NO: 21) showed variable neuroprotection (FIG. 31) with an average reduction in infarction by 40%. Although not bound by any theory, SEQ ID NO: 21 may mimic the neuroprotective effect of therapeutic hypothermia by decreasing C1q deposition in the brain up to 48 hours. There was significantly less C1q deposition in the SEQ ID NO: 21 treated group (Normothermia+PIC1 (SEQ ID NO: 21)-triangle) when compared to untreated HIE controls (Normothermia–diamond) at 4, 12, 24 hours after brain injury (FIG. 32A).

Figure 32B:
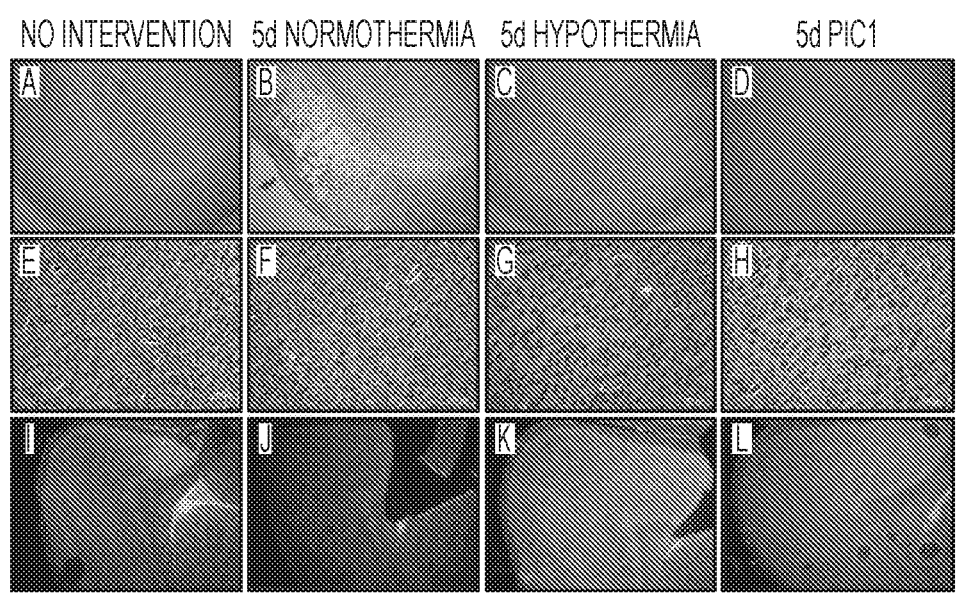
FIG. 32B shows evidence of neuroprotection post-HIE with PIC1 (SEQ ID NO: 21) treatment. Panels A-D of FIG. 32B show cresyl violet staining. Cresyl violet stains Nissl substance in neurons. The HIE group (Panel B) shows a significant decrease in cresyl violet staining compared to the PIC1 (SEQ ID NO: 21) group (Panel D), indicating the neuro-preservatory action of PIC1 (SEQ ID NO: 21) similar to therapeutic hypothermia (Panel C). Panels E-H show hematoxylin and eosin staining. Hematoxylin and Eosin staining demonstrated a greater degree of neuronal destruction (necrosis, pyknosis and karyorrhexis) in the HIE brain (Panel F) when compared to those treated with PIC1 (SEQ ID NO: 21) (Panel H). Panels I-L show acridine orange staining. Acridine orange stains viable parts of the brain a bright green (Panels K and L). HIE significantly decreases acridine orange staining in the brain (Panel J). PIC1 (SEQ ID NO: 21) treatment restored acridine orange staining, indicating the presence of more viable cells in the brain (Panel L).

SEQ ID NO: 21 also showed histological evidence of neuroprotection after HIE. Brain histology five days after HIE showed the neuro-preservatory action of SEQ ID NO: 21 similar to therapeutic hypothermia. Neuronal destruction was reduced in those treated with SEQ ID NO: 21, and the treatment also increased viable cells in the brain (FIG. 32B). For instance, in FIG. 32B, Panels A-D show cresyl violet staining. Cresyl violet stains Nissl substance in neurons. The HIE group (Panel B) shows a significant decrease in cresyl violet staining compared to the SEQ ID NO: 21 group (Panel D), indicating the neuro-preservatory action of SEQ ID NO: 21 similar to therapeutic hypothermia (Panel C). Panels E-H show hematoxylin and eosin staining. Hematoxylin and Eosin staining demonstrated a greater degree of neuronal destruction (necrosis, pyknosis and karyorrhexis) in the HIE brain (Panels E, F, and G) when compared to those treated with SEQ ID NO: 21 (Panel H). Panels I-L show acridine orange staining. Acridine orange stains viable parts of the brain a bright green. HIE significantly decreases acridine orange staining in the brain (Panel J). SEQ ID NO: 21 treatment restores acridine orange staining, indicating the presence of more viable cells in the brain (Panel L).

Figure 32C:
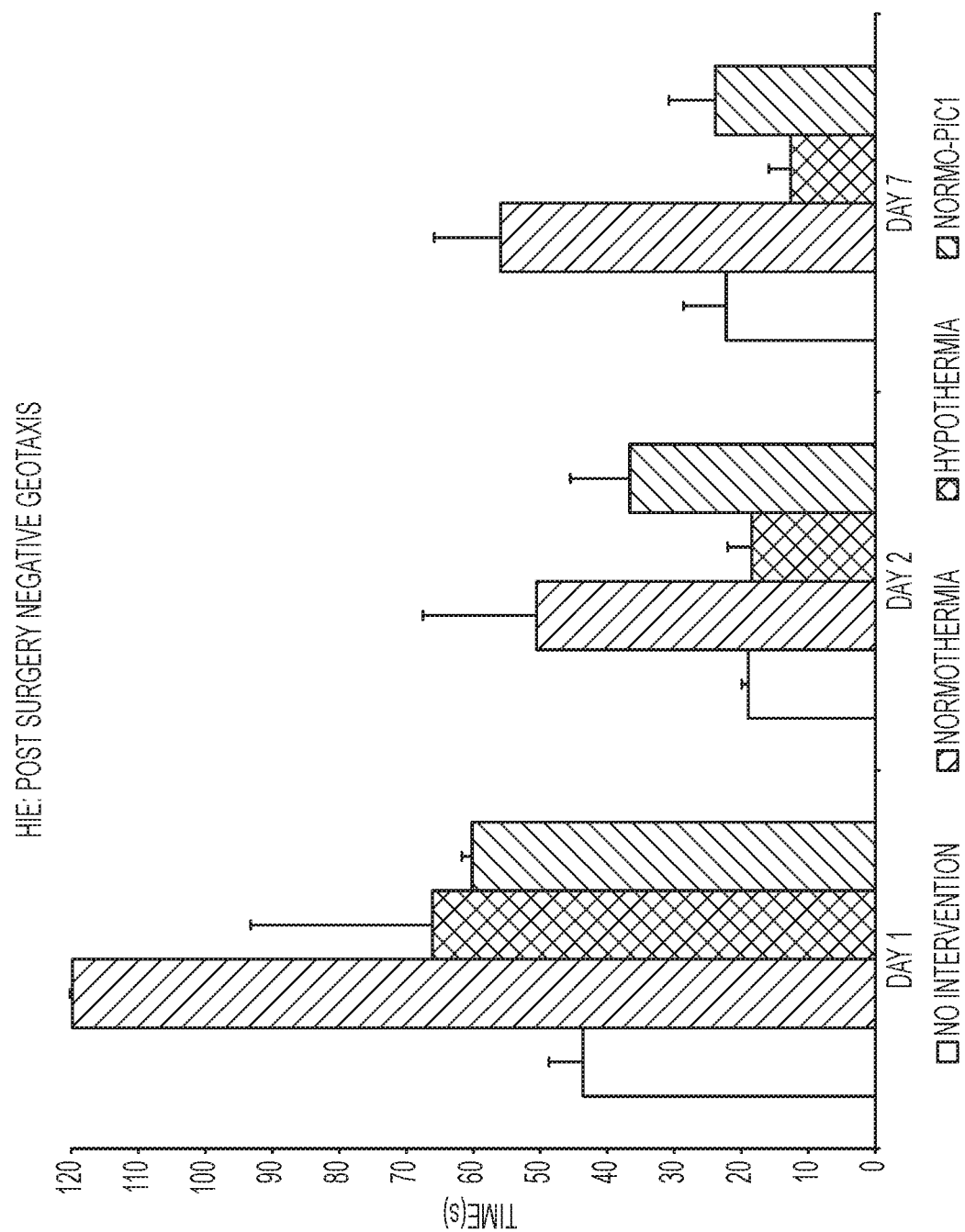
FIG. 32C shows histological neuroprotection also translated into neurofunctional improvement after HIE. Animals injected with PIC1 (SEQ ID NO: 21) performed better than normothermic animals and similar to no-intervention animals or animals receiving therapeutic hypothermia (No intervention, first bar on the left; HIE: Normothermia, second bar from left; HIE+ therapeutic hypothermia: Hypothermia, third bar from left, HIE+PIC1 (SEQ ID NO: 21): Normo–PIC1 (SEQ ID NO: 21), fourth bar from left).

Histological neuroprotection also translated into functional improvement after HIE. In a negative geotaxis test 1-7 days after HIE, animals injected with PIC1 (SEQ ID NO: 21) performed significantly better (FIG. 32C, green bars) than normothermia HIE animals (FIG. 32C, red bars). The negative geotaxis test is an innate escape response test measuring the time it takes for a pup to climb up when placed head down on a wire mesh.

This data showed that SEQ ID NO: 21 can reduce brain infarct volumes without prolonged systemic complement depletion, and improved functional outcomes after HIE. Although not bound by any theory, SEQ ID NO: 21 may have decreased C1q deposition in the brain. In some embodiments, SEQ ID NO: 21 is a useful adjunct therapy to HT to improve neurological outcomes in HIE.

Example 16—PIC1 Inhibited Replication of Herpes Simplex Virus Type 1 and Herpes Simplex Virus Type 2

Figure 33:
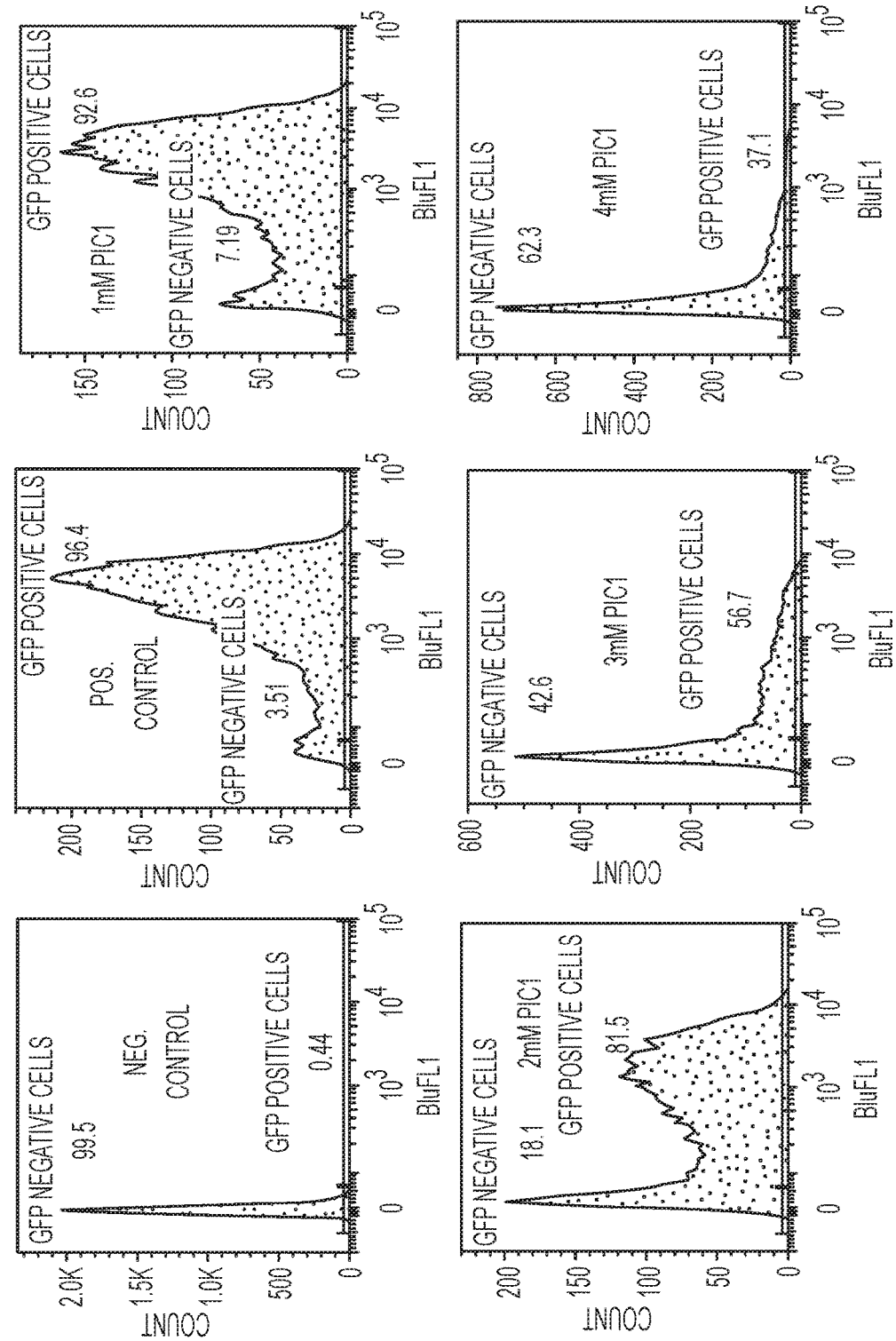
FIG. 33 shows PIC1 (SEQ ID NO: 21) vs. Acyclovir inhibition of HSV-1 encoding GFP. In the no virus, negative control (as labeled), the histogram shows a peak to the left, indicating that there are no infected cells (GFP−). In the positive control, the peak shifts to the right, indicating infected cells (GFP+). In row 2, an increasing concentration of PIC1 (SEQ ID NO: 21) gradually shifts the peak to the left, indicating that PIC1 (SEQ ID NO: 21) inhibits viral replication. In contrast, row 3 shows the dose-dependent effect of Acyclovir (ACV) on viral replication. Treatment with 5 mM of ACV resulted in a small right peak, indicating that there was still residual viral replication.
Figure 33:
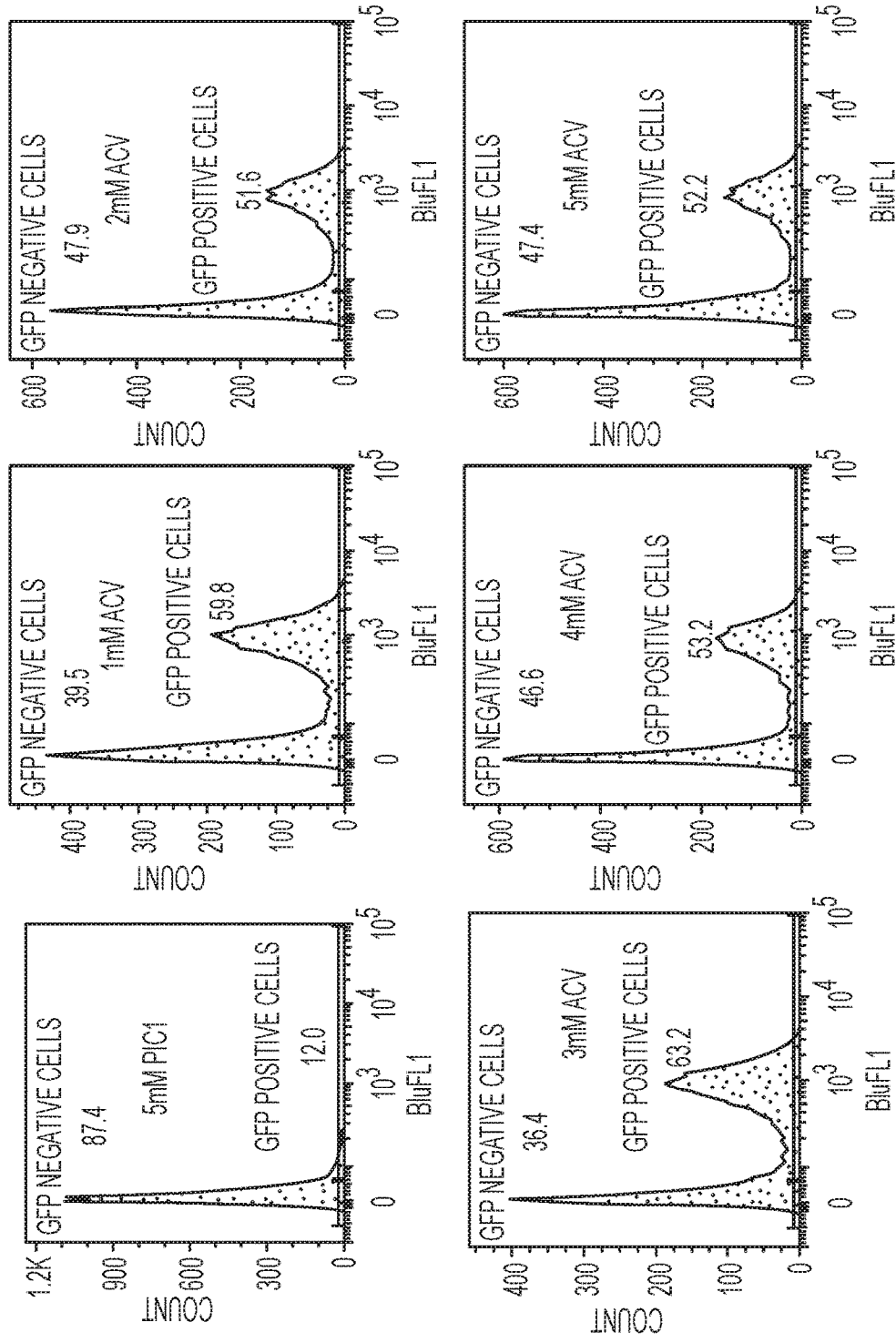
Figure 34:
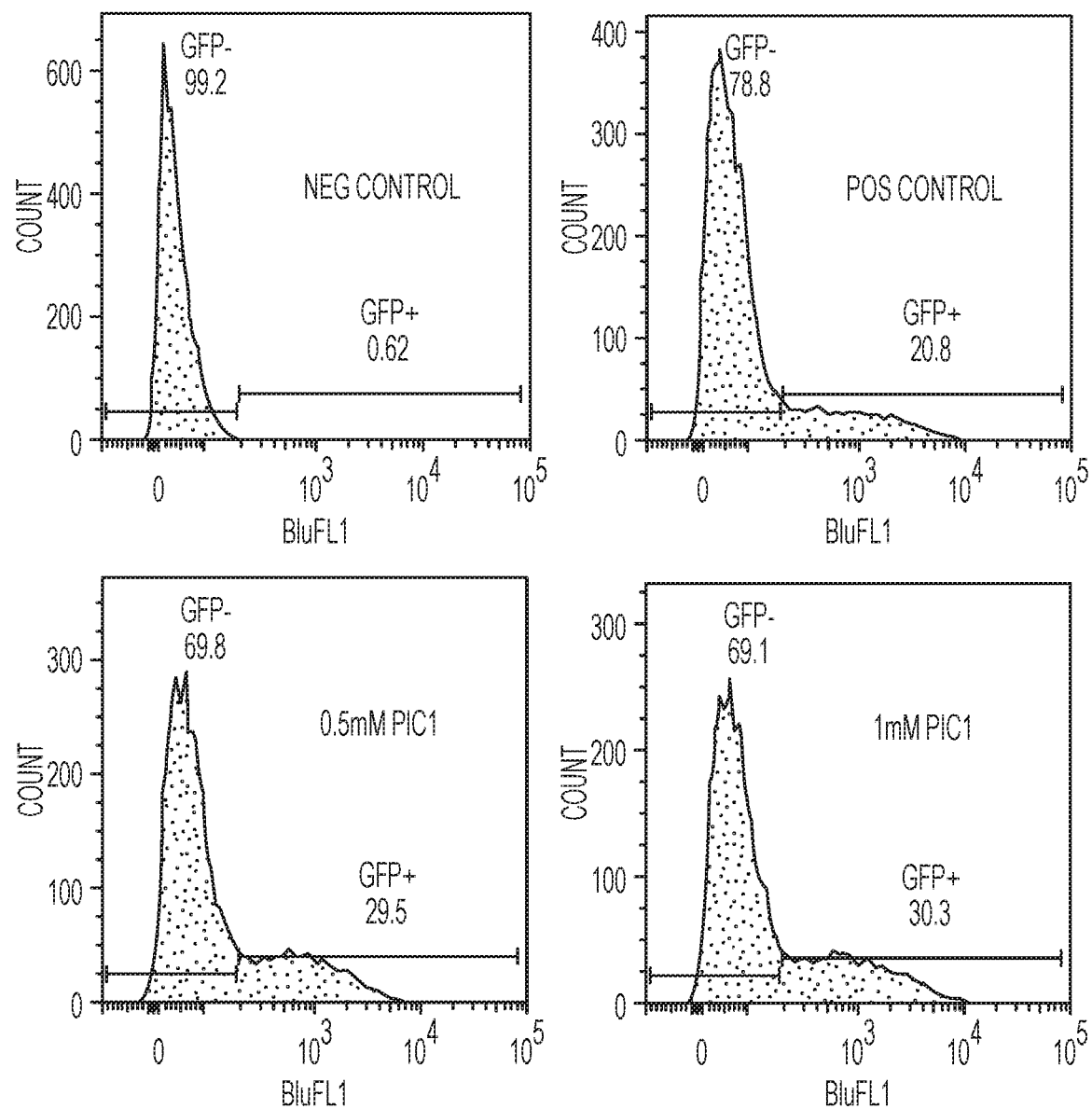
FIG. 34 shows PIC1 (SEQ ID NO: 21) vs. Acyclovir inhibition of HSV-2. In the negative control (as labeled), the histogram shows a peak to the left, indicating that there are no infected cells (GFP−). In the positive control, the peak shifts to the right, indicating infected cells (GFP+). In row 2, an increasing concentration of PIC1 (SEQ ID NO: 21) gradually shifts the peak to the left, indicating that PIC1 (SEQ ID NO: 21) inhibits viral replication.
Figure 34:
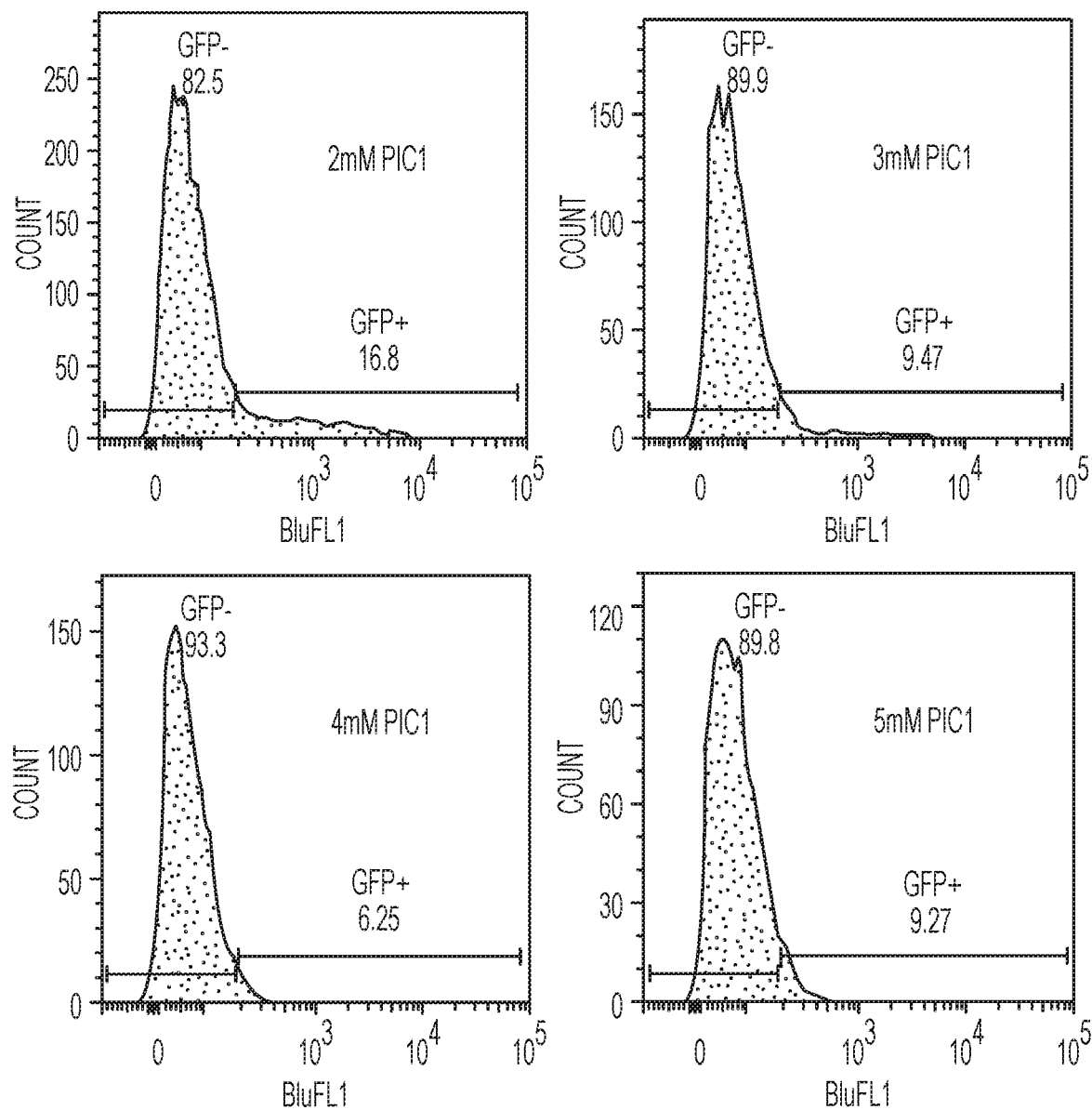

CV-1 cells were infected with HSV-1-GFP for 16 hours. Post-infection, CV-1 cells were detected by flow cytometry (FIG. 33). Uninfected cells (negative control, GFP−) result in a left peak, while the peak in infected cells (GFP+) will shift to the right. When PA-PEG24 (SEQ ID NO: 21) was added to the CV-1 cells before infection, it inhibited viral infection in a dose dependent manner. Acyclovir (the standard of care for severe HSV-1 infections) was also added as a control at the same molar ratio. While Acyclovir was able to inhibit HSV-1 replication significantly, it was never able to completely inhibit replication as indicated by the small GFP+ population of cells. This was in contrast to PA-PEG24 (SEQ ID NO: 21), where there was no detection of GFP+ cells at 4-5 mM PA-PEG24 (SEQ ID NO: 21). In addition, PA-PEG24 (SEQ ID NO: 21) and Acyclovir showed minimal toxicity in CV-1 cells, which indicated that inhibition of viral replication was not due to cell death (FIG. 33). PA-PEG24 (SEQ ID NO: 21) also inhibited replication of HSV-2 in a dose dependent manner (FIG. 34).

Example 17—Peptide Compounds Promoted Growth of *L. acidophilus* and *L. leichmannii*

Figure 35:
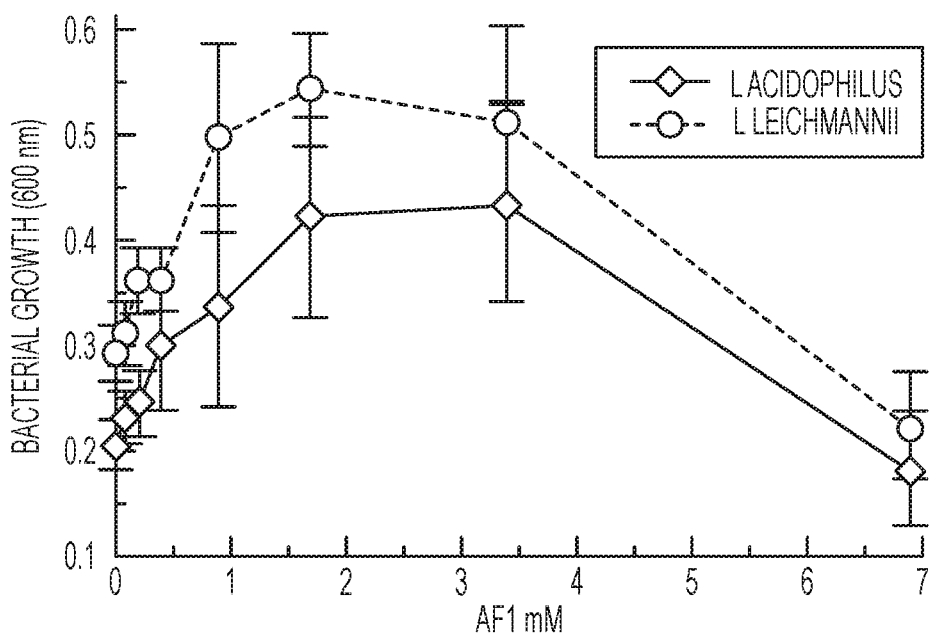
FIG. 35 shows that PIC1 (SEQ ID NO: 21), termed AF1 on the x-axis of the figure, promotes the growth of *L. acidophilus* and *L. leichmannii*.

The ability of PIC1 to not kill beneficial commensal *Lactobacillus* (as shown in FIG. 35) greatly enhances the safety of this antibiotic. The most common side effects of current antibiotics are antibiotic-associated diarrhea and yeast infections because the antibiotics kill normal intestinal flora. Among the most dreaded antibiotic side effects is *C. difficile* colitis, which can be life-threatening and is often recurrent. FIG. 35 shows that PA-PEG24 (SEQ ID NO: 21) can promote growth of *Lactobacillus* in a dose dependent manner.

Example 18—PIC1 had Anti-Microbial Activity

Figure 36A:
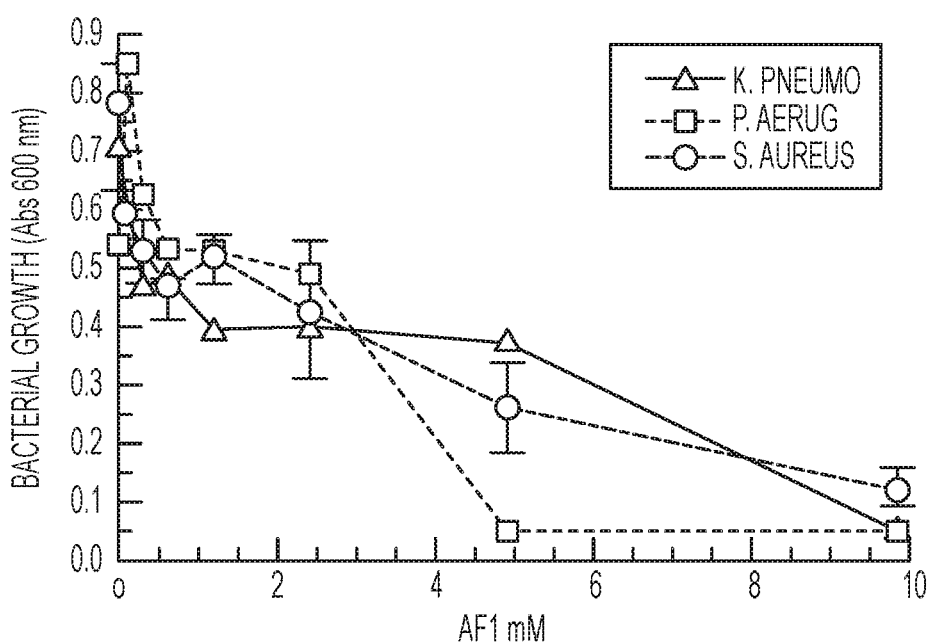
FIG. 36A-C shows the antimicrobial activity of PIC1 (SEQ ID NOS: 7, 8, 12, and 21).
Figure 36B:
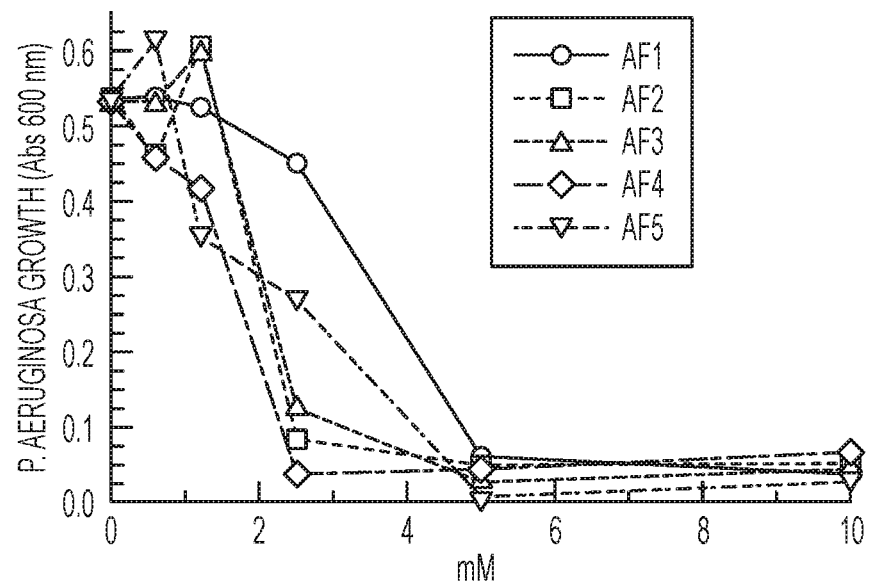
Figure 36C:
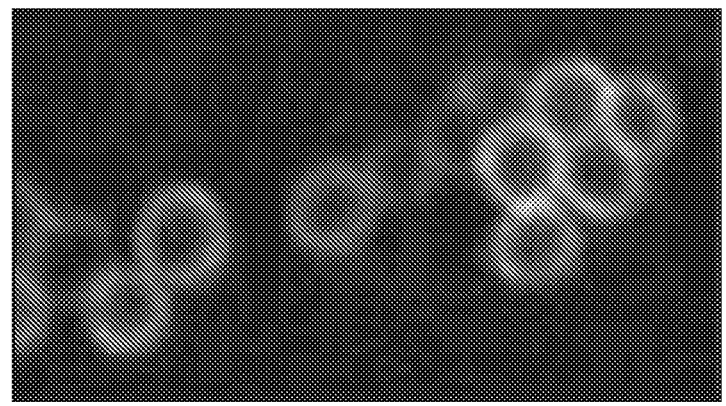

Several PIC1 peptides were anti-bacterial across a broad range of bacterial pathogens. For instance, PA-dPEG24 (also known as AF1, SEQ ID NO: 21) has been shown to inhibit growth of Staphylococcus aureus, Pseudomonas aeruginosa, and Klebsiella pneumoniae in a dose dependent manner (as shown in FIG. 36A). Additionally, Pseudomonas aeruginosa growth (FIG. 36B) was suppressed by five variants of PIC1 (AF1-5) peptides (SEQ ID NOs: 7, 8, 12, and 21. PIC1's (SEQ ID NO: 21) anti-bacterial activity was further confirmed by confocal microscopy, which showed PIC1 peptides bound to the outer surface of Staphylococcus aureus bacteria (FIG. 36C).

Figure 37A:
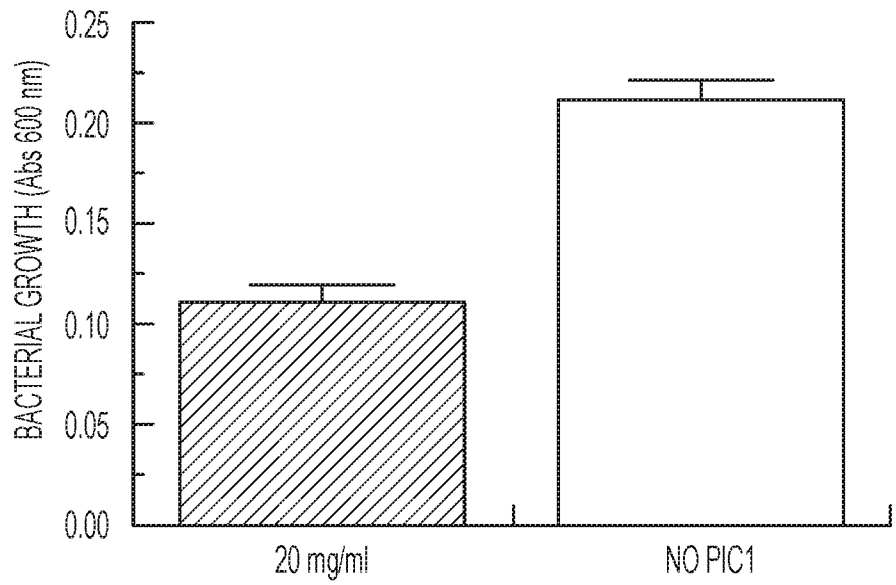
FIG. 37A-D shows *Neisseria gonorrhoeae* growth in presence or absence of PIC1 (SEQ ID NO: 21).
Figure 37B:
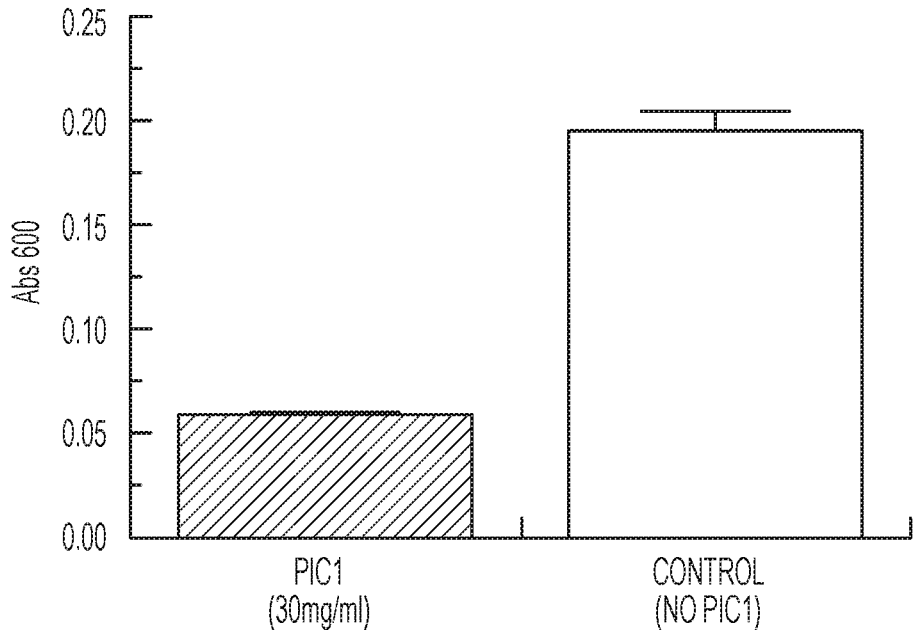
Figure 37C:
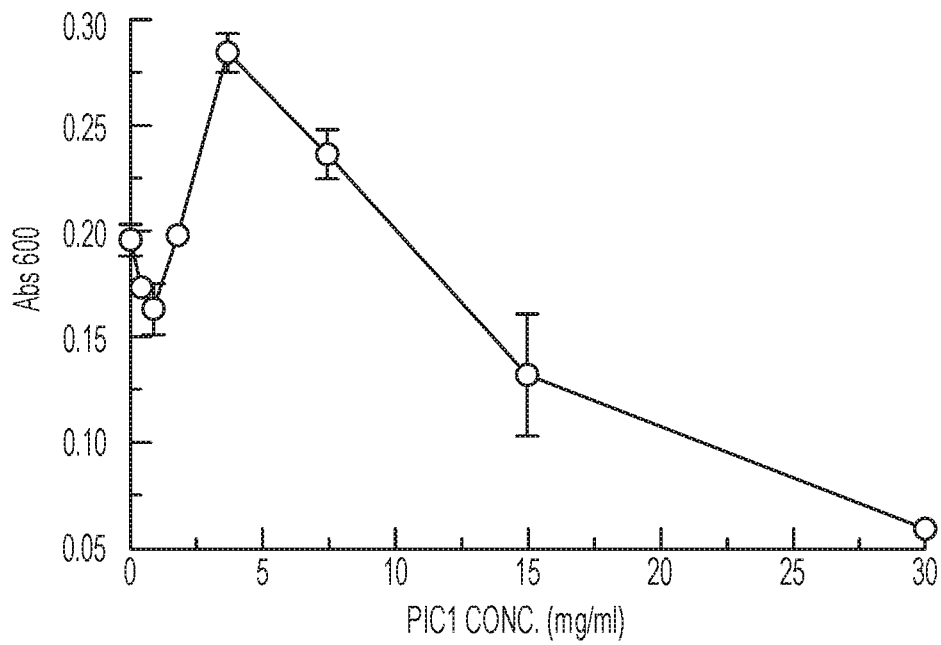
Figure 37D:
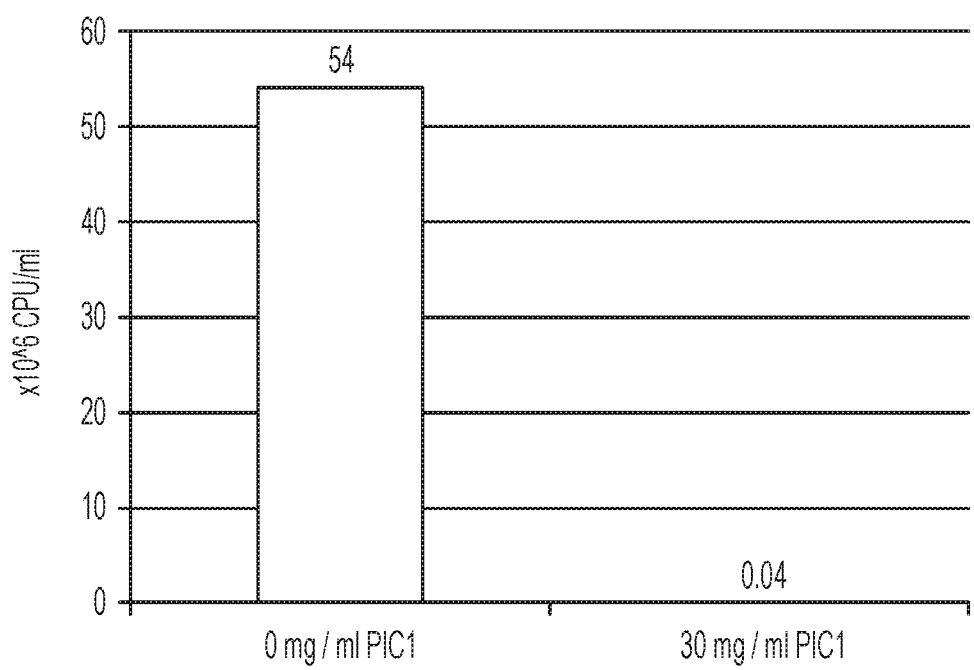

In some embodiments, the peptide compounds inhibited Neisseria gonorrhoeae growth in liquid culture. PA-PEG24 (SEQ ID NO: 21) reduced Neisseria gonorrhoeae growth at 20 mg (FIG. 37A) or 30 mg (FIG. 37B) of PA-PEG24 (SEQ ID NO: 21) and demonstrated dose-dependent inhibition from 0-30 mg/ml PA-PEG24 (SEQ ID NO: 21) (FIG. 37C). Additionally, colony counts from Neisseria gonorrhoeae incubated with or without PA-PEG24 (SEQ ID NO: 21) showed substantial reduction of Neisseria gonorrhoeae colonies treated with 30 mg/ml of PA-PEG24 (SEQ ID NO: 21).

In conclusion, the data show that SEQ ID NO: 21, 5, 6, 7 and 8, respectively, had anti-bacterial activity against a broad range of bacterial pathogens.

Example 19—PIC1 Inhibited Myeloperoxidase (MPO) Activity of Neutrophils

Figure 38:
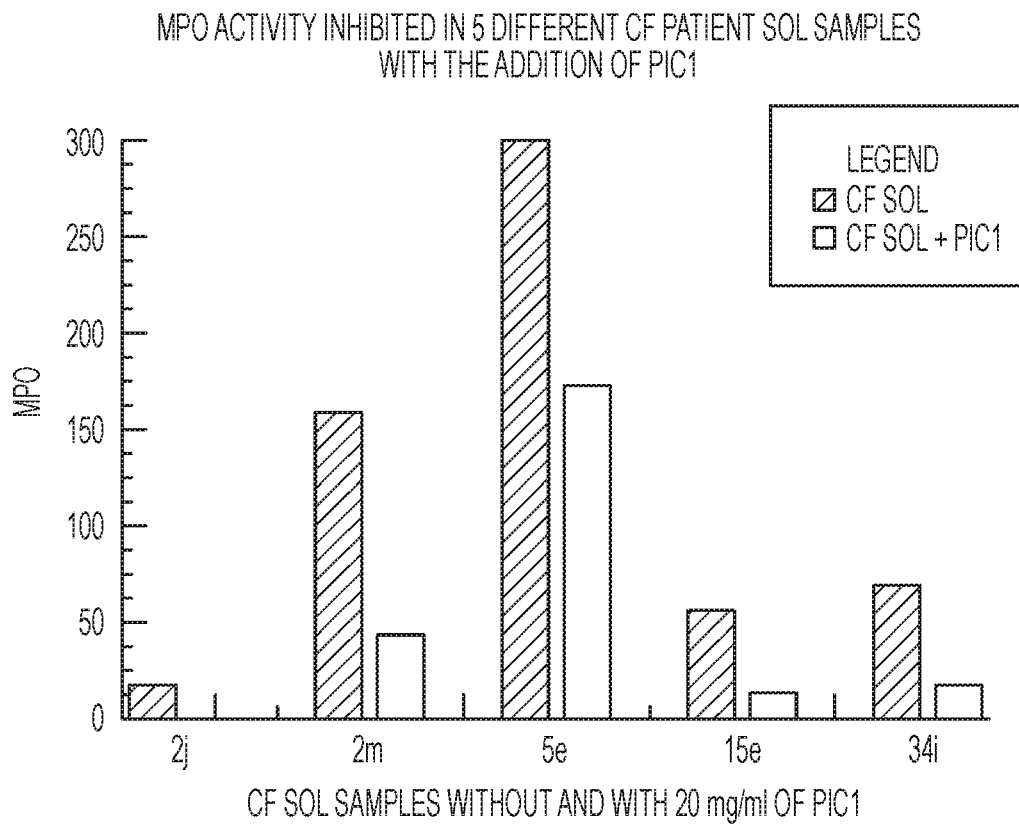
FIG. 38 shows PIC1 (SEQ ID NO: 21) inhibits MPO activity in sputum samples (sol) isolated from cystic fibrosis (CF) patients. CF sol samples were incubated in the presence or absence of 20 mg/ml PIC1 (SEQ ID NO: 21) for 30 minutes followed by addition of TMB for 30 minutes at room temperature. MPO activity was then measured by detection of TMB color change in a spectrophotometer at 450 nm.
Figure 39:
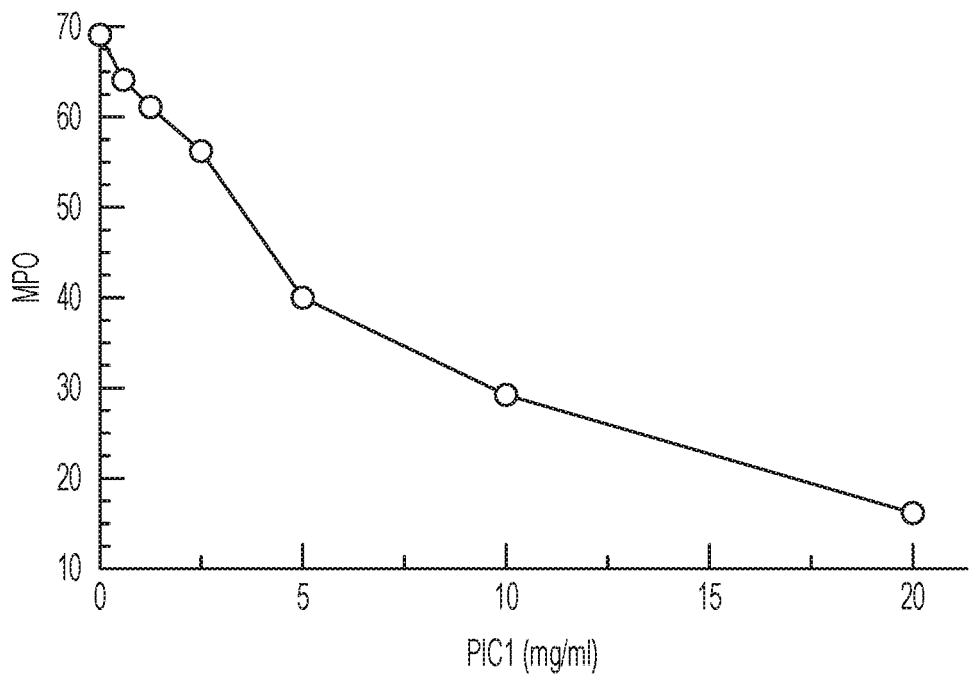
FIG. 39 shows PIC1 (SEQ ID NO: 21) dose-dependently inhibits MPO activity in a sputum samples (sol) isolated from a cystic fibrosis (CF) patient. The CF sol was incubated in the presence of increasing amounts of PIC1 (SEQ ID NO: 21) at room temperature. MPO activity was then measured by detection of TMB color change in a spectrophotometer at 450 nm.
Figure 40:
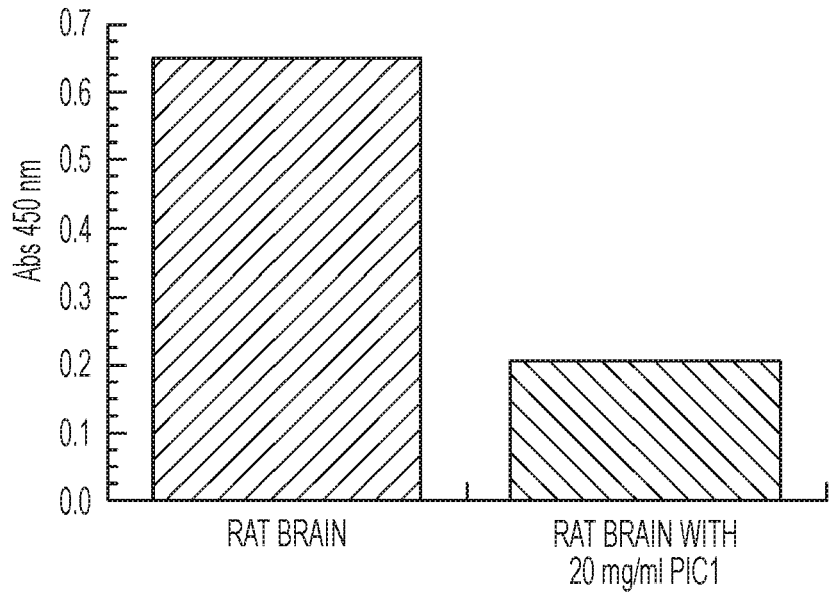
FIG. 40 shows PIC1 (SEQ ID NO: 21) inhibits MPO activity in rat brains subject to hypoxic ischemic encephalopathy (HIE). Supernatants from rat brain lysate that underwent HIE was incubated in the presence or absence of 20 mg/ml PIC1 (SEQ ID NO: 21). MPO activity was then measured by detection of TMB color change in a spectrophotometer at 450 nm.
Figure 41:
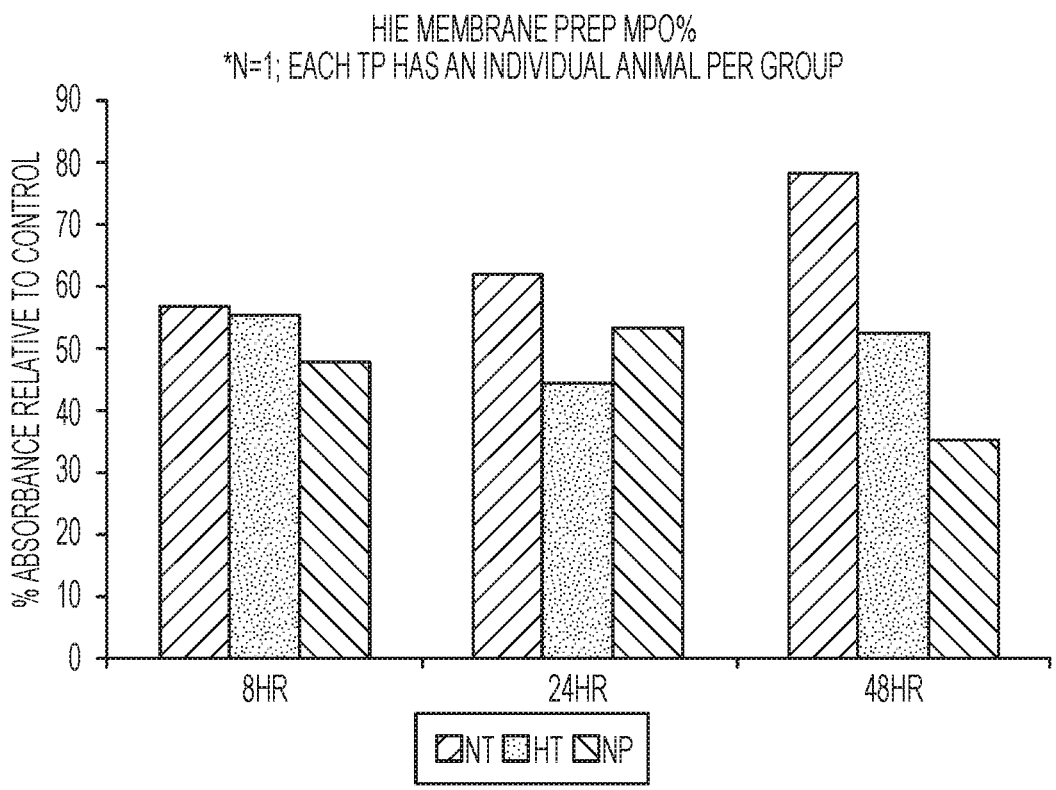
FIG. 41 shows brain lysates from rat pups with HIE either receiving no treatment (NT=normothermia), Hypothermia (HT), or PIC1 (SEQ ID NO: 21) i.p. (NP=normothermia+ PIC1 (SEQ ID NO: 21)). The lysates were then tested for MPO activity with TNB. Over 48 hours the NT animals experience increasing MPO activity consistent with increased reperfusion injury and infarction size. The PIC1 (SEQ ID NO: 21) treated animal shows a trend towards decreased MPO activity compared with no treatment (NT) at each time point, suggesting a decrease in MPO activity in the HIE brain after i.p. administration of PIC1 (SEQ ID NO: 21).
Figure 42:
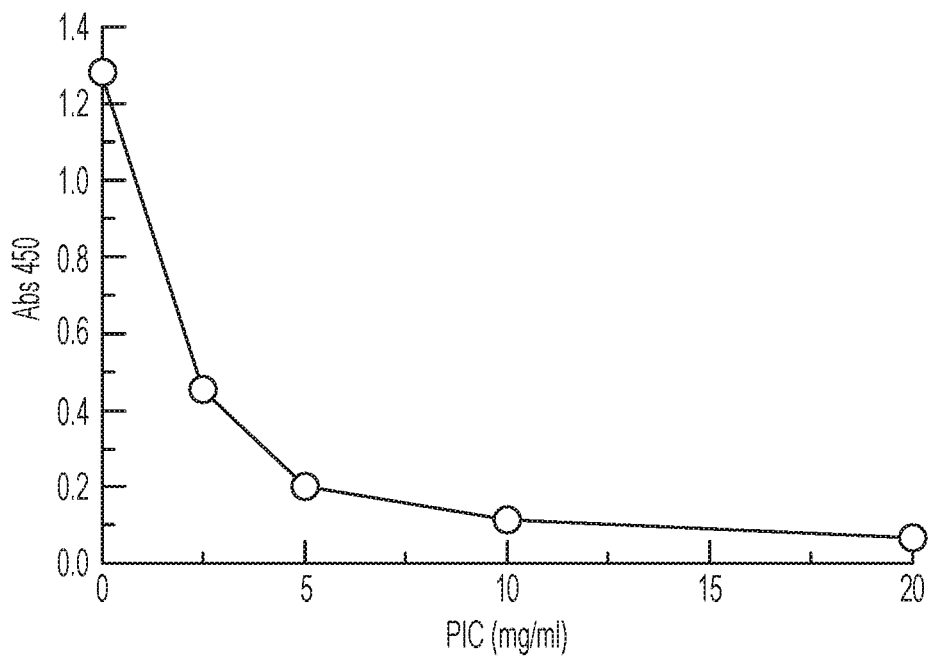
FIG. 42 shows that PIC1 (SEQ ID NO: 21) dose-dependently inhibits MPO activity in lysates of purified human neutrophils (PMN). PMN lysates were incubated in the presence of increasing amounts of PIC1 (SEQ ID NO: 21). MPO activity was then measured by detection of TMB color change in a spectrophotometer at 450 nm.
Figure 43:
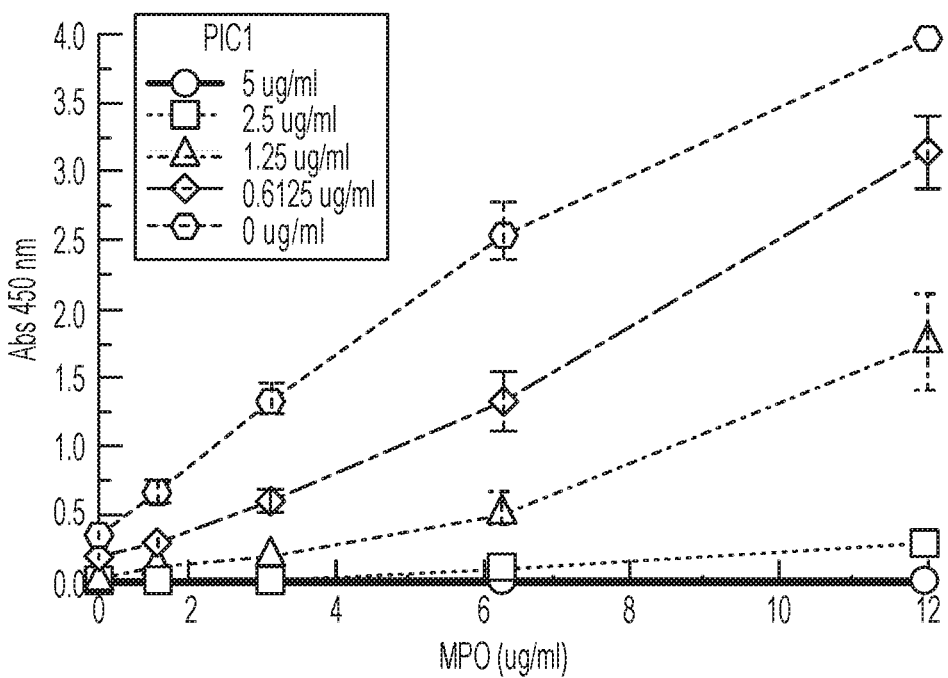
FIG. 43 shows titration of the inhibition of MPO activity by increasing amounts of PIC1 (SEQ ID NO: 21). PIC1 (SEQ ID NO: 21) directly inhibits MPO.

Myeloperoxidase (MPO) is an enzyme from neutrophils that creates hypochlorite (bleach) in acute inflammation that damages invading microbes and host cells alike. This enzyme is known to be destructive to host tissues in Cystic Fibrosis (CF) and Hypoxic Ischemic Encephalopathy (HIE). PIC1 (SEQ ID NO: 21) was found to inhibit MPO activity in sputum samples (sol) isolated from cystic fibrosis (CF) patients. CF sol samples were incubated in the presence or absence of 20 mg/ml PIC1 (SEQ ID NO: 21) for 30 minutes followed by addition of TMB for 30 minutes at room temperature (as shown in FIG. 38). MPO activity was then measured by detection of TMB color change in a spectrophotometer at 450 nm. MPO activity was found to be reduced in CF sol samples treated with PIC1. Preexisting MPO in the sputum of CF patients could have its enzymatic activity blocked with the peptide compounds (FIG. 39 in a dose-dependent manner (FIG. 39). Additionally, PA-PEG24 (SEQ ID NO: 21) was able to block MPO enzymatic activity in a lysate of brain or brain membrane preparations of rats subject to hypoxic ischemic encephalopathy (as shown in FIGS. 40-42). MPO activity present in the lysates of purified human neutrophils can also be directly inhibited by PA-PEG24 (SEQ ID NO: 21) (as shown in FIG. 42). FIG. 42 shows that PA-PEG24 (SEQ ID NO: 21) dose-dependently inhibits MPO activity in lysates of purified human neutrophils (PMN). PMN lysates were incubated in the presence of increasing amounts of PA-PEG24 (SEQ ID NO: 21). MPO activity was then measured by detection of TMB color change in a spectrophotometer at 450 nm. Finally titration of the inhibition of purified MPO activity by PA-PEG24 (SEQ ID NO: 21) demonstrated that PA-PEG24 (SEQ ID NO: 21) can directly inhibit MPO (as shown in FIG. 43). These findings demonstrated that PIC1 has a surprising anti-inflammatory effect that is relevant to both CF and HIE. This shows an alternative mechanism that could explain how SEQ ID NO: 3-47 have anti-inflammatory activity.

Figure 44:
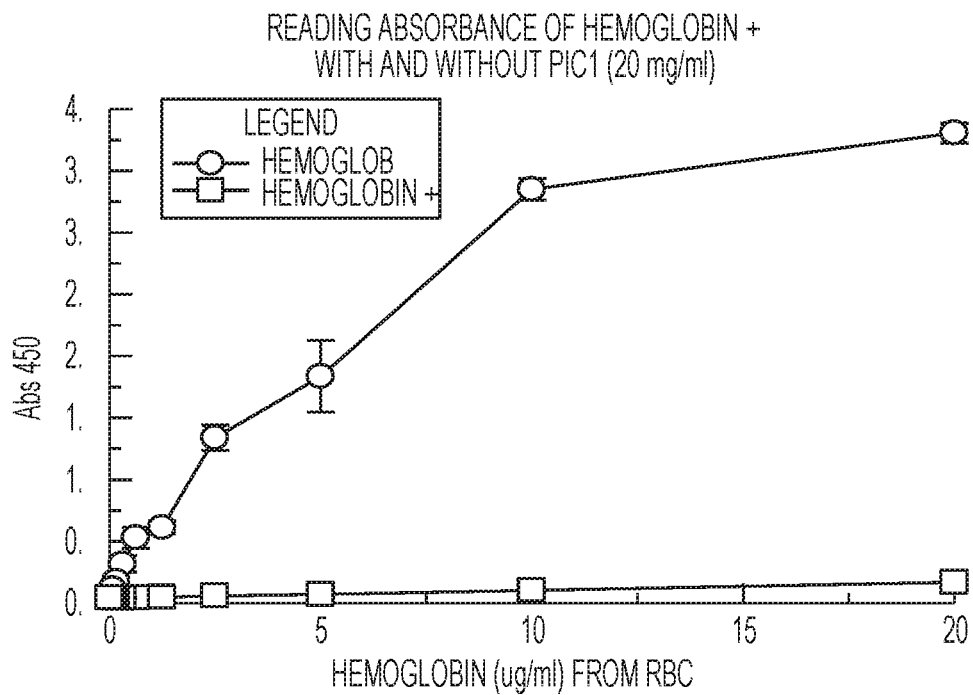
FIG. 44 shows that increasing amounts of RBC lysates containing hemoglobin demonstrated a dose-dependent increase in the oxidation of the chromogen tetramethylbenzidine (TMB) substrate. In the presence of PIC1 (SEQ ID NO: 21) at 20 mg/ml, the oxidation of TMB was inhibited.
Figure 45:
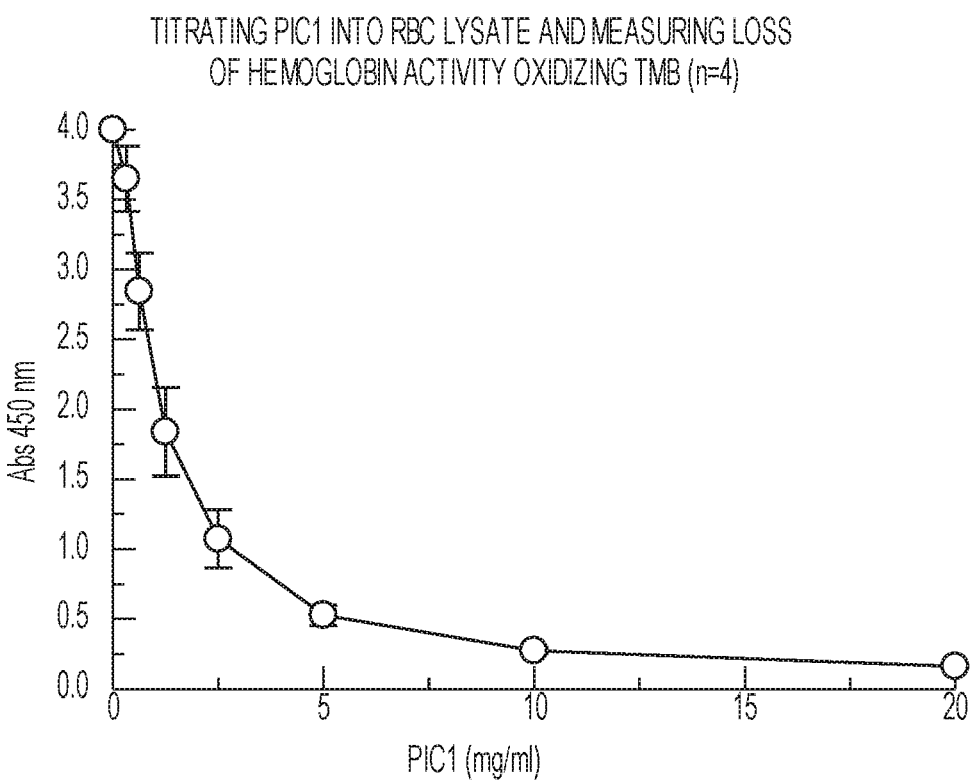
FIG. 45 shows increasing amounts of PIC1 (SEQ ID NO: 21) led to a dose-dependent decrease in oxidized TMB signal by hemoglobin from RBC lysates.
Figure 46:
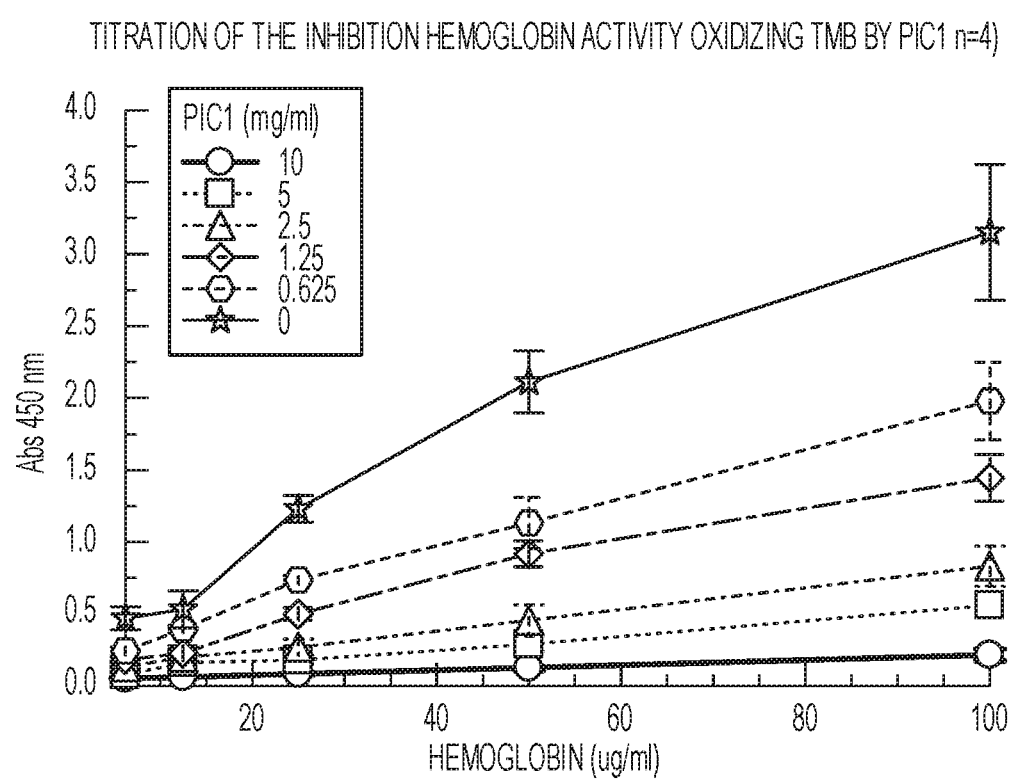
FIG. 46 shows that increasing amounts of PIC1 (SEQ ID NO: 21) dose-dependently inhibited oxidation of tetramethylbenzidine TMB with increasing amounts of hemoglobin from RBC lysate.

Example 20—Acute Kidney Injury and Rhabdomyolysis: Peptide Compounds Inhibited Hemoglobin Production of Free Radical Activity Peptide compounds inhibited the pseudo-peroxidase activity of hemoglobin (Hg) from human red blood cells. Hg, like myeloperoxidase (MPO), contains a heme group that can catalyze peroxide reactions affecting proteins, nucleic acids and lipids that damage host tissues. The pseudo-peroxide activity of Hg is measured using a reaction between hydrogen peroxide ($H_2O_2$) and the chromogen tetramethylbenzidine (TMB). The oxidized TMB displays a color change that can be read in a spectrophotometer. Given that PA-PEG24 (SEQ ID NO: 21) could inhibit MPO peroxidase activity, we tested whether the peroxidase activity of Hg from lysed human RBCs could be inhibited by PA-PEG24 (SEQ ID NO: 21) in the same type of experimental assay. To this end, RBC lysates yielding free Hg were incubated with TMB in absence or presence of PA-PEG24 (SEQ ID NO: 21). As shown in FIG. 44, increasing amounts of RBC lysates gave an increase in absorbance demonstrating increased oxidized TMB substrate. In the presence of 20 mg/ml PA-PEG24 (SEQ ID NO: 21), there was no detectable oxidized TMB. In FIG. 45, increasing amounts of PA-PEG24 (SEQ ID NO: 21) led to a dose-dependent decrease in oxidized TMB signal. FIG. 46 shows a titration of oxidized TMB with increasing amounts of RBC lysate. In the presence of increasing amounts of PA-PEG24 (SEQ ID NO: 21), oxidized TMB signal decreases dose dependently. Hemolysis leading to the presence of free Hg in human circulation is toxic to the kidneys, resulting in acute kidney toxicity and renal failure. Thus, the data supported that PA-PEG24 (SEQ ID NO: 21) can prevent acute kidney injury by reducing hemolysis and pseudo-peroxidase activity caused by the release of free hemoglobin. Thus, the peptides can prevent acute kidney injury, as well as treat or prevent hemolytic conditions such as, e.g., sickle cell disease, hemolytic transfusion reaction, autoimmune hemolysis, etc.

Figure 27A:
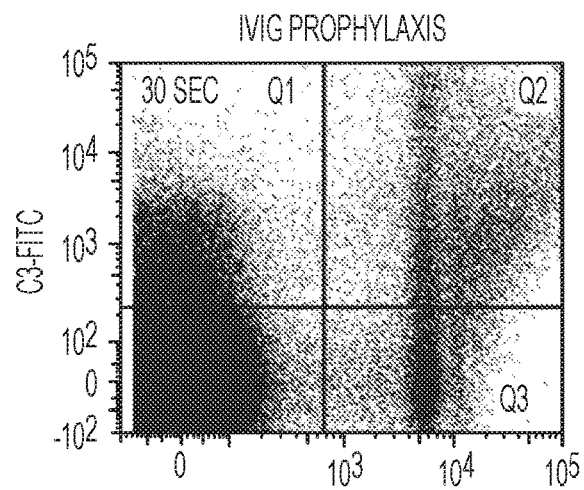
FIGS. 27A-F shows PA-dPEG24 (SEQ ID NO: 21) protection of human RBCs transfused into rats as compared to immune globulin intravenous (IVIG) at 30 seconds (FIGS. 27A and 27D), 5 minutes (FIGS. 27B and 27E) and 20 minutes (FIGS. 27C and 27F) post-transfusion. Flow cytometry analysis of RBCs recovered from blood draws and labeled with anti-glycophorin A (APC) and anti-C3 (FITC).
Figure 27D:
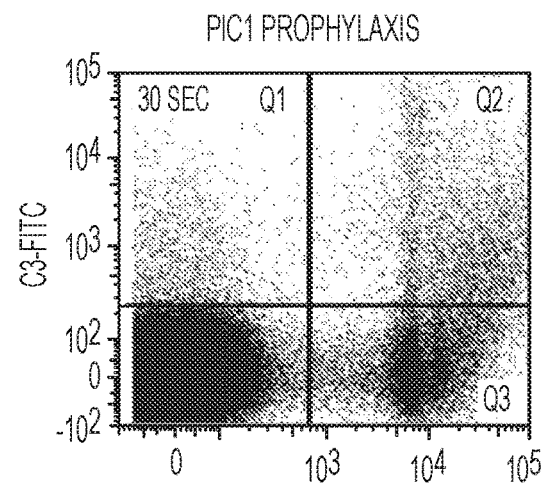
Figure 27B:
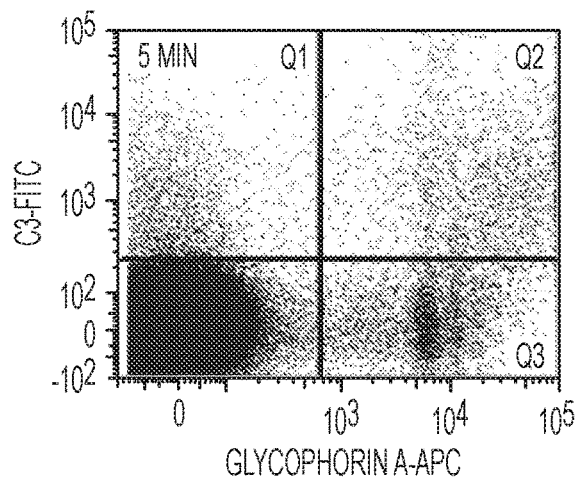
Figure 27E:
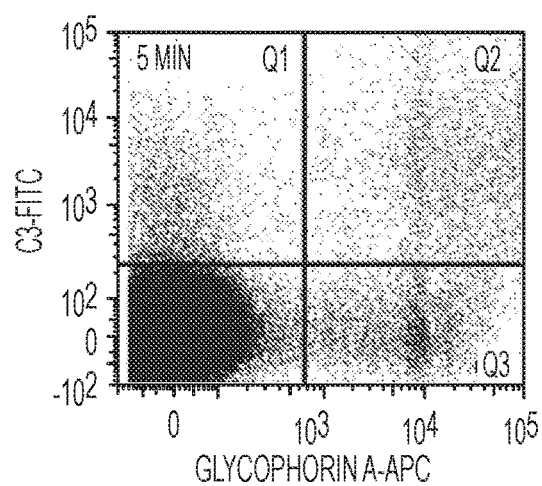
Figure 27C:
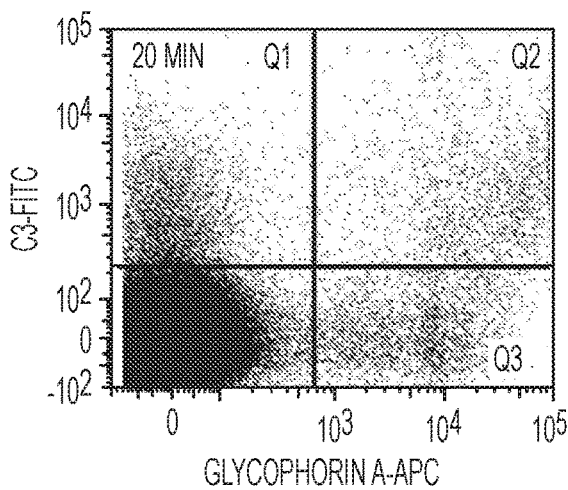
Figure 27F:
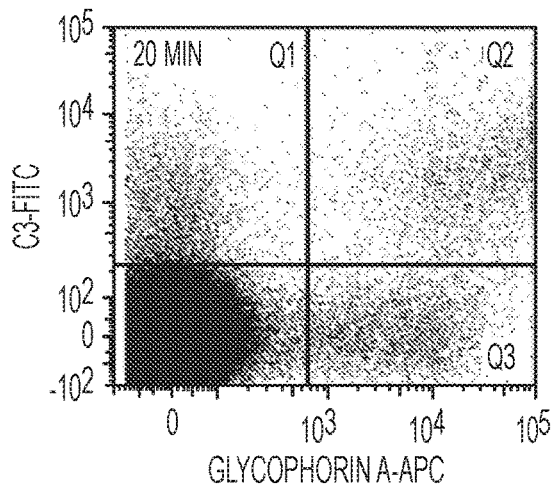
Figure 28A:
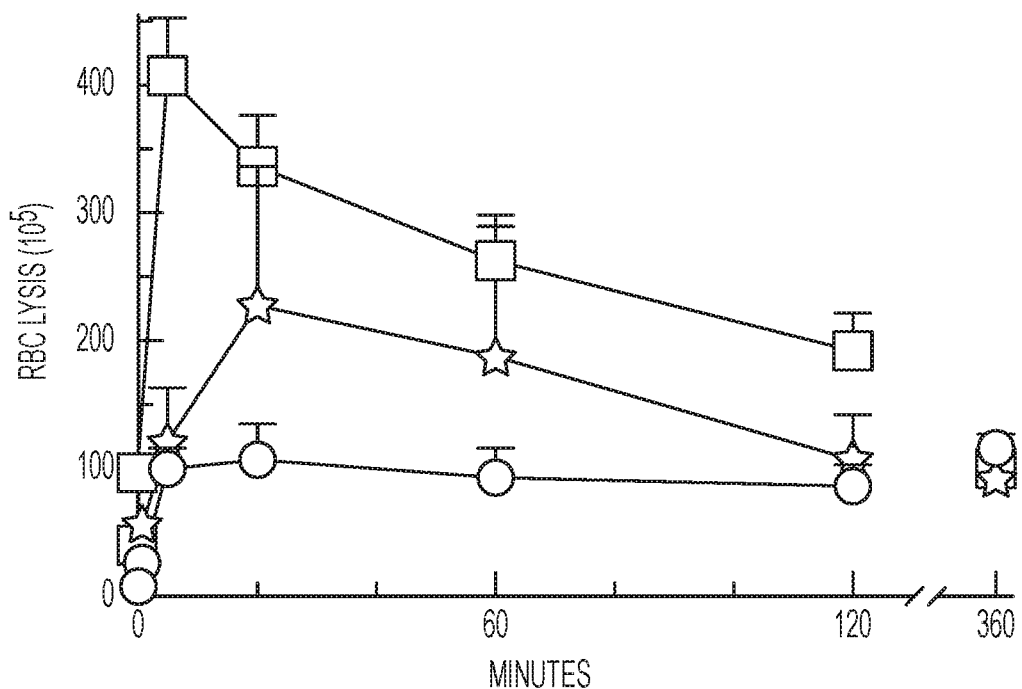
FIGS. 28A-C shows prophylactic PA-dPEG24 (SEQ ID NO: 21) efficacy as compared to prophylactic immune globulin intravenous (IVIG).
Figure 28B:
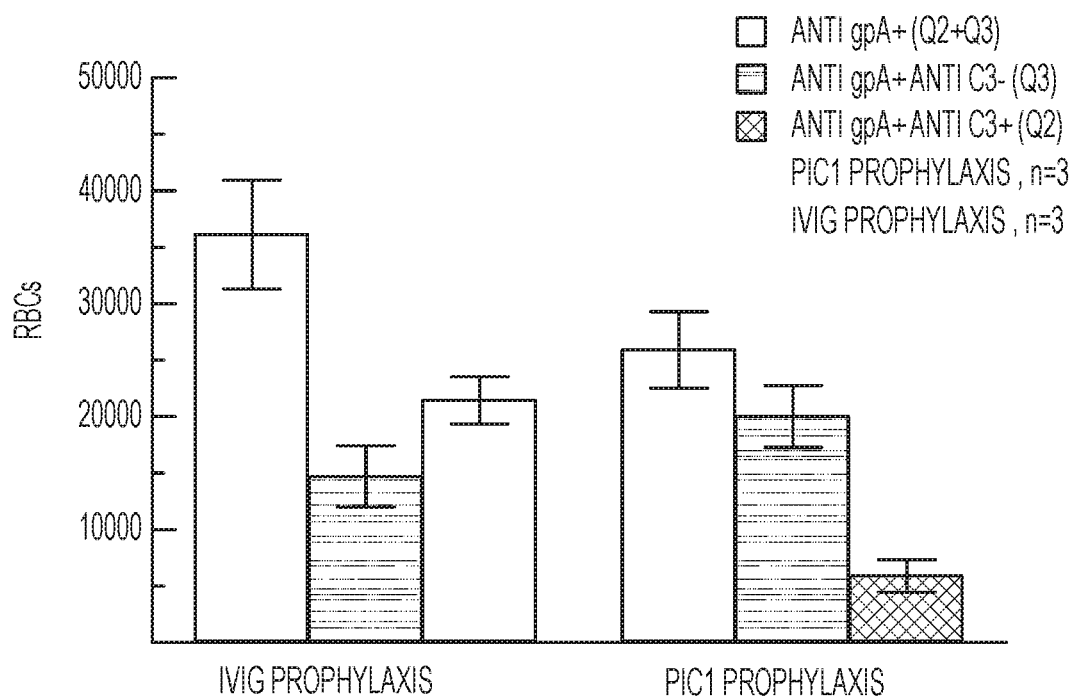
Figure 28C:
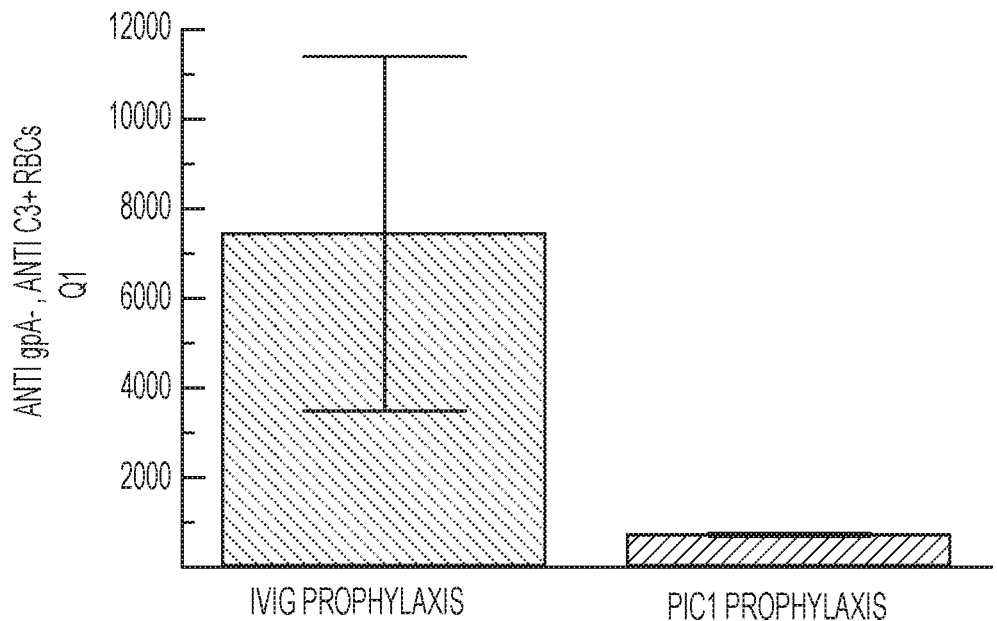
Figure 28D:
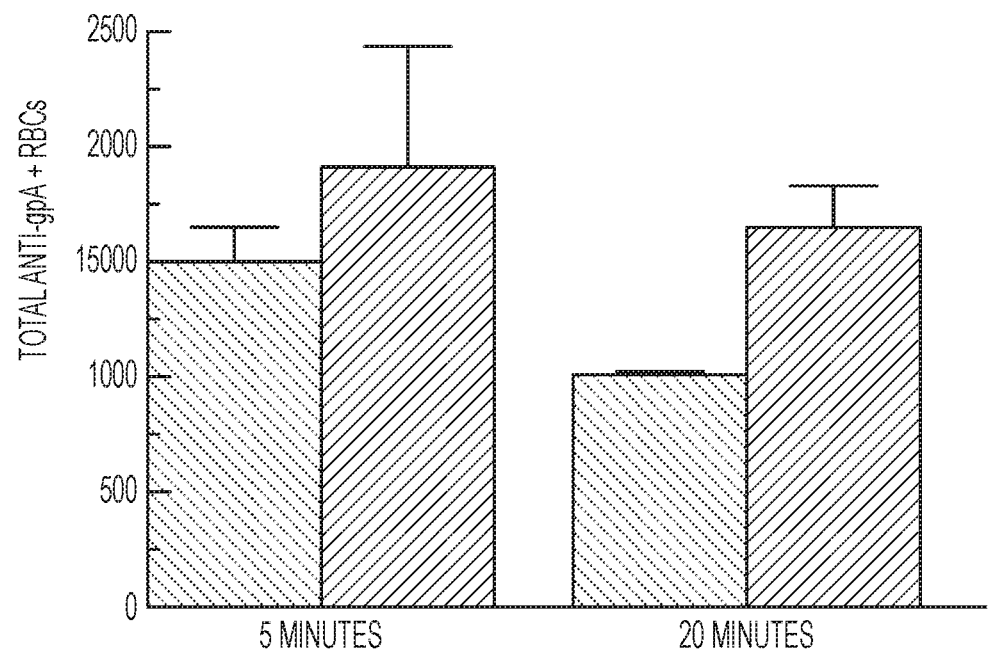
FIG. 28D shows Total anti-gpA1 RBCs for IVIG (no lines) and PIC1 (diagonal lines) prophylaxis at 5 and 20 minutes after transfusion.

To compare the activity of IVIG versus PIC1, animals were treated prophylactically with an equal dose of IVIG or PIC1 (40 mg/animal) or saline control. Blood of animals that received IVIG or PIC1 before xenotransfusion were subject to two-color flow cytometry probing for both F human glycophorin A expression and bound C3 fragments. Representative flow cytometry plots of RBCs at 0.5, 5, and 20 minutes post-transfusion are shown for IVIG (FIG. 27A-C) and PIC1 (FIG. 27D-F) animals. FIG. 28A shows hemolysis measured as free Hb for animals receiving IVIG or PIC1 prophylactically compared to saline control. At 30 seconds after transfusion, PIC1-treated animals demonstrated increased numbers of C3-negative human RBCs (p 5 0.05) and a 3.6-fold (p 5 0.04) decrease in C3-opsonized human RBCs compared with IVIG treated animals (FIG. 28B). At 30 seconds after transfusion, PIC1-treated animals showed a trend toward decreased C3 opsonization of nonhuman (glycophorin A—negative) RBCs (p 5 0.08) compared with IVIG animals (FIG. 28C). Total surviving human RBCs at 20 minutes was increased 1.6-fold (p 5 0.03) for PIC1-treated compared with IVIG treated animals (FIG. 28D).

Figure 29A:
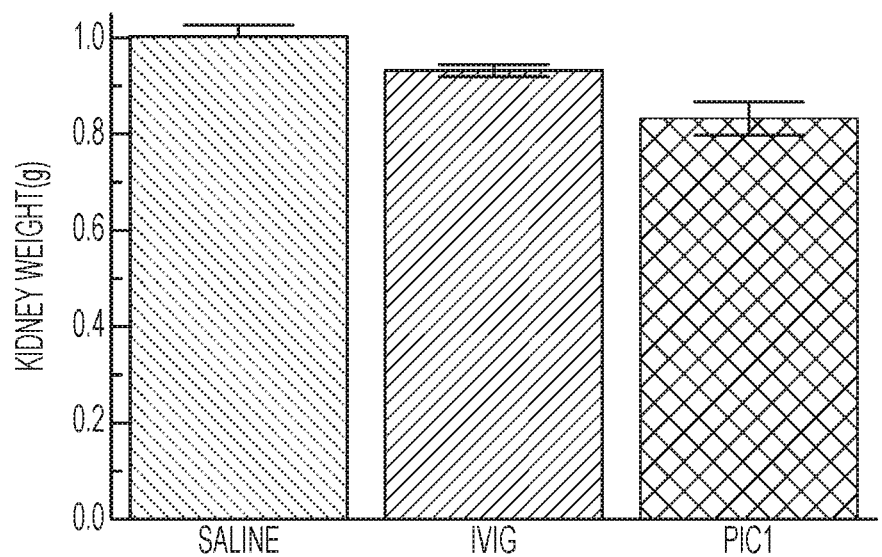
FIGS. 29A-C shows prophylactic PA-dPEG24 (SEQ ID NO: 21)(labeled as PIC1) efficacy as compared to prophylactic immune globulin intravenous (IVIG) on acute kidney injury.
Figure 29B:
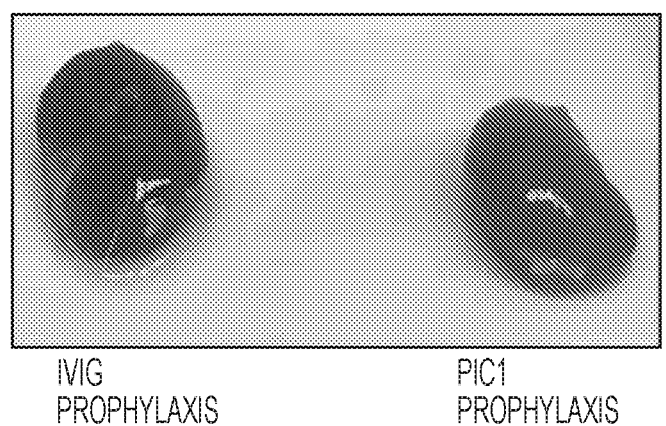
Figure 29C:
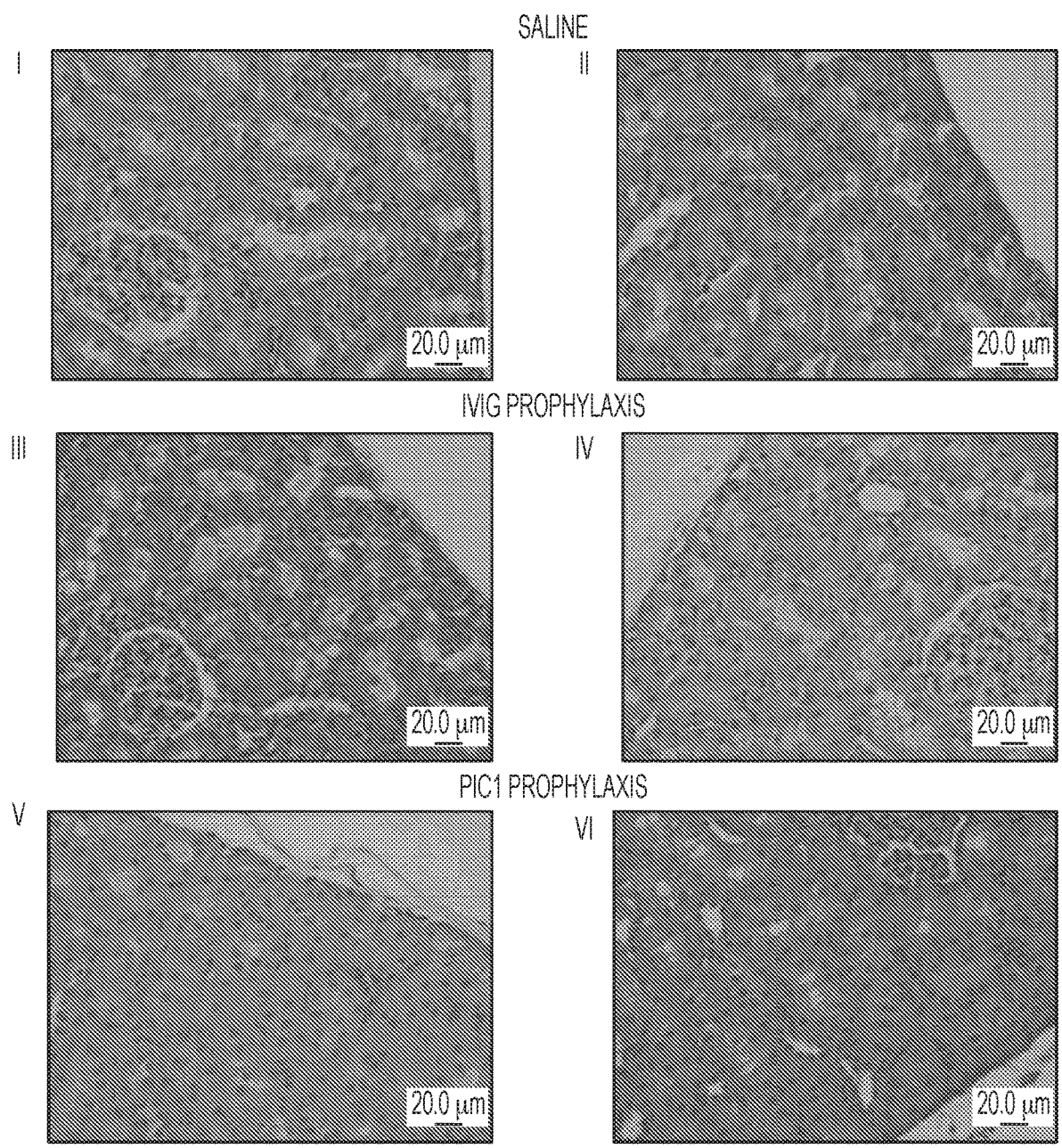

To ascertain if the intravascular toxic free Hb would cause acute kidney injury, the animals were monitored for 6 hours post-transfusion. In the IVIG prophylaxis group, two of the three animals were noted to exhibit gross hematuria as well as three of four animals in the saline group, but the urine of the PIC1-treated animals appeared normal. At necropsy, the kidneys of the IVIG group looked darker and enlarged compared to the kidneys of the PIC1-treated group, which appeared normal (FIG. 29B). On measuring the weight of the kidneys individually, the saline group exhibited a significant increase in weight compared to animals receiving PIC1 (p 5 0.0001) whereas the IVIG group also demonstrated a significant increase in weight compared to animals receiving PIC1 (p 5 0.005), consistent with edematous kidneys (FIG. 29A). Histopathology sections revealed that the saline and IVIG-treated animals had early acute tubular necrosis, as noted by the disappearing nucleus and nuclear material and tubular edema (saline, FIG. 29C, i-ii; IVIG prophylaxis, FIG. 29C, iii-iv) compared to the slight edema, but otherwise healthy kidney architecture for the PIC1 animals (PIC1 prophylaxis, FIG. 29C, v and vi). Taken together, these data demonstrated that PIC1 inhibits hemolysis of the transfused mismatched RBCs preventing subsequent free Hb-associated acute kidney injury.

Rhabdomyolysis is a serious syndrome caused by direct or indirect muscle injury resulting from crush injuries, certain infections, use of certain medications, seizures and other events. The resulting injury to tissues causes release of myoglobin, the oxygen-binding protein found in muscle tissue, into the bloodstream. Myoglobin is harmful to kidneys and there is currently no treatment for Rhabdomyolysis. The discovery that PA-PEG24 (SEQ ID NO: 21) can inhibit pseudo-peroxidase activity of hemoglobin (Hg) showed that PA-PEG24 (SEQ ID NO: 21) is efficacious in treating rhabdomyolysis. Because hemoglobin is similar to myoglobin, PA-PEG24's (SEQ ID NO: 21) ability to inhibit hemoglobin suggests its efficacy in inhibiting the peroxidase activity of myoglobin.

Example 21—Toxicity Data for PIC1 Peptides and Variants

Single-dose toxicology studies with PA-PEG24 (SEQ ID NO: 21) in rats for both maximum deliverable dose and upper limit of the effective dose range have been performed. For the maximum deliverable dose (limited by maximum achievable concentration of PA-PEG24 (SEQ ID NO: 21) (60 mg [240 mg/kg] i.v.)) and deliverable volume, in the treatment group, multiple blood draws were performed on six animals for 14 days. No toxicities were seen on the blood work (CBC and complete blood chemistry) over the first 24 hours, 48 hours, day 7 or day 14. A small drop in hemoglobin is noted at 48 hours due to multiple blood draws taken during the first 24 hours. Normal histology was found for in the brain, heart, lungs, liver, spleen, kidneys, and pancreas. The most pertinent blood parameters for this experiment are shown in TABLE 11.

TABLE 11

Max deliverable PIC1: toxicology.

| | Pretreatment (n = 6) | PIC1 48 Hr (n = 6) | PIC1 Day 7 (n = 6) | PIC1 Day 14 (n = 6) | Units |
|---|---|---|---|---|---|
| WBC | 5.5 (±1.6) | 10.5 (±2.9) | 5.4 (±1.12) | N/A | $10^3$/mL |
| RBC | 6.2 (±0.3) | 5.3 (±0.3) | 5.8 (±0.5) | N/A | $10^6$/μL |
| Platelets | 1004 (±130) | 1045 (±156) | 623 (±417) | N/A | $10^3$/μL |
| AST | 98.2 (±15.4) | 69.0 (±8.7) | 84.3 (±6.74) | 104 (±15) | U/L |
| ALT | 76.3 (±20.0) | 44.0 (±10.4) | 76.3 (±10.9) | 55.8 (±5.6) | U/L |
| AlkPhos | 150 (±29) | 194 (±29) | 147 (±34) | 154 (±42) | U/L |
| Bilirubin | 0.1 (±0) | 0.1 (±0) | 0.1 (±0) | 0.1 (±0) | mg/dL |
| GGT | 1.2 (±0.4) | 1 (±0) | 1 (±0) | 1 (±0) | U/L |
| BUN | 12.3 (±2.3) | 15.8 (±2.1) | 13.5 (±1.64) | 14.7 (±1.0) | mg/dL |
| Creatinine | 0.3 (±0.1) | 0.3 (±0) | 0.4 (±0.1) | 0.4 (±0.1) | mg/dL |
| Lipase | 10.3 (±2.0) | 10.3 (±1.5) | 8.5 (±1.05) | 9.7 (±2.0) | U/L |
| CPK | 454 (±200) | 142 (±47) | 316 (±90) | 580 (±172) | U/L |

Toxicity studies were later performed with larger numbers of animals (n=18 in the treatment group) using a high-dose at the upper end of the therapeutic range (PA-PEG24 (SEQ ID NO: 21) at 40 mg [160 mg/kg] i.v.). Eight animals were sacrificed at day 3, and ten were sacrificed at day 14. Blood chemistry assay results (CBC, superchem, and coagulation) showed no differences between pretreatment, day 3 or day 14 values (TABLE 12). There was no histological evidence for toxicity in any organ (including brain, heart, lungs, liver, spleen, kidneys, and pancreas) at either time point. Thus, single-dose toxicological evaluation of SEQ ID NO: 21 revealed no safety concerns.

TABLE 12

High-dose PIC1: toxicology.

| | Pretreatment (n = 18) | PIC1 48 Hr (n = 8) | PIC1 Day 14 (n = 10) | Units |
|---|---|---|---|---|
| WBC | 6.6 (±1.4) | 6.0 (±3.0) | 7.3 (±2.5) | $10^3$/mL |
| RBC | 6.5 (±1.4) | 5.8 (±0.5) | 6.6 (±0.4) | $10^6$/μL |
| Platelets | 927 (±195) | 987 (±93) | 825 (±229) | $10^3$/μL |
| AST | 102 (±16) | 108 (±26) | 111 (±14) | U/L |
| ALT | 62.1 (±12.1) | 62.8 (±4.0) | 77.4 (±13.9) | U/L |
| AlkPhos | 142 (±59) | 104 (±19) | 115 (±56) | U/L |
| Bilirubin | 0.1 (±0) | 0.1 (±0) | 0.1 (±0) | mg/dL |
| GGT | 1.0 (±0) | 1.0 (±0) | 1.1 (±0.4) | U/L |
| BUN | 10.9 (±2.0) | 17.8 (±3.2) | 13.2 (±1.9) | mg/dL |
| Creatinine | 0.3 (±0) | 0.3 (±0) | 0.3 (±0) | mg/dL |
| Lipase | 5.9 (±1.1) | 11.8 (±1.5) | 6.4 (±1.3) | U/L |
| CPK | 544 (±208) | 538 (±128) | 592 (±163) | U/L |

What is claimed is:

1. A method of treating a viral infection in a subject in need thereof comprising: administering to the subject in need thereof a composition comprising a therapeutically effective amount of a synthetic peptide comprising at least about 90% sequence identity to an amino acid sequence selected from the group consisting of SEQ ID NO: 3-47, wherein the viral infection is caused by herpes simplex virus 1 (HSV-1) or herpes simplex virus 2 (HSV-2).

2. The method of claim 1, wherein the synthetic peptide has the amino acid sequence of SEQ ID NO: 21.

3. The method of claim 1, wherein the composition comprises at least one pharmaceutically acceptable carrier, diluent, or excipient.

4. The method of claim 1, wherein the synthetic peptide has the amino acid sequence selected from the group consisting of SEQ ID NO: 4-18 and 30-47.

5. The method of claim 1, wherein the synthetic peptide has the amino acid sequence selected from the group consisting of SEQ ID NO: 19-29.

6. The method of claim 2, wherein the composition comprises at least one pharmaceutically acceptable carrier, diluent, or excipient.

7. The method of claim 4, wherein the composition comprises at least one pharmaceutically acceptable carrier, diluent, or excipient.

8. The method of claim 5, wherein the composition comprises at least one pharmaceutically acceptable carrier, diluent, or excipient.

* * * * *